US006284949B1

(12) United States Patent
Fischhoff et al.

(10) Patent No.: US 6,284,949 B1
(45) **Date of Patent: *Sep. 4, 2001**

(54) **INSECT-RESISTANT PLANTS COMPRISING A *BACILLUS THURINGIENSIS* GENE**

(75) Inventors: David A. Fischhoff, Webster Groves; Roy L. Fuchs, St. Charles; Paul B. Lavrik, Kirkwood, all of MO (US); Sylvia A. McPherson, Birmingham, AL (US); Frederick J. Perlak, St. Louis, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/027,998

(22) Filed: Feb. 23, 1998

Related U.S. Application Data

(63) Continuation of application No. 08/759,446, filed on Dec. 5, 1996, now Pat. No. 5,763,241, which is a continuation of application No. 08/435,101, filed on May 4, 1995, now abandoned, which is a division of application No. 08/072,281, filed on Jun. 4, 1993, now Pat. No. 5,495,071, which is a continuation of application No. 07/523,284, filed on May 14, 1990, now abandoned, which is a continuation of application No. 07/044,081, filed on Apr. 29, 1987, now abandoned.

(51) Int. Cl.[7] .............................. A01H 5/00; C12N 5/14; C12N 15/32; C12N 15/82

(52) U.S. Cl. ....................... 800/302; 435/320.1; 435/419; 536/23.71

(58) Field of Search ........................ 536/23.71; 435/69.1, 435/320.1, 419, 468; 800/279, 302

(56) References Cited

U.S. PATENT DOCUMENTS

| | | | | |
|---|---|---|---|---|
| 4,766,203 | | 8/1988 | Krieg et al. | 424/90 |
| 4,771,131 | * | 9/1988 | Herrnstadt et al. | 536/27 |
| 5,254,799 | | 10/1993 | DeGreve et al. | 800/205 |
| 5,300,629 | | 4/1994 | Casteels et al. | 530/326 |
| 5,317,096 | | 5/1994 | DeGreve et al. | 536/23.71 |
| 5,338,544 | * | 8/1994 | Donovan | 424/93.2 |
| 5,495,071 | * | 2/1996 | Fischhoff et al. | 800/205 |
| 5,500,365 | | 3/1996 | Fischhoff et al. | 530/350 |
| 5,516,693 | | 5/1996 | Vaeck et al. | 435/320.1 |
| 5,545,565 | | 8/1996 | DeGreve et al. | 435/320.1 |
| 5,760,181 | | 6/1998 | DeGreve et al. | 530/350 |
| 5,763,241 | * | 6/1998 | Fischhoff et al. | 435/172.3 |
| 5,767,372 | | 6/1998 | DeGreve et al. | 800/205 |
| 5,843,898 | | 12/1998 | DeGreve et al. | 514/12 |

FOREIGN PATENT DOCUMENTS

| | | |
|---|---|---|
| 0 142 924 | 5/1985 | (EP) . |
| 0 149 162 | 7/1985 | (EP) . |
| 193 259 | 9/1986 | (EP) . |
| 0 202 739 | 11/1986 | (EP) . |
| 0 206 613 | 12/1986 | (EP) . |
| 0 213 818 | 3/1987 | (EP) . |
| 0 290 395 | 11/1988 | (EP) . |
| 0 292 435 | 11/1988 | (EP) . |
| 0 305 275 | 3/1989 | (EP) . |
| 0 318 143 | 5/1989 | (EP) . |
| 0 359 472 | 3/1990 | (EP) . |
| 0 116 713 | 5/1990 | (EP) . |
| 0 731 170 | 9/1996 | (EP) . |
| WO 84/02913 | 8/1984 | (WO) . |
| WO 86/01536 | 3/1986 | (WO) . |

OTHER PUBLICATIONS

Adang, M.J., et al., Applications of a *Bacillus thuringiensis* Crystal Protein for Insect Control, Abstract J20 from Journal of Cellular Biochemistry Supplement 10C–UCLA Symposia on Molecular & Cellular Biology (1986).

Barton, et al., *Bacillus thuringiensis*–&–Endotoxin Ecpressin in Transgenic *Nicotiana tabecum* Provides Resistance to Lepidopteran Insects, *Plant Physiol.*, vol. 85, pp. 1103–1109 (1987).

Hernstadt, et al., A new Strain of *Bacillus thuringiensis* with Activity against coleopterna Insects, 6062 *Biotechnology*, Apr. No. 4, pp. 305–308 (1986).

Hofte, et al., *Microbiological Reviews*, vol. 53(2), pp. 242–255 (Jun. 1989).

Höfte, H., et al., Abstract K86 (no title) from Journal of Cellular Biochemistry Supplement 10C–UCLA Symposia on Molecular & Cellular Biology (1986).

Höfte, H., et al., Structural and Functional Analysis of a Cloned Delta Endotoxin of *Bacillus thuringiensis* berliner 1715, *Eur. J. Bioche.*, 161: 273–280 (1986).

McPherson, S.A., et al, *Biotechnology*, vol. 6, pp. 61–66 (1988).

McPherson, S. et al., Abstract H–44, *Abstracts of the Annual Meeting of the American Society for Microbiology* (VS), vol. 88, No. O, p. 152 (1988).

Whiteley, H.R., *Ann. Rev. Microbiol.*, vol. 40, pp. 549–576 (1986).

Vaeck, et al., Transgenic plants protected from insect attack, *Nature*, vol. 328, pp. 30–37 (1987).

Adang, M.J., et al., The reconstruction and expression of *Bacillus thuringiensis* cryIIIA gene in protoplasts and potato plants, *Plant Molecular Biology*, 21: 1131–1145 (1993).

Bernhard, Studies on the delta–endotoxin of *Bacillus thuringiensis* var. tenebrionis, *FEMS Microbiological Letters* 33, pp. 261–265 (1986).

(List continued on next page.)

*Primary Examiner*—Amy J. Nelson
(74) *Attorney, Agent, or Firm*—T. K. Ball; Howrey Simon Arnold & White, LLP

(57) ABSTRACT

A method for producing genetically transformed plants exhibiting toxicity to Coleopteran insects is disclosed. In another aspect, the present invention embraces chimeric plant genes, genetically transformed cells and differentiated plants which exhibit toxicity to Coleopteran insects. In yet another aspect, the present invention embraces bacterial cells and plant transformation vectors comprising a chimeric plant gene encoding a Coleopteran toxin protein of *Bacillus thuringiensis*.

13 Claims, 33 Drawing Sheets

OTHER PUBLICATIONS

Klein, T.M., et al., Factors Influencing Gene Delivery into Zea Mays Cells By High–Velocity Microprojectiles, *Bio/Technology*, vol. 6, pp. 559–563 (1988).

Klier, A., et al., Cloning and expression of the crystal protein genes from *Bacillus thuringiensis* strain berliner 1715, *EMBO J.*, 1: 791–799 (1982).

Koziel, M.G., et al., Field Performance of Elite Transgenic Maize Plants Expressing an Insecticidal Protein Derived from *Bacillus thuringiensis, Bio/Technology*, vol. 11, pp. 194–200 (1993).

Krieg, et al., *Bacillus thuringiensis* var. tenebrionis: ein neuer, gegenüber Larven von Coleopteren wirksamer Pathotyp, *Pathotyp. Z. Ang. Ent.* , 96: 500–508 (1983).

Krieg, et al., Neue Ergebnisse über *Bacillus thuringiensis* var tenebrionis unter besonderer Berücksichtigung seiner Wirkung and den Kartoffelkäfer (Leptinotarsa decemlineata), *Ang. Schadlingshde., Pflanzenschutz., Umweltschutz*, 57: 145–150 (1984).

Murray, E.E., et al., Analysis of unstable RNA transcript of insecticidal crystal protein genes of *Bacillus thuringiensis* in transgenic plants and electroporated protoplasts, *Plant Molecular Biology*, 16: 103 5–1050 (1991).

Perlak, F.J., et al., Insect Resistant Cotton Plants, *Bio/Technology*, vol. 8, pp. 939–943 (1990).

Perlak, F.J., et al., Modification of the coding sequence enhances plant expression of insect control protein genes, *Proc. Natl. Acad. Sci. USA*, 88: 3324–3328 (1991).

Perlak, F.J., et al., Genetically improved potatoes; protection from damage by Colorado potato beetles, *Plant Molecular Biology*, 22: 313–321 (1993).

Schnepf, H.E., et al., Cloning and expression of the *Bacillus thuringiensis* crystal protein gene in *Escherichia coli, Proc. Natl. Acad. Sci. USA*, 78: 2893–2897 (1981).

* cited by examiner

DESIGN OF SYNTHETIC DNA PROBES.

```
    1   2   3   4   5   6   7   8   9   10  11  12  13  14  15
A.  M - N - P - N - N - R - S - E - H - D - T - I - K - T - T
    ATG AAT CCN AAT AAT CGN TCN GAA CAT GAT ACN ATT AAA ACN ACN
          C       C   C AGA AGT   G   C   C       C   G
                          G   C                   A

B.  ATGAATCCTAATAATCG
         C  C  C  C
            A
            G

C.  GAACATGATACAATTAA
      G  C  C  G  C
                  A
```

A. PROTEIN SEQUENCE OF THE N-TERMINI OF PEAKS A AND B OF THE B.T.T. TOXIN AND DEDUCED DNA SEQUENCE.

B. SYNTHETIC A1 PROBE, 32-FOLD DEGENERATE 17-MER, BASED ON AMINO ACIDS 1-6.

C. SYNTHETIC A2 PROBE, 48-FOLD DEGENERATE 17-MER, BASED ON AMINO ACIDS 8-13.

FIG.1

SEQUENCING OF THE *Bacillus Thuringiensis* var. *Tenebrionis*

INSECTICIDAL TOXIN GENE

SEQUENCE OF THE B.t.t. INSECTICIDAL TOXIN GENE AND FLANKING REGIONS

```
                                                H
                                                i
                                                n
                                                f
                                                1
    gagcgactattataatcatacatattttcTATTGGAATGATTAAGATTCCAATAGAATAG
  1 ---------+---------+---------+---------+---------+---------+ 60
    ctcgctgataatattagtatgtataaaagATAACCTTACTAATTCTAAGGTTATCTTATC

                      S
                    M f                     F            M
                    n a                     o            b
                    l N                     k            o
                    1 1                     1            2
    TGTATAAATTATTTATCTTGAAAGGAGGGATGCCTAAAAACGAAGAACATTAAAAACATA
 61 ---------+---------+---------+---------+---------+---------+ 120
    ACATATTTAATAAATAGAACTTTCCTCCCTACGGATTTTTGCTTCTTGTAATTTTTGTAT

    TATTTGCACCGTCTAATGGATTTATGAAAAATCATTTTATCAGTTTGAAAATTATGTATT
121 ---------+---------+---------+---------+---------+---------+ 180
    ATAAACGTGGCAGATTACCTAAATACTTTTTAGTAAAATAGTCAAACTTTTAATACATAA

                              H
         M                    i M         T            N
         n                    n b         a            l
         l                    f o         q            a
         1                    1 2         1            3
    ATGATAAGAAAGGGAGGAAGAAAAATGAATCCGAACAATCGAAGTGAACATGATACAATA
181 ---------+---------+---------+---------+---------+---------+ 240
    TACTATTCTTTCCCTCCTTCTTTTTACTTAGGCTTGTTAGCTTCACTTGTACTATGTTAT

              START     M  N  P  N  N  R  S  E  H  D  T  I  -
```

FIG.5A

```
          M   M         B N           N
          a   n         a l           l
          e   l         n a           a
          2   1         1 4           3
    AAAACTACTGAAAATAATGAGGTGCCAACTAACCATGTTCAATATCCTTTAGCGGAAACT
241 ---------+---------+---------+---------+---------+---------+ 300
    TTTTGATGACTTTTATTACTCCACGGTTGATTGGTACAAGTTATAGGAAATCGCCTTTGA

K  T  T  E  N  N  E  V  P  T  N  H  V  Q  Y  P  L  A  E  T  -

M         D    M                    M    P
                a         r    b                    a    s
                e         a    o                    e    t
                1         1    2                    2    1
    CCAAATCCAACACTAGAAGATTTAAATTATAAAGAGTTTTTAAGAATGACTGCAGATAAT
301 ---------+---------+---------+---------+---------+---------+ 360
    GGTTTAGGTTGTGATCTTCTAAATTTAATATTTCTCAAAAATTCTTACTGACGTCTATTA

P  N  P  T  L  E  D  L  N  Y  K  E  F  L  R  M  T  A  D  N  -

M      A
                a      l
                e      u
                1      1
    AATACGGAAGCACTAGATAGCTCTACAACAAAAGATGTCATTCAAAAAGGCATTTCCGTA
361 ---------+---------+---------+---------+---------+---------+ 420
    TTATGCCTTCGTGATCTATCGAGATGTTGTTTTCTACAGTAAGTTTTTCCGTAAAGGCAT

```
         S
         a    AMS H                            HH
         u    vat p                            ha
         3    rey h                            ae
         A    211 1                            12
                /
     GTAGGTGATCTCCTAGGCGTAGTAGGTTTCCCGTTTGGTGGAGCGCTTGTTTCGTTTTAT
 421 ---------+---------+---------+---------+---------+---------+ 480
     CATCCACTAGAGGATCCGCATCATCCAAAGGGCAAACCACCTCGCGAACAAAGCAAAATA

V  G  D  L  L  G  V  V  G  F  P  F  G  G  A  L  V  S  F  Y  -

D          BH                      M
            r          aa                      b
            a          le                      o
            1          13                      2
                        /
     ACAAACTTTTTAAATACTATTTGGCCAAGTGAAGACCCGTGGAAGGCTTTTATGGAACAA
 481 ---------+---------+---------+---------+---------+---------+ 540
     TGTTTGAAAAATTTATGATAAACCGGTTCACTTCTGGGCACCTTCCGAAAATACCTTGTT

T  N  F  L  N  T  I  W  P  S  E  D  P  W  K  A  F  M  E  Q  -

E         S
     c      E  a         A                   A        M
     o      c  u         l                   l        a
     P      o  3         u                   u        e
     1      B  A         1                   1        3
     GTAGAAGCATTGATGGATCAGAAAATAGCTGATTATGCAAAAAATAAAGCTCTTGCAGAG
 541 ---------+---------+---------+---------+---------+---------+ 600
     CATCTTCGTAACTACCTAGTCTTTTATCGACTAATACGTTTTTTATTTCGAGAACGTCTC

```
         S
        DaH            T           M           N
        rua            a           b           l
        a9e            q           o           a
        263            1           2           3
         /
    TTACAGGGCCTTCAAAATAATGTCGAAGATTATGTGAGTGCATTGAGTTCATGGCAAAAA
601 ---------+---------+---------+---------+---------+---------+ 660
    AATGTCCCGGAAGTTTTATTACAGCTTCTAATACACTCACGTAACTCAAGTACCGTTTTT

L  Q  G  L  Q  N  N  V  E  D  Y  V  S  A  L  S  S  W  Q  K  -

BS
                                sc               A
                                tr               l
                                NF               u
                                11               1
                                 /
    AATCCTGTGAGTTCACGAAATCCACATAGCCAGGGGCGGATAAGAGAGCTGTTTTCTCAA
661 ---------+---------+---------+---------+---------+---------+ 720
    TTAGGACACTCAAGTGCTTTAGGTGTATCGGTCCCCGCCTATTCTCTCGACAAAAGAGTT

N  P  V  S  S  R  N  P  H  S  Q  G  R  I  R  E  L  F  S  Q  -

M
                                                 n
                                                 l
                                                 1
    GCAGAAAGTCATTTTCGTAATTCAATGCCTTCGTTTGCAATTTCTGGATACGAGGTTCTA
721 ---------+---------+---------+---------+---------+---------+ 780
    CGTCTTTCAGTAAAAGCATTAAGTTACGGAAGCAAACGTTAAAGACCTATGCTCCAAGAT

```
                          F
         B  N            An
         b  d            lu
         v  e            u4
         1  1            1H
     TTTCTAACAACATATGCACAAGCTGCCAACACACATTTATTTTTACTAAAAGACGCTCAA
 781 ---------+---------+---------+---------+---------+---------+ 840
     AAAGATTGTTGTATACGTGTTCGACGGTTGTGTGTAAATAAAAATGATTTTCTGCGAGTT

F  L  T  T  Y  A  Q  A  A  N  T  H  L  F  L  L  K  D  A  Q  -

H                    M                    M
     g                    b                    b
     a                    o                    o
     1                    2                    2
     ATTTATGGAGAAGAATGGGGATACGAAAAAGAAGATATTGCTGAATTTTATAAAAGACAA
 841 ---------+---------+---------+---------+---------+---------+ 900
     TAAATACCTCTTCTTACCCCTATGCTTTTTCTTCTATAACGACTTAAAATATTTTCTGTT

I  Y  G  E  E  W  G  Y  E  K  E  D  I  A  E  F  Y  K  R  Q  -

M                                     M
                          a                                     n
                          e                                     l
                          2                                     1
     CTAAAACTTACGCAAGAATATACTGACCATTGTGTCAAATGGTATAATGTTGGATTAGAT
 901 ---------+---------+---------+---------+---------+---------+ 960
     GATTTTGAATGCGTTCTTATATGACTGGTAACACAGTTTACCATATTACAACCTAATCTA

L  K  L  T  Q  E  Y  T  D  H  C  V  K  W  Y  N  V  G  L  D  -

H
                          i
                          n
                          f
                          1
     AAATTAAGAGGTTCATCTTATGAATCTTGGGTAAACTTTAACCGTTATCGCAGAGAGATG
 961 ---------+---------+---------+---------+---------+---------+ 1020
     TTTAATTCTCCAAGTAGAATACTTAGAACCCATTTGAAATTGGCAATAGCGTCTCTCTAC

```
     ACATTAACAGTATTAGATTTAATTGCACTATTTCCATTGTATGATGTTCGGCTATACCCA
1021 ---------+---------+---------+---------+---------+---------+ 1080
     TGTAATTGTCATAATCTAAATTAACGTGATAAAGGTAACATACTACAAGCCGATATGGGT

T  L  T  V  L  D  L  I  A  L  F  P  L  Y  D  V  R  L  Y  P  -

S         H   H
                                             aX        i   i
                                             uh        n   n
                                             3o        f   c
                                             A2        1   2
                                             /
     AAAGAAGTTAAAACCGAATTAACAAGAGACGTTTTAACAGATCCAATTGTCGGAGTCAAC
1081 ---------+---------+---------+---------+---------+---------+ 1140
     TTTCTTCAATTTTGGCTTAATTGTTCTCTGCAAAATTGTCTAGGTTAACAGCCTCAGTTG

K  E  V  K  T  E  L  T  R  D  V  L  T  D  P  I  V  G  V  N  -

DM                                              AT
       ds                                              sa
       et                                              uq
       12                                              21
       /                                               /
     AACCTTAGGGGCTATGGAACAACCTTCTCTAATATAGAAAATTATATTCGAAAACCACAT
1141 ---------+---------+---------+---------+---------+---------+ 1200
     TTGGAATCCCCGATACCTTGTTGGAAGAGATTATATCTTTTAATATAAGCTTTTGGTGTA

N  L  R  G  Y  G  T  T  F  S  N  I  E  N  Y  I  R  K  P  H  -

E                                   BS
                   c                T   N              sc
                   o                h   l              tr
                   R                a   a              NF
                   1                1   4              11
                                                       /
     CTATTTGACTATCTGCATAGAATTCAATTTCACACGCGGTTCCAACCAGGATATTATGGA
1201 ---------+---------+---------+---------+---------+---------+ 1260
     GATAAACTGATAGACGTATCTTAAGTTAAAGTGTGCGCCAAGGTTGGTCCTATAATACCT

```
      Hinf1     Sau96  Hpa2       Mae1       Sau3A
                Ava2
                /
     AATGACTCTTTCAATTATTGGTCCGGTAATTATGTTTCAACTAGACCAAGCATAGGATCA
1261 ---------+---------+---------+---------+---------+---------+ 1320
     TTACTGAGAAAGTTAATAACCAGGCCATTAATACAAAGTTGATCTGGTTCGTATCCTAGT

N D S F N Y W S G N Y V S T R P S I G S -

EcoP1     PflM1                Rsa1
     AATGATATAATCACATCTCCATTCTATGGAAATAAATCCAGTGAACCTGTACAAAATTTA
1321 ---------+---------+---------+---------+---------+---------+ 1380
     TTACTATATTAGTGTAGAGGTAAGATACCTTTATTTAGGTCACTTGGACATGTTTTAAAT

N D I I T S P F Y G N K S S E P V Q N L -

EcoP1                     Hae3
     GAATTTAATGGAGAAAAAGTCTATAGAGCCGTAGCAAATACAAATCTTGCGGTCTGGCCG
1381 ---------+---------+---------+---------+---------+---------+ 1440
     CTTAAATTACCTCTTTTTCAGATATCTCGGCATCGTTTATGTTTAGAACGCCAGACCGGC

```
                                                       S
                       M                              Ba
                       a                              cu
                       e                              l3
                       3                              1A
                                                       /
     TCCGCTGTATATTCAGGTGTTACAAAAGTGGAATTTAGCCAATATAATGATCAAACAGAT
1441 ---------+---------+---------+---------+---------+---------+ 1500
     AGGCGACATATAAGTCCACAATGTTTTCACCTTAAATCGGTTATATTACTAGTTTGTCTA

S  A  V  Y  S  G  V  T  K  V  E  F  S  Q  Y  N  D  Q  T  D  -

H                               H
             R         R     i                  HT     AP    i
             s         s     n                  hh     lv    n
             a         a     f                  aa     uu    f
             1         1     1                  11     12    1
                                                 /      /
     GAAGCAAGTACACAAACGTACGACTCAAAAAGAAATGTTGGCGCGGTCAGCTGGGATTCT
1501 ---------+---------+---------+---------+---------+---------+ 1560
     CTTCGTTCATGTGTTTGCATGCTGAGTTTTTCTTTACAACCGCGCCAGTCGACCCTAAGA

E  A  S  T  Q  T  Y  D  S  K  R  N  V  G  A  V  S  W  D  S  -

S
      CaT                     M            XM      M            N
      lua                     n            ba      n            l
      a3q                     l            ae      l            a
      1A1                     1            11      1            3
       /
     ATCGATCAATTGCCTCCAGAAACAACAGATGAACCTCTAGAAAAGGGATATAGCCATCAA
1561 ---------+---------+---------+---------+---------+---------+ 1620
     TAGCTAGTTAACGGAGGTCTTTGTTGTCTACTTGGAGATCTTTTCCCTATATCGGTAGTT

```
                                                        H
                                  M                    iH
                                  n                    np
                                  l                    ca
                                  1                    21
                                                        /
     CTCAATTATGTAATGTGCTTTTTAATGCAGGGTAGTAGAGGAACAATCCCAGTGTTAACT
1621 ---------+---------+---------+---------+---------+---------+ 1680
     GAGTTAATACATTACACGAAAAATTACGTCCCATCATCTCCTTGTTAGGGTCACAATTGA

L  N  Y  V  M  C  F  L  M  Q  G  S  R  G  T  I  P  V  L  T  -

H
                     A               N   i  AT
                     c               l   n  sa
                     c               a   f  uq
                     1               3   1  21
                                             /
     TGGACACATAAAAGTGTAGACTTTTTTAACATGATTGATTCGAAAAAAATTACACAACTT
1681 ---------+---------+---------+---------+---------+---------+ 1740
     ACCTGTGTATTTTCACATCTGAAAAAATTGTACTAACTAAGCTTTTTTTAATGTGTTGAA

W  T  H  K  S  V  D  F  F  N  M  I  D  S  K  K  I  T  Q  L  -

B             P  S
                        M                s           ADpAMaS M
                        a                p           vruvaut n
                        e                M           aaMre9y l
                        3                1           2212161 1
                                                      //  //
     CCGTTAGTAAAGGCATATAAGTTACAATCTGGTGCTTCCGTTGTCGCAGGTCCTAGGTTT
1741 ---------+---------+---------+---------+---------+---------+ 1800
     GGCAATCATTTCCGTATATTCAATGTTAGACCACGAAGGCAACAGCGTCCAGGATCCAAA

```
                E                            F
                c                            n            M
                o                            u            a
                R                            4            e
                V                            H            3
     ACAGGAGGAGATATCATTCAATGCACAGAAAATGGAAGTGCGGCAACTATTTACGTTACA
1801 ---------+---------+---------+---------+---------+---------+ 1860
     TGTCCTCCTCTATAGTAAGTTACGTGTCTTTTACCTTCACGCCGTTGATAAATGCAATGT

T  G  G  D  I  I  Q  C  T  E  N  G  S  A  A  T  I  Y  V  T  -

E
     H           R  F          T   AM  c                    D
     p           s  o          a   la  o                    d
     a           a  k          q   ue  R                    e
     2           1  1          1   11  1                    1
     CCGGATGTGTCGTACTCTCAAAAATATCGAGCTAGAATTCATTATGCTTCTACATCTCAG
1861 ---------+---------+---------+---------+---------+---------+ 1920
     GGCCTACACAGCATGAGAGTTTTTATAGCTCGATCTTAAGTAATACGAAGATGTAGAGTC

P  D  V  S  Y  S  Q  K  Y  R  A  R  I  H  Y  A  S  T  S  Q  -

B
                 D             B Ns                   T
                 d             a lp                   a
                 e             n a1                   q
                 1             1 42                   1
     ATAACATTTACACTCAGTTTAGACGGGGCACCATTTAATCAATACTATTTCGATAAAACG
1921 ---------+---------+---------+---------+---------+---------+ 1980
     TATTGTAAATGTGAGTCAAATCTGCCCCGTGGTAAATTAGTTATGATAAAGCTATTTTGC

I  T  F  T  L  S  L  D  G  A  P  F  N  Q  Y  Y  F  D  K  T  -

ATAAATAAAGGAGACACATTAACGTATAATTCATTTAATTTAGCAAGTTTCAGCACACCA
1981 ---------+---------+---------+---------+---------+---------+ 2040
     TATTTATTTCCTCTGTGTAATTGCATATTAAGTAAATTAAATCGTTCAAAGTCGTGTGGT

```
AT                  H           AM
sa                  g           ha
uq                  a           ae
21                  1           23
/
TTCGAATTATCAGGGAATAACTTACAAATAGGCGTCACAGGATTAAGTGCTGGAGATAAA
2041 ---------+---------+---------+---------+---------+---------+ 2100
AAGCTTAATAGTCCCTTATTGAATGTTTATCCGCAGTGTCCTAATTCACGACCTCTATTT

F  E  L  S  G  N  N  L  Q  I  G  V  T  G  L  S  A  G  D  K  -

                    X                   M
                    m                   a
                    n                   e
                    1                   1
GTTTATATAGACAAAATTGAATTTATTCCAGTGAATTAAATTAACTAGAAAGTAAAGAAG
2101 ---------+---------+---------+---------+---------+---------+ 2160
CAAATATATCTGTTTTAACTTAAATAAGGTCACTTAATTTAATTGATCTTTCATTTCTTC

V  Y  I  D  K  I  E  F  I  P  V  N  x   STOP

M                                                          M
a                                                          b
e                                                          o
3                                                          2
TAGTGACCATCTATGATAGTAAGCAAAGGATAAAAAAATGAGTTCATAAAATGAATAACA
2161 ---------+---------+---------+---------+---------+---------+ 2220
ATCACTGGTAGATACTATCATTCGTTTCCTATTTTTTTACTCAAGTATTTTACTTATTGT

                                                 M
                                                 b
                                                 o
                                                 2
TAGTGTTCTTCAACTTTCGCTTTTTGAAGGTAGATGAAGAACACTATTTTTATTTTCAAA
2221 ---------+---------+---------+---------+---------+---------+ 2280
ATCACAAGAAGTTGAAAGCGAAAAACTTCCATCTACTTCTTGTGATAAAAATAAAAGTTT
```

FIG.5K

```
                  D               D
                  r               r
                  a               a
                  1               1
     ATGAAGGAAGTTTTAAATATGTAATCATTTAAAGGGAACAATGAAAGTAGGAAATAAGTC
2281 ---------+---------+---------+---------+---------+---------+ 2340
     TACTTCCTTCAAAATTTATACATTAGTAAATTTCCCTTGTTACTTTCATCCTTTATTCAG

                                                       S
                                                       s
                                                       p
                                                       1
     ATTATCTATAACAAAATAACCATTTTTATATAGCCAGAAATGAATTATAATATTAATCTT
2341 ---------+---------+---------+---------+---------+---------+ 2400
     TAATAGATATTGTTTTATTGGTAAAAATATATCGGTCTTTACTTAATATTATAATTAGAA

                                                    H
                                     A          D   iH        S
                                     l          d   ng        s
                                     u          e   fa        p
                                     1          1   11        1
     TTCTAAATTGACGtTTTTCTaAACGTTCTATAGCTTCAAGACGCTTAGAATCATCAATAT
2401 ---------+---------+---------+---------+---------+---------+ 2460
     AAGATTTAACTGCaAAAAGAtTTGCAAGATATCGAAGTTCTGCGAATCTTAGTAGTTATA

                                               H
        A       A            T                 i                B
        c       l            a                 n                g
        c       u            q                 f                l
        1       1            1                 1                2
     TTGTATACAGAGCTGTTGTTTCCATCGAGTTATGTCCCATTTGATTCGCTAATAGAACAA
2461 ---------+---------+---------+---------+---------+---------+ 2520
     AACATATGTCTCGACAACAAAGGTAGCTCAATACAGGGTAAACTAAGCGATTATCTTGTT
```

FIG. 5L

```
     S
     aX                                                  M      F
     uh                                                  n      o
     3o                                                  l      k
     A2                                                  1      1
     //
     GATCTTTATTTTCGTTATAATGATTGGTTGCATAAGTATGGCGTAATTTATGAGGGCTTT
2521 ---------+---------+---------+---------+---------+---------+ 2580
     CTAGAAATAAAAGCAATATTACTAACCAACGTATTCATACCGCATTAAATACTCCCGAAA

TCTTTTCATCCAAAAGCCAAGTGTATTTCTCTGTA
2581 ---------+---------+---------+----- 2615
     AGAAAAGTAGGTTTTCGGTTCACATAAAGAGACAT
```

FIG.5M

| B.t.t. PROTEINS – NATIVE & E.coli CLONES | | | | | |
|---|---|---|---|---|---|
| BAND No. | MW (Kd) | NATIVE B.t.t. | E.coli CLONES<br>pMON5436 | pMON5456<br>pMON5450 | pMON5460 |
| 1 | 73 | — | — | | — |
| 2 | 71 | — | | | |
| 3,3' | 67 | — | — | — | |
| 4 | 66 | — | | | |

DIAGRAM OF B.t.t. PROTEINS. B.t.t. PROTEINS PRODUCED BY *Bacillus Thuringiensis* var. *Tenebrionis* and *E.coli* JM101 (pMON5436, pMON5456, pMON5450, pMON5460) WERE RESOLVED ON 9% SDS-PAGE AND THE RESPECTIVE PATTERNS ARE SHOWN.

FIG.6

N-TERMINI OF B.t.t. PROTEINS

```
    1                    2                                          3  3'
    ▼                    ▼                                          ▼  ▼
  1 MNPNNRSEHD TIKTTENNEV PTNHVQYPLA ETPNPTLEDL NYKEFLRMTA
           4
           ▼
 51 DNNTEALDSS TTKDVIQKGI SVVGDLLGVV GFPFGGALVS FYTNFLNTIW

101 PSEDPWKAFM EQVEALMDQK IADYAKNKAL AELQGLQNNV EDYVSALSSW

151 QKNPVSSRNP HSQGRIRELF SQAESHFRNS MPSFAISGYE VLFLTTYAQA

201 ANTHLFLLKD AQIYGEEWGY EKEDIAEFYK RQLKLTQEYT DHCVKWYNVG

251 LDKLRGSSYE SWVNFNRYRR EMTLTVLDLI ALFPLYDVRL YPKEVKTELT
```

N-TERMINI OF THE UNIQUE B.t.t. PROTEINS PRODUCED IN EITHER B.t.t. AND/OR E. COLi WERE DETERMINED BY AMINO ACID SEQUENCING. THE ARROWS AND ASSOCIATED NUMBERS CORRESPOND TO THE FIRST AMINO ACID OF THE PROTEINS DESCRIBED IN FIG. 6.

FIG.7

```
            PstI                         HpaI      EcoRI
   NcoI  /           EcoRI        \     EcoRV /  XmnI      BglII   HindIII
   |    /             |            \     /  /     |          |       |
   |___/_____|_____/__/_____|_____|_____|
   START       pMON 9759 = Tox+                      STOP
```

```
                                            BglII  HindIII
                                              |      |
   |_____|_____|
            pMON 5438 = Tox⁻
                                           ___|_____|___
                                          |              |
                                                S
                                          AMN    BnX
                                          1ah    guh
                                          uee    13o
                                          111    2A2
                                           /     //
            GGAACAATCCCAGTGTTTAGTAGGTAGCTAGCCAGATCTTTATTT
            ---------+---------+---------+---------+------
            CCTTGTTAGGGTCACAAATCATCCATCGATCGGTCTAGAAATAAA
             G T I P V F S R - L A R S L F
                        490
```

```
                                            BglII  HindIII
                                              |      |
   |_____|_____|
            pMON 5441 = Tox⁻
                                           ___|_____|___
                                          |              |
                                                S
                                          AMN    BnX
                                          1ah    guh
                                          uee    13o
                                          111    2A2
                                           /     //
            TTACAGGCGGAGATTAGTAGGTAGCTAGCCAGATCTTTATTTTC
            ---------+---------+---------+---------+----
            AATGTCCGCCTCTAATCATCCATCGATCGGTCTAGAAATAAAAG
             T G G D - - V A S Q I F I F
                        536
```

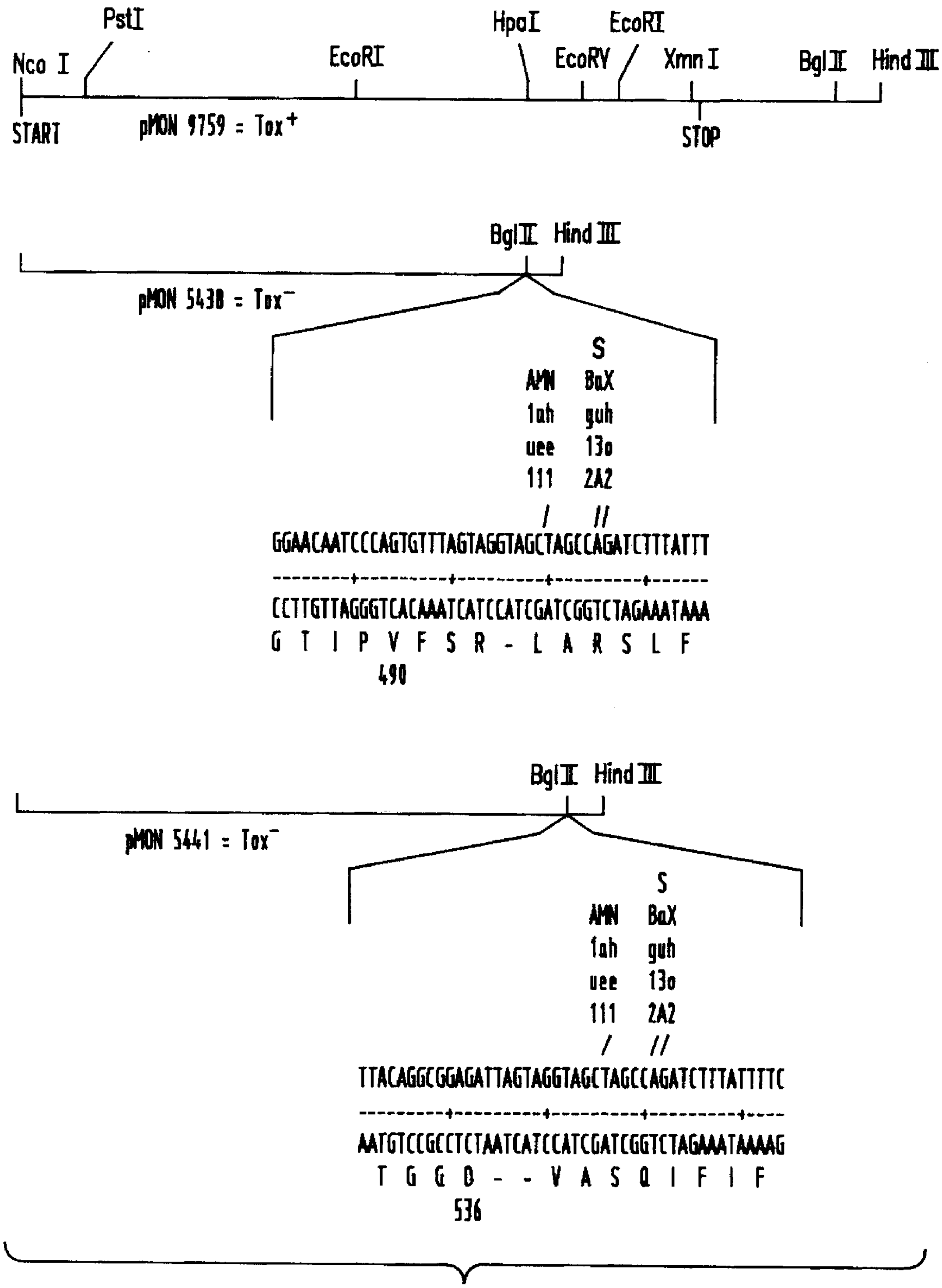

FIG.8A

```
                                          BglII  HindIII
pMON 5449 = Tox⁻
                                                    S
                                 D      M      AvrN   BaX
                                 d      a      1ah    guh
                                 e      e      uee    13a
                                 1      1      111    2A2
                                                /      //
              CTCAGTTTAGACGGGGCTAGTAGGTAGCTAGCCAGATCTTTATTT
              --------+---------+---------+---------+-----
              GAGTCAAATCTGCCCCGATCATCCATCGATCGGTCTAGAAATAAA
              L  S  L  D  G  A  S  R  -  L  A  R  S  L  F
                                582
```

```
                                          BglII  HindIII
pMON 5448 = Tox⁻
                                                    S
                                        AvrN    BaX
                                        1ah     guh
                                        uee     13a
                                        111     2A2
                                          /      //
              GTTTATATAGACAAAATTGAATTTAGTAGGTAGCTAGCCAGATCTTTATTT
              --------+---------+---------+---------+----------+-
              CAAATATATCTGTTTTAACTTAAATCATCCATCGATCGGTCTAGAAATAAA
              V  Y  I  D  K  I  E  F  S  R  -  L  A  R  S  L  F
                                      640
```

THE INSERTS SHOW THE ACTUAL AMINO ACID
SEQUENCE OF THE ALTERED B.t.t. PROTEINS.

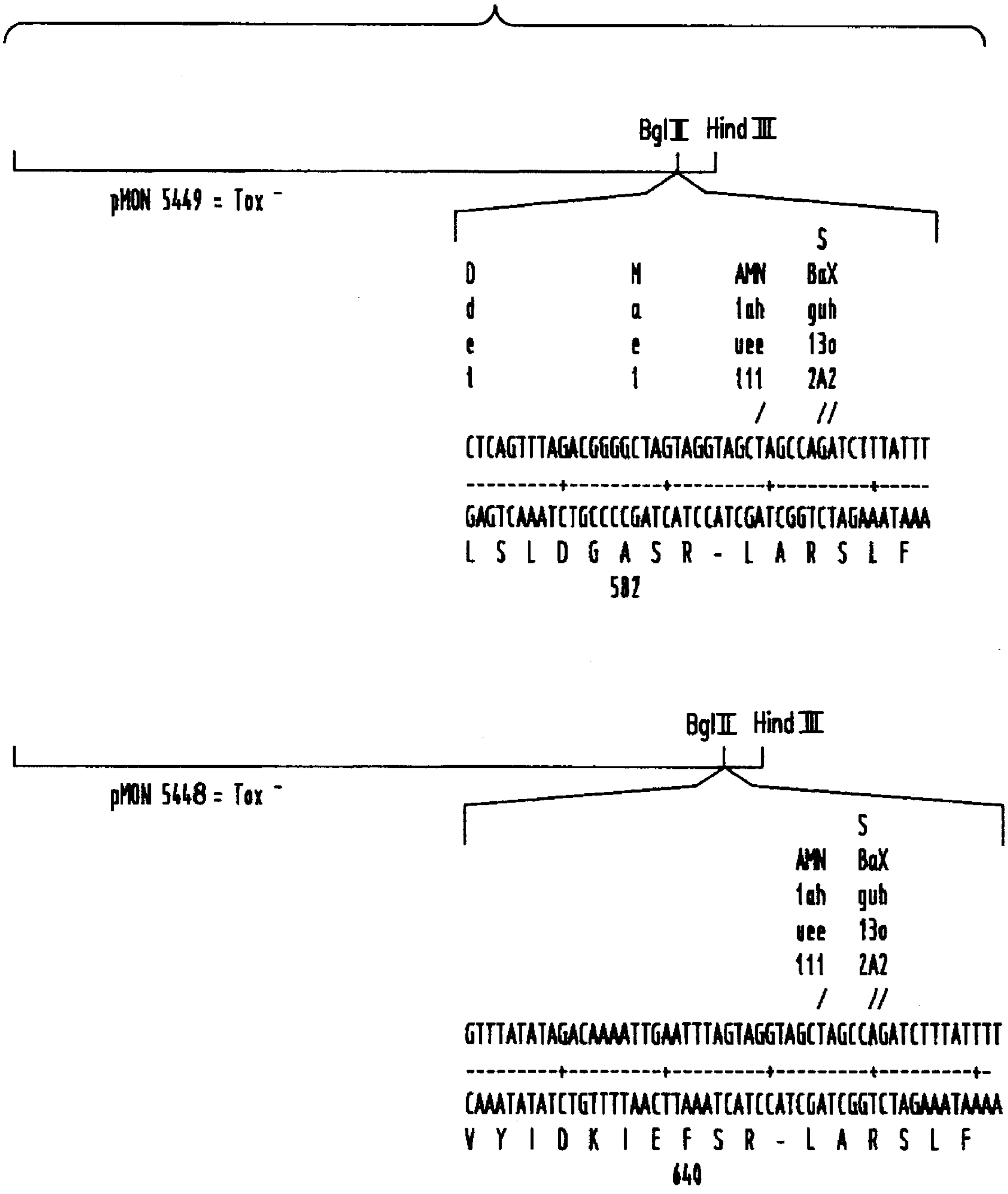

FIG.8B

```
                PstI                    HpaI      EcoRI
 NcoI  /              EcoRI       /  EcoRV  /  XmnI         BglII    HindIII
 |-----/--------------|-----------|---/-----|---/-----------|--------|
 START                              pMON 9759 = Tox⁺    STOP
```

```
       PstI
 NcoI  |
 |-----|----------------------------------------------------|
                              pMON 5460 = Tox⁺
```

```
              M   P
              e   s
              t   t
              2   1
 TATAAAGAGTTTTTAAGAATAACTGCAGATAATAATA
 ------+---------+---------+---------+
 ATATTTCTCAAAAATTCTTATTGACGTCTATTATTAT
   Y K E F L R I T A D N N T
                        48
```

```
 NcoI
 |-----------------------------------------------------|
                          pMON 5456 = Tox⁺
```

```
  NS  N M       F         M       A
  ct  l b       o         a       l
  oy  a o       k         e       u
  11  3 2       1         1       1
  /
  CCATGGATGCAGATAATAATACGGAAGCACTAGATAGCTCT
  -+---------+---------+---------+---------
  GGTACCTACGTCTATTATTATGCCTTCGTGATCTATCGAGA
    M D A D N N T E A L D S S
    48
```

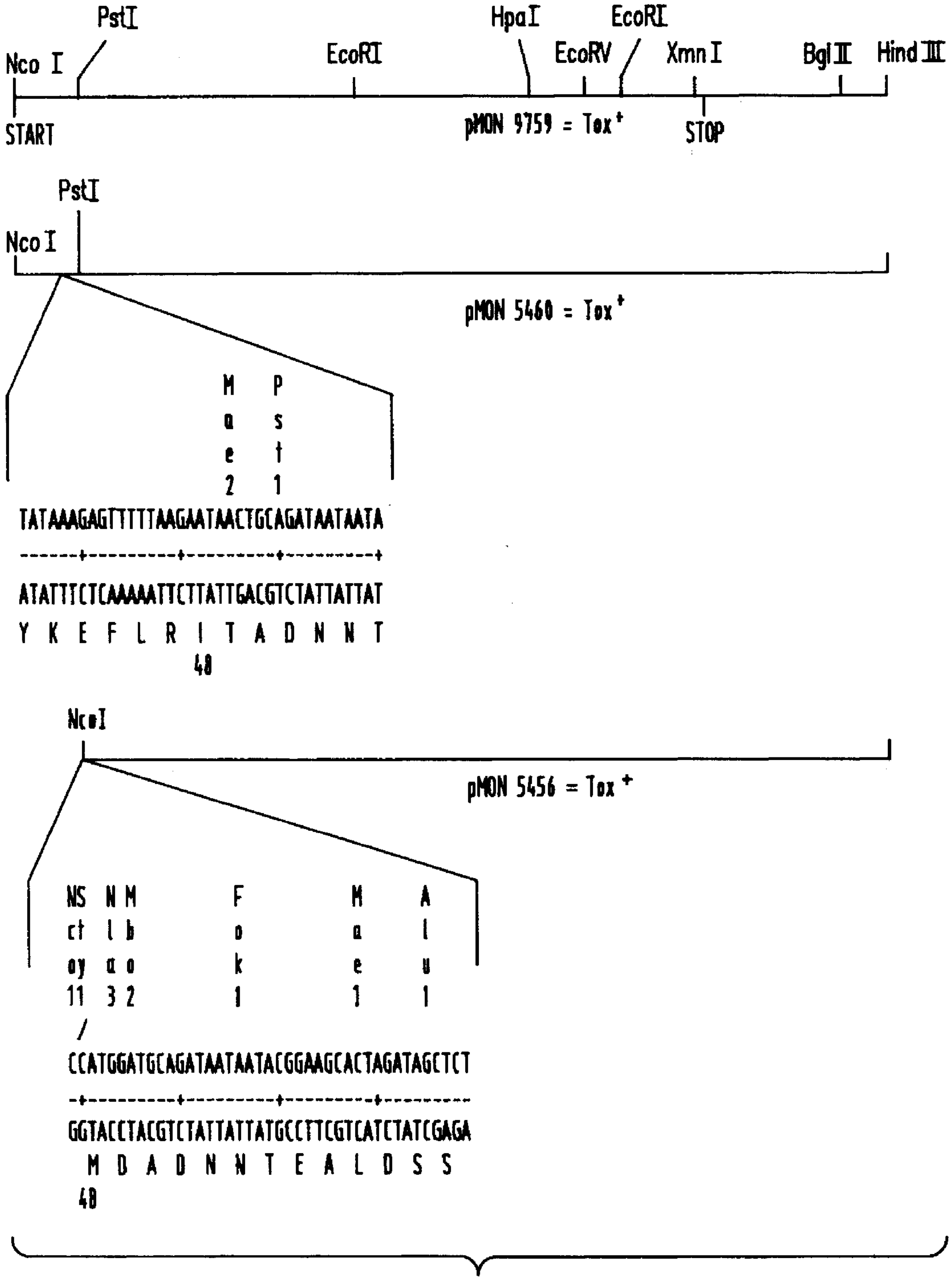

FIG.9A

```
       (StyI)
                            pMON 5452 = Tox +

NNN            HH
       lab            ha
       aeo            ae
       312            12
       CCATGCTAGGAGTAGTAGGTTTCCCGTTTGTGGAGCGCTTG
       -+---------+---------+---------+---------
       GGTACGATCCTCATCATCCAAAGGGCAAACACCTCGCGAAC
        M L G V V G F P P V E R L
          77
```

```
       NcoI
                            pMON 5467 = Tox -

NS   N
       ct   l
       oy   a
       11   3
       /
       CCATGGCAATTTGGCCAAGTGAAGAC
       ---------+----------------
       GGTACCGTTAAACCGGTTCACTTCTG
        M A I W P S E D
          99
```

THE INSERTS SHOW THE ACTUAL AMINO ACID
SEQUENCE OF THE ALTERED B.t.t. PROTEINS.

SUMMARY OF N-TERMINUS AND C-TERMINUS TRUNCATIONS OF THE B.t.t. TOXIN

1 MDPNNRSEHD TIKTTENNEV PTNHVQYPLA ETPNPTLEDL NYKEFLRMTA

▲5456+

51 DNNTEALDSS TTKDVIQKGI SVVGDLLGVV GFPFGGALVS FYTNFLNTIW

▲ 5452+ ▲ 5467-

101 PSEDPWKAFM EQVEALMDQK IADYAKNKAL AELQGLQNNV EDYVSALSSW

151 QKNPVSSRNP HSQGRIRELF SQAESHFRNS MPSFAISGYE VLFLTTYAQA

201 ANTHLFLLKD AQIYGEEWGY EKEDIAEFYK RQLKLTQEYT DHCVKWYNVG

251 LDKLRGSSYE SWVNFNRYRR EMTLTVLDLI ALFPLYDVRL YPKEVKTELT

301 RDVLTDPIVG VNNLRGYGTT FSNIENYIRK PHLFDYLHRI QFHTRFQPGY

351 YGNDSFNYWS GNYVSTRPSI GSNDIITSPF YGNKSSEPVQ NLEFNGEKVY

401 RAVANTNLAV WPSAVYSGVT KVEFSQYNDQ TDEASTQTYD SKRNVGAVSW

451 DSIDQLPPET TDEPLEKGYS HQLNYVMCFL MQGSRGTIPV LTWTHKSVDF

▲5438-

501 FNMIDSKKIT QLPLVKAYKL QSGASVVAGP RFTGGDIIQC TENGSAATIY

▲ 5441-

551 VTPDVSYSQK YRARIHYAST SQITFTLSLD GAPFNQYYFD KTINKGDTLT

▲ 5449-

601 YNSFNLASFS TPFELSGNNL QIGVTGLSAG DKVYIDKIEF IPVN

T- DNA REGION IN AGROBACTERIUM ACO

DNA SEQUENCE FOR THE ENHANCED CaMV35S PROMOTER
USED IN THE PREPARATION OF pMON893

```
                                *
5' -AAGCTTGCAT GCCTGCAGGT CCGATG[TGAG ACTTTTCAAC AAAGGGTAAT    50

    ATCCGGAAAC CTCCTCGGAT TCCATTGCCC AGCTATCTGT CACTTTATTG   100

    TGAAGATAGT GGAAAAGGAA GGTGGCTCCT ACAAATGCCA TCATTGCGAT   150

    AAAGGAAAGG CCATCGTTGA AGATGCCTCT GCCGACAGTG GTCCCAAAGA   200

    TGGACCCCCA CCCACGAGGA GCATCGTGGA AAAAGAAGAC GTTCCAACCA   250

    CGTCTTCAAA GCAAGTGGAT TGATGTGAT]G GTCCGATG[TG AGACTTTTCA   300

    ACAAAGGGTA ATATCCGGAA ACCTCCTCGG ATTCCATTGC CCAGCTATCT   350

    GTCACTTTAT TGTGAAGATA GTGGAAAAGG AAGGTGGCTC CTACAAATGC   400

    CATCATTGCG ATAAAGGAAA GGCCATCGTT GAAGATGCCT CTGCCGACAG   450

    TGGTCCCAAA GATGGACCCC CACCCACGAG GAGCATCGTG GAAAAAGAAG   500

    ACGTTCCAAC CACGTCTTCA AAGCAAGTGG ATTGATGTGA T]ATCTCCACT   550

    GACGTAAGGG ATGACGCACA ATCCCACTAT CCTTCGCAAG ACCCTTCCTC   600

    TATATAAGGA AGTTCATTTC ATTTGGAGAG GACACGCTGA CAAGCTGACT   650

    CTAGCAGATC T - 3'                                        661
```

* BRACKETED SEQUENCE INDICATED DUPLICATED ENHANCER SEQUENCE

FIG.18

INSECT-RESISTANT PLANTS COMPRISING A *BACILLUS THURINGIENSIS* GENE

This is a continuation of application Ser. No. 08/759,446 filed Dec. 5, 1996, issued as U.S. Pat. No. 5,763,241, which is is a continuation of U.S. application Ser. No. 08/435,101, filed May 4, 1995, now abandoned, which is a divisional of U.S. application Ser. No. 08/072,281, filed Jun. 4, 1993, issued as U.S. Pat. No. 5,495,071, which is a continuation of U.S. application Ser. No. 07/523,284, filed May 14, 1990, now abandoned, which is a continuation of U.S. application Ser. No. 07/044,081, filed Apr. 29, 1987, now abandoned.

The present invention relates to the fields of genetic engineering, biochemistry and plant transformation. More particularly, the present invention is directed toward transformation of plant cells to express a chimeric gene encoding a protein toxic to Coleopteran insects.

BACKGROUND OF THE INVENTION

*Bacillus thuringiensis* (*B.t.*) is a spore forming soil bacterium which is known for its ability to produce a parasporal crystal protein which is toxic to a wide variety of insects. Most strains are active against Lepidopteran insects (moths and butterflies) and a few are reported to have activity against Dipteran insects (mosquitoes and flies, see Aronson et al. 1986). Toxin genes from a variety of these strains have been cloned and the toxins have been expressed in heterologous hosts (Schnepf et al., 1981; Klier et al., 1982). In recent years, *B.t.* var. *tenebrionis* (*B.t.t.*, Krieg et al., 1983; Krieg et al., 1984) and *B.t.* var. *san diego* (*B.t.sd.*, Herrnstadt et al., 1986) strains have been identified as having activity against Coleopteran insects. The toxin gene from *B.t.sd.* has been cloned, but the toxin produced in *E. coli* was reported to be a larger size than the toxin from *B.t.sd.* crystals, and activity of this recombinant *B.t.sd.* toxin was implied to be weak.

Insects susceptible to the action of the protein toxin of Coleopteran-type *Bacillus thuringiensis* bacteria include, but are not limited to, Colorado potato beetle (*Leptinotarsa decemlineata*), boll weevil (*Anthonomus grandis*), yellow mealworm (*Tenebrio molitor*), elm leaf beetle (*Pyrrhalta luteola*) and Southern corn rootworm (*Diabrotica undecimpunctata howardi*).

Therefore, the potential for genetically engineered plants which exhibit toxicity or tolerance toward Coleopteran insects was foreseen if such plants could be transformed to express a Coleopteran-type toxin at a insecticidally-effective level. Agronomically important crops which are affected by Coleopteran insects include alfalfa, cotton, maize, potato, rape (canola), rice, tobacco, tomato, sugar beet and sunflower.

BRIEF SUMMARY OF THE INVENTION

Although certain chimeric genes have been expressed in transformed plant cells and plants, such expression is by no means straight forward. Specifically, the expression of Lepidopteran-type *B.t.* toxin proteins has been particularly problematic. It has now been found that the teachings of the art with respect to expression of Lepidopteran-type *B.t.* toxin protein in plants do not extend to Coleopteran-type *B.t.* toxin protein. These findings are directly contrary to the prior teachings which suggested that one would employ the same genetic manipulations to obtain useful expression of such toxins in transformed plants.

In accordance with one aspect of the present invention, there has been provided a method for producing genetically transformed plants which exhibit toxicity toward Coleopteran insects, comprising the steps of:

(a) inserting into the genome of a plant cell susceptible to attack by Coleopteran insects a chimeric gene comprising:
  i) a promoter which functions in plant cells to cause production of RNA;
  ii) a DNA sequence that causes the production of a RNA sequence encoding a Coleopteran-type toxin protein of *Bacillus thuringiensis*; and
  iii) a 3' non-translated DNA sequence which functions in plant cells to cause the addition of polyadenylate nucleotides to the 3' end of the RNA sequence;
(b) obtaining transformed plant cells, and
(c) regenerating from the transformed plant cells genetically transformed plants exhibiting resistance to Coleopteran insects.

In accordance with another aspect of the present invention, there has been provided a chimeric plant gene comprising in sequence:

(a) a promoter which functions in plant cells to cause the production of RNA;
(b) a DNA sequence that causes the production of a RNA sequence encoding a Coleopteran-type toxin protein of *Bacillus thuringiensis*; and
(c) a 3' non-translated region which functions in plant cells to cause the addition of polyadenylate nucleotides to the 3' end of the RNA sequence.

There has also been provided, in accordance with another aspect of the present invention, bacterial cells, transformed plant cells and plant transformation vectors that contain, respectively, DNA comprised of the above-mentioned elements (a), (b) and (c).

In accordance with yet another aspect of the present invention, a differentiated plant has been provided that comprises transformed plant cells, as described above, which exhibit toxicity to Coleopteran insects. The present invention also contemplates seeds which produce the above-described transformed plants.

BRIEF DESCRIPTION OF THE DRAWINGS

FIG. 1 shows the DNA probes (SEQ ID NOS:4–8) used for isolation of the *B.t.t.* toxin gene.

FIGS. 5A–5M show the DNA sequence and location of restriction sites for the 1932 bp ORF (SEQ ID NO:1) of the *B.t.t.* gene encoding the 644 amino acid toxin protein (SEQ ID NO:2).

FIG. 6 shows the bands observed for *B.t.t.* toxin following SDS-PAGE analysis.

FIG. 7 shows the N-termini of proteins expressed from the *B.t.t.* toxin gene or proteolytically produced in vivo in *B.t.t.* (SEQ ID NO:2, amino acids 1–300).

FIGS. 8A–8B represent the altered *B.t.t.* genes used to analyze the criticality of the C-terminal portion of the toxin.

FIGS. 9A–9B represent the altered *B.t.t.* genes used to analyze the criticality of the N-terminal portion of the toxin.

FIG. 10 shows the deletions produced in evaluation of *B.t.t.* toxin protein mutants (SEQ ID NO:2).

FIG. 18 shows the DNA sequence for the enhanced CaMV35S promoter (SEQ ID NO:33).

DETAILED DESCRIPTION OF THE INVENTION

Figure 2:
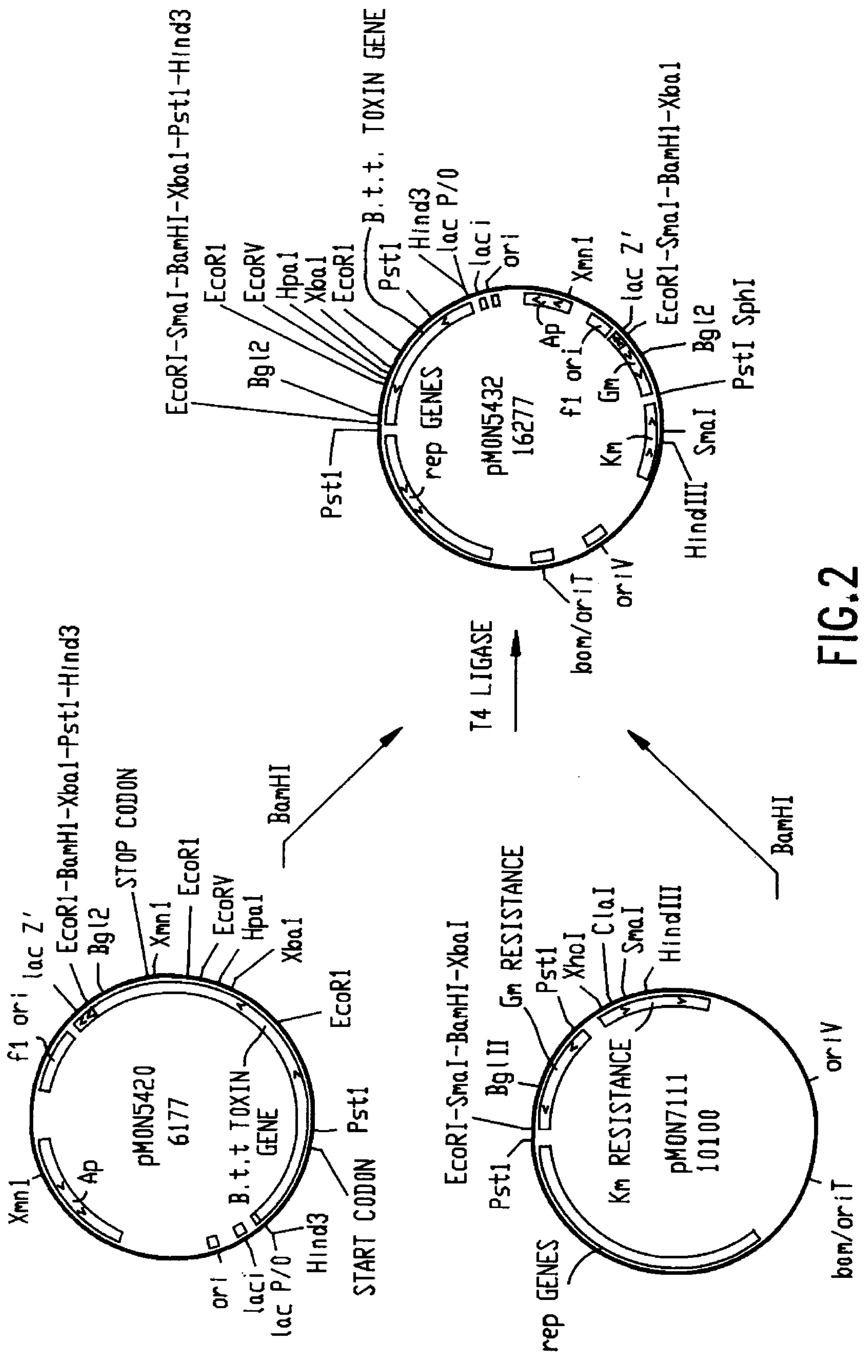
FIG. 2 shows the steps employed in the preparation of plasmid pMON5432.

The present invention provides a method for transforming plants to exhibit toxicity toward susceptible Coleopteran insects. More particularly, the present invention provides transgenic plants which express the Coleopteran-type toxin protein of *Bacillus thuringiensis* at an insecticidal level.

In one aspect, the present invention comprises chimeric genes which function in plants and produce transgenic plants which exhibit toxicity toward susceptible Coleopteran insects. The expression of a plant gene which exists as double-stranded DNA involves the transcription of one strand of the DNA by RNA polymerase to produce messenger RNA (mRNA), and processing of the mRNA primary transcript inside the nucleus. This processing involves a 3' non-translated region which adds polyadenylate nucleotides to the 3' end of the mRNA.

Transcription of DNA to produce mRNA is regulated by a region of DNA usually referred to as the "promoter." The promoter region contains a sequence of nucleotides which signals RNA polymerase to associate with the DNA, and initiate the production of a mRNA transcript using the DNA strand downstream from the promoter as a template to make a corresponding strand of RNA.

A number of promoters which are active in plant cells have been described in the literature. These include the nopaline synthase (NOS), octopine synthase (OCS) and mannopine synthase (MAS) promoters which are carried on tumor-inducing plasmids of *Agrobacterium tumefaciens*, the cauliflower mosaic virus (CaMV) 19S and 35S promoters, and the light-inducible promoter from the small subunit of ribulose bis-phosphate carboxylase (ssRUBISCO, a very abundant plant polypeptide). These types of promoters have been used to create various types of DNA constructs which have been expressed in plants; see e.g., PCT publication WO 84/02913 (Rogers et al., Monsanto).

Promoters which are known or are found to cause production of a mRNA transcript in plant cells can be used in the present invention. Suitable promoters may include both those which are derived from a gene which is naturally expressed in plants and synthetic promoter sequences which may include redundant or heterologous enhancer sequences. The promoter selected should be capable of causing sufficient expression to result in the production of an effective amount of toxin protein to render the plant toxic to Coleopteran insects. Those skilled in the art recognize that the amount of toxin protein needed to induce the desired toxicity may vary with the particular Coleopteran insects to be protected against. Accordingly, while the CaMV35S, ssRUBISCO and MAS promoters are preferred, it should be understood that these promoters may not be optimal promoters for all embodiments of the present invention.

The mRNA produced by the chimeric gene also contains a 5' non-translated leader sequence. This sequence may be derived from the particular promoter selected such as the CaMV35S, ssRUBISCO or MAS promoters. The 5 non-translated region may also be obtained from other suitable eukaryotic genes or a synthetic gene sequence. Those skilled in the art recognize that the requisite functionality of the 5' non-translated leader sequence is the enhancement of the binding of the mRNA transcript to the ribosomes of the plant cell to enhance translation of the mRNA in production of the encoded protein.

The chimeric gene also contains a structural coding sequence which encodes the Coleopteran-type toxin protein of *Bacillus thuringiensis* or an insecticidally-active fragment thereof. Exemplary sources of such structural coding sequences are *B.t. tenebronis* and *B. t. san diego*. Accordingly, in exemplary embodiments the present invention provides a structural coding sequence from *Bacillus thuringiensis* var. *tenebrionis* and insecticidally-active fragments thereof. Those skilled in the art will recognize that other structural coding sequence substantially homologous to the toxin coding sequence of *B.t.t.* can be utilized following the teachings described herein and are, therefore, within the scope of this invention.

The 3' non-translated region contains a polyadenylation signal which functions in plants to cause the addition of polyadenylate nucleotides to the 3' end of the RNA. Examples of suitable 3' regions are (1) the 3' transcribed, non-translated regions containing the polyadenylate signal of the tumor-inducing (Ti) plasmid genes of Agrobacterium, such as the nopaline synthase (NOS) gene, and (2) plant genes like the soybean storage protein genes and the ssRUBSICO. An example of preferred 3' regions are those from the NOS, ssRUBISCO and storage protein genes, described in greater detail in the examples below.

The Coleopteran-type toxin protein genes of the present invention are inserted into the genome of a plant by any suitable method. Suitable plant transformation vectors include those derived from a Ti plasmid of *Agrobacterium tumefaciens* such as those described in, e.g. EPO publication 131,620 (Rogers et al.), Herrera-Estrella 1983, Bevan 1983, Klee 1985 and EPO publication 120,516 (Schilperoort et al.). In addition to plant transformation vectors derived from the Ti or root-inducing (Ri) plasmids of Agrobacterium, alternative methods can be used to insert the Coleopteran-type toxin protein genes of this invention into plant cells. Such methods may involve, for example, liposomes, electroporation, chemicals which increase free DNA uptake, and the use of viruses or pollen as vectors. If desired, more than one gene may be inserted into the chromosomes of a plant, by methods such as repeating the transformation and selection cycle more than once.

The plant material thus modified can be assayed, for example, by Northern blotting, for the presence of Coleopteran-type toxin protein mRNA. If no toxin protein mRNA (or too low a titer) is detected, the promoter used in the chimeric gene construct is replaced with another, potentially stronger promoter and the altered construct retested. Alternately, level of toxin protein may be assayed by immunoassay such as Western blot. In many cases the most sensitive assay for toxin protein is insect bioassay.

This monitoring can be effected in whole regenerated plants. In any event, when adequate production of toxin protein mRNA is achieved, and the transformed cells (or protoplasts) have been regenerated into whole plants, the latter are screened for resistance to attack by Coleopteran insects. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers), Malvaceae (cotton, etc.), Chenopodiaceae (sugar beet, etc.) and various floral crops. See e.g. Ammirato et al. (1984).

All protein structures represented in the present specification and claims are shown in conventional format wherein the amino group at the N-terminus appears to the left and the carboxyl group at the C-terminus at the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y) and valine (Val;V).

ISOLATION OF *B.t.t.* TOXIN GENE

The *B.t.t.* gene encoding the Coleopterantype toxin protein was isolated as described below.

Isolation of Protein Crystals

*B.t. tenebrionis* was grown in Trypticase Soybroth (TSB) medium for the isolation of protein crystals. In attempting to isolate intact crystals from *B.t.t.* a significant difference between these crystals and those of the Lepidopteran-type was noted. While Lepidopteran-type crystals are routinely isolated on gradients formed from Renografin, Hypaque or NaBr, it was found that *B.t.t.* crystals dissolved in these gradients media. It was found that *B.t.t.* crystals were stable in gradients of sucrose, and sucrose gradients were used for the isolation of *B.t.t.* crystals.

Isolation of *B.t.t.* Toxin from Crystals

Purified crystals were analyzed for their protein composition by SDS polyacrylamide gel electrophoresis. Results of these experiments indicated that *B.t.t.* crystals contained at least two protein components with molecular weights of approximately 68 to 70 kilodaltons (kDa) and approximately 60 kDa, respectively. The relative amounts of the components were variable from preparation to preparation. In addition, it was suggested that the higher molecular weight component might consist of more than a single protein. Bernhard (1986) reported proteins of about 68 kDa and 50 kDa as components of *B.t.t.* crystals. Herrnstadt et al. (1986) reported that the crystals of *B.t. san diego* were composed of a protein of about 64 kDa. In contrast, Lepidopteran-type *B.t.* strains such as *B.t. kurstaki* typically contain a higher molecular weight protein of 130 kDa to 140 kDa. This result indicates a significant difference in the structure of the Lepidopteran and Coleopteran toxin proteins.

Several approaches were taken to purifying the individual protein components of the crystal. Isoelectric focusing was not successful because all of the protein precipitated. Anion exchange high pressure liguid chromatograph (HPLC) on a Mono Q column failed to resolve the components. Cation exchange HPLC on a Mono S column in the presence of 4 M urea resolved five peaks. Analysis of the peaks by SDS gel electrophoresis indicated that peak A contained only the higher molecular weight band from whole crystals. Peak B was rich in this higher band with small amounts of the lower band. Peak C was rich in the lower band with significant amounts of the upper band. Peaks D and E were mixtures of both bands. In most preparations the higher molecular weight band, corresponding to peaks A and B, was the predominant protein in the crystals. For the HPLC separated material, peaks A and B represented most of the recovered protein.

The N-terminal amino acid sequences corresponding to peaks A, B, and C were determined. Peaks A and B were found to have the same N-terminal sequence while the peak C sequence was different. The sequences determined were:

Peak A and B (SEQ ID NO:2, amino acids 1–15)

```
1               5                   10
Met Asn Pro Asn Asn Arg Ser Glu His Asp Thr

            15
Ile Lys Thr Thr
```

Peak C (SEQ ID NO:34)

```
1           5                   10
Met X Pro X Thr Arg Ala Leu Asp Asp Thr Ile

        15  16
Lys Lys Asp Val Ile Glyn Lys
```

X represents an undeterminent amino acid.

Insect Toxicity of *B.t.t.* Proteins

Several preparations of *B.t.t.* and *B.t.t.* proteins were tested for toxicity to various insects including both Lepidopterans and Coleopterans. No activity was observed towards Lepidopterans (corn earworm, black cutworm, tobacco hornworm and cabbage looper). Among the Coleopterans, activity was observed against Colorado potato beetle (*Leptinotarsa decemlineata*) and boll weevil (*Anthonomus grandis*). Lower level activity was exhibited against Southern corn rootworm (*Diabrotica undecimpunctata howardi*). Insecticidal activity was found in crude bacterial cultures, purified crystals, solubilized crystals and isolated peaks C, D, E (pooled), A and B.

Assays for toxicity to Colorado potato beetle were carried out by applying the preparation to be tested to tomato leaves and allowing the insects to feed on the treated leaves for four days. Assays with boll weevil and Southern corn rootworm were performed by incorporating the test material in an appropriate diet mixture.

IDENTIFICATION AND CLONING OF THE *B.t.t.* TOXIN GENE IN *E. COLI* AND PSEUDOMONAS

Using this N-terminal protein sequence information, synthetic DNA probes (FIG. 1) were designed which were used in the isolation of clones containing the *B.t.t.* toxin gene. Probes were end-labeled with [$\gamma$-$^{32}$P] ATP according to Maniatis (1982). *B. thuringiensis* var. *tenebrionis* was grown for 6 hours at 37° C. in Spizizen medium (Spizizen, 1958) supplemented with 0.1% yeast extract and 0.1% glucose (SPY) for isolation of total DNA. Total DNA was isolated from *B.t.t.* by the method of Kronstad (1983). Cells were grown on Luria agar plates for isolation of *B.t.t.* crystals used in toxicity studies.

*E. coli* and Pseudomonas cultures were routinely grown in Luria Broth (LB) with ampicillin (Ap, 200 μg/ml), kanamycin (Km, 50 μg/ml), or gentamicin (Gm, 15 μg/ml) added for plasmid selection and maintenance.

Isolation and Manipulation of DNA

Plasmid DNA was extracted from *E. coli* and Pseudomonas cells by the method of Birnboim and Doly (1979) and large quantities were purified using NACS-52 resin (Bethesda Research Laboratories) according to manufacturer's instructions. Restriction endonucleases, calf alkaline phosphatase and T4 DNA ligase were used according to manufacturer's instructions (New England Biolabs). Restriction digestion products were analyzed on 0.8% agarose gels electrophoresed in Tris-acetate buffer. DNA fragments for cloning were purified from agarose using the freeze-thaw method. Construction of recombinant DNA molecules was according to Maniatis et al. (1982). Transformation into *E. coli* were performed according to Maniatis (1982).

Cloning of the *B.t.t.* Toxin Gene

Southern analysis (Southern, 1975) was performed using the modified dried gel procedure (Conner et al., 1983). Colony filter hybridization, for detection of *B.t.t.* toxin clones, used the tetra-methylammonium chloride method (Wood et al., 1985).

Figure 3:
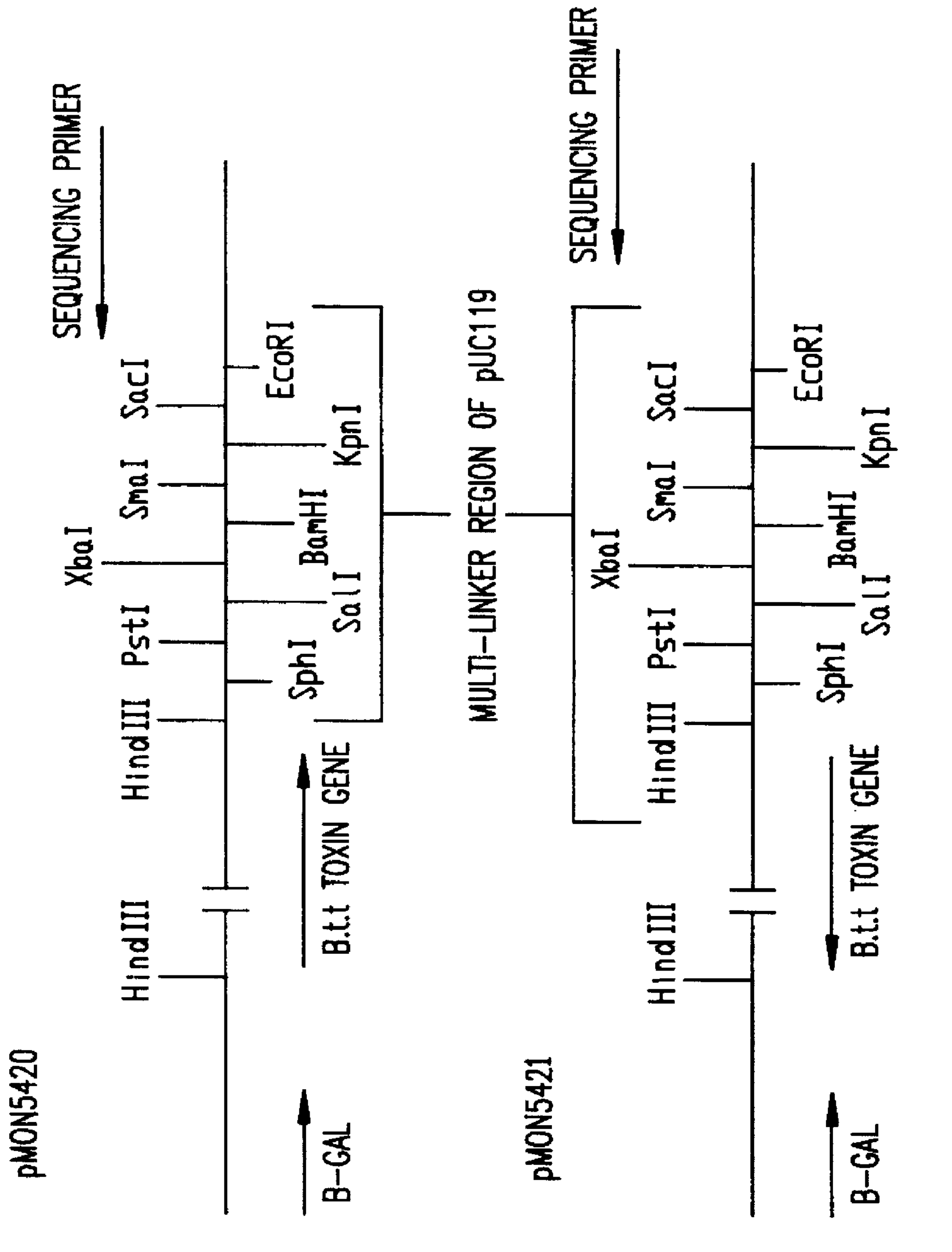
FIG. 3 shows the orientation of the 3.0 kb HindIII fragment encoding the toxin gene in pMON5420 and pMON5421 with respect to the multilinker of pUC119.

Southern analysis of BamHI and HindIII digested *B.t.t.* total DNA identified a 5.8 kb BamHI and a 3.0 kb HindIII fragment which hybridized to the synthetic A1 probe. BamHI fragments of *B.t.t.* DNA (5.4–6.5 kb) were purified from agarose gels and ligated to alkaline phosphatase treated BamHI digested pUC119. pUC119 is prepared by isolating the 476 bp HgiAI/DraI fragment of bacteriophage M13 and making the ends of the fragment blunt with T4 DNA polymerase (New England Biolabs). This fragment is then inserted into pUC19 that has been digested with NdeI and filled with Klenow DNA polymerase (New England Biolabs). The ligated *B.t.t.* and pUC119 DNA was then used to transform *E. coli* JM101 cells. After several attempts only 150 Ap resistant colonies were obtained. HindIII fragments of *B.t.t.* DNA (2.8–3.5 kb) were also cloned into the HindIII site of pUC119, and 1100 colonies were obtained. All colonies were screened by colony hybridization to the Al probe (FIG. 1). Eleven HindIII clones showed strong hybridization, but none of the BamHI colonies showed any hybridization. The colonies identified by hybridization to A1 were then screened using synthetic probe A2 (FIG. 1) and two colonies showed hybridization to the second probe. Restriction digest patterns of the two colonies indicated that the same 3.0 kb HindIII fragment was contained in both but in opposite orientations. These clones were designated pMON5420 and pMON5421 (FIG. 3). To confirm that the clones did contain the gene for the *B.t.t.* toxin protein, the single stranded DNA from both clones was sequenced using degenerate probes A1 and A2 as primers for di-deoxy sequencing (Sanger, 1977). Sequence analysis with A1 probe as primer revealed an open reading frame (ORF) whose sequence was identical to amino acids 9 through 15 of the amino acid sequence determined for purified peaks A and B of the *B.t.t.* toxin protein. Probe A2 produced DNA sequence which began beyond the end of the determined amino sequence, but this DNA sequence was identical to sequence produced with Al. These results confirm that the desired *B.t.t.* toxin gene was cloned.

Southern hybridization to total *B.t.t.* DNA using degenerate probes based on the N-terminus of peak C failed to detect specific bands suggesting that the amino acid sequence determined for peak C was incorrect or most probably was obtained from a mixture of two or more proteins comprising peak C.

Analysis of Proteins Produced in *E. coli*

*B.t.t.* crystal proteins and recombinant *B.t.t.* proteins were examined by SDS-PAGE (Laemmli, 1970). One ml of *E. coli* was centrifuged, the pellets resuspended in 100 μg SDS-sample buffer and 10 μl samples were electrophoresed on 7.5% polyacrylamide gels. The gels were either stained with Coomassie Blue or probed for cross reactivity to antibodies raised against purified *B.t.t.* toxin crystals. Western Blots were performed using the horseradish peroxidase conjugated antibody procedure (Towbin et al., 1984). High molecular weight markers were purchased from BioRad.

Further confirmation that the clones produced *B.t.t.* toxin was obtained by Western blot analysis of the proteins produced in *E. coli. E. coli* JM101 cells containing either pUC119, pMON5420 or pMON5421 were grown overnight in the presence of IPTG (0.1 mM) to induce the lac promoter. Duplicate samples were analyzed by SDS-PAGE along with purified *B.t.t.* crystal proteins included as controls. Western blot analysis of one gel revealed the production of 2 cross reacting proteins by *E. coli* containing pMON5420 or pMON5421. These proteins were identical in size to the major and minor proteins of the *B.t.t.* crystal. Molecular weights of the proteins were determined by comparison to the molecular weight standards on the second gel stained with Coomassie blue. The major toxin protein was determined to be 74 kDa in size and the minor toxin protein was determined to be 68 kDa in size. The level of *B.t.t.* toxin proteins produced by pMON5420 was increased by the addition of IPTG while production of toxin proteins by pMON5421 was unaffected.

Production of *B.t.t.* Toxin(s) in *Pseudomonas fluorescens*

A broad host range vector, pMON5432, was constructed by cloning BamHI digested pMON5420 into the BamHI site of pMON7111 as shown in FIG. 2. This vector was then mated into *P. fluorescens* 701E1 for analysis of toxin production. Tri-parental matings into *Pseudomonas fluorescens* were done as previously described (Ditta et al., 1980). Samples of overnight cultures, grown with and without IPTG, were prepared for Western blot analysis and insect toxicity studies. The proteins produced by Pseudomonas were identical in size to the *E. coli* produced proteins and protein expression was increased with the addition of IPTG.

Insect Toxicity Assay

Coleopteran toxin activity was assayed using newly hatched Colorado potato beetle (*Leptinotarsa decemlineata*) insects in a tomato leaf feeding assay. *E. coli* and Pseudomonas cultures were grown overnight in the presence of IPTG, centrifuged and resuspended at various concentrations in 10 mM $MgSO_4$. The cells were disrupted by sonication (three 15 sec. pulsed treatments on ice). Tween-20 (0.1%) was added and the sample painted onto a tomato leaf placed into a 9 cm petri dish lined with moist filter paper. Ten Colorado potato beetle larvae were added to each leaf. After four days, the percentage corrected mortality (percentage of insects alive in the control minus the percentage of insects alive in the treated sample divided by the percentage alive in the control) was computed using Abbott's formula (Abbott, 1925). Assays were performed in duplicate and the data combined. *B.t.t.* crystal/spore preparation were used as positive controls.

*E. coli* cultures of pMON5420 and pMON5421 were evaluated for Coleopteran toxicity using different concentrations of cultures grown with added IPTG. A comparison of recombinant and wild type *B.t.t.* toxin activities is shown below in Table I. The results show that the recombinant B.t.t. protein(s) are toxic to Colorado potato beetle. The 2×-concentrated, IPTG-induced pMON5420 culture killed 100% of the insects as did the *B.t.t.* spore/crystal control. These toxicity results demonstrate that the *B.t.t.* gene cloned was the gene that encodes the *B.t.t.* toxin protein.

Insect feeding assay showed that the Pseudomonas produced toxins were toxic to Colorado potato beetle. The relative toxicity of Pseudomonas cultures was consistent with the amount of toxin protein produced as determined by Western blot analysis when compared to *E. coli* cultures.

TABLE I

Coleopteran Toxicity of Recombinant B.t.t. Toxin

| Sample[1] | Concentration[2] | Corrected Mortality |
|---|---|---|
| *E. coli* JM101 | | |
| pUC119 | 2× | 0% |
| pMON5420 | 1× | 83% |
| pMON5420 | 2× | 100% |
| pMON5421 | 1× | 44% |
| pMON5421 | 2× | 61% |
| *P. fluorescens* 701E1 | | |
| pMON5432 | 3× | 60% |
| B.t.t. prep | | 100% |

[1]Cultures were grown overnight with added IPTG, concentrated, sonicated and tested for toxicity.
[2]1× equals cellular concentration of overnight culture.

SEQUENCE OF TOXIN GENE OF *B.t.t.*

Figure 4:
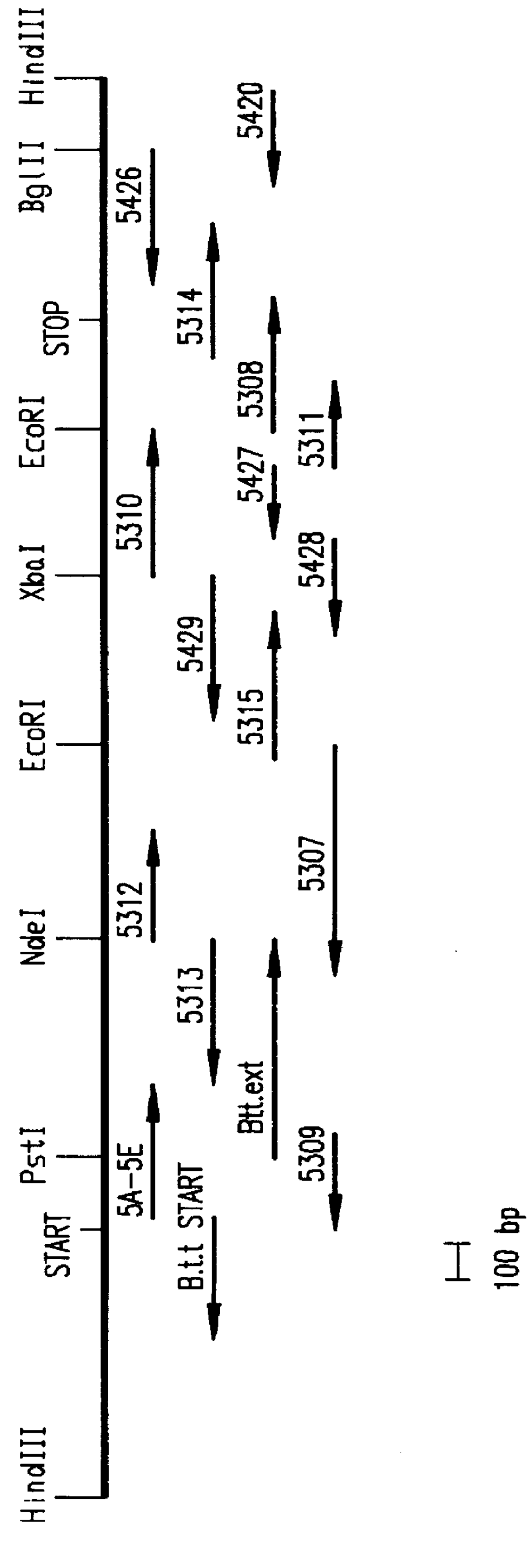
FIG. 4 shows the strategy utilized for sequencing of the *B.t.t.* toxin gene contained in pMON5420 and pMON5421.

Location and orientation of the *B.t.t.* gene within the cloned fragment was determined based on the following information: a) DNA sequence was obtained from the single stranded pMON5421 template, b) A PstI site identified, by DNA sequence analysis, near the start of translation was mapped in pMON5420 and pMON5421, c) several other restriction sites were mapped, d) a deletion from a BglII site to a BamHI site which deletes 130 bp was constructed and both full-length proteins were produced. This information was used to construct maps of pMON5420 and pMON5421. Referring to FIG. 4, the toxin coding region begins 500 bp from the 5' HindIII site, and 150 bp upstream of the PstI site. The coding region ends approximately 450 bp from the 3' HindIII site. The BglII site is approximately 350 bp downstream of the stop codon.

Plasmids

The plasmids generated for sequencing the *B.t.t.* insecticidal toxin gene are listed in Table II. The parental plasmids, pMON5420 and pMON5421, are independent isolates of the HindIII fragment cloned into pUC119 in opposite orientation.

TABLE II

Sequencing Plasmids

| | |
|---|---|
| pMON5420 | 3.0 HindIII insert from B.t.t. DNA (parent plasmid) |
| pMON5421 | 3.0 HindIII insert from B.t.t. DNA (parent plasmid) |
| pMON5307 | EcoRI deletion of pMON5420 |
| pMON5308 | EcoRI deletion of pMON5421 |
| pMON5309 | PstI deletion of pMON5420 |
| pMON5310 | XbaI deletion of pMON5421 |
| pMON5311 | EcoRV-SmaI deletion of pMON5421 |
| pMON5312 | NdeI-BamHI deletion of pMON5421* |
| pMON5313 | NdeI-BamHI deletion of pMON5420* |
| pMON5314 | AsuII-BamHI deletion of pMON5421* |
| pMON5315 | AsuII(partial)-BamHI deletion of pMON5421* |
| pMON5316 | AsuII-BamHI deletion of PMON5421** |
| pMON5426 | BglII-BamHI deletion of pMON5420 |
| pMON5427 | EcoRV-SmaI deletion of pMON5420 |
| pMON5428 | HpaI-SmaI deletion of pMON5420 |
| pMON5429 | XbaI deletion of pMON5420 |

*After digestion of the DNA with both enzymes, the ends were filled in with Klenow polymerase, ligated and used to transform JM101.
**Generation of the AsuII-BamHI deletion of this construct resulted in a rearrangement of an AsuII fragment to an orientation opposite to its original location. This resulted in a sequence of 5316 reading toward the $NH_2$ end.

Preparation of Single Stranded Template for Sequencing

The following protocol provides reproducibly good yields of single stranded template for sequencing. A single colony containing the pUC119 with the fragment to be sequenced was streaked on L-agar (10 g tryptone, 5 g yeast extract, 5 g Nacl, and 15 g agar per liter) containing ampicillin (200 $\mu$g per ml). A single colony from this plate was inoculated into 3 ml of L-broth (200 $\mu$g per ml ampicillin) and incubated at 37° C. overnight with shaking. From this culture, 50 $\mu$l was inoculated into 10 ml of 2×YT (20 g tryptone and 10 g yeast extract per liter) with 200 $\mu$g of ampicillin per ml in a 150 ml side arm flask and incubated at 37° C. with shaking. After 2–3 hours (Klett reading of 50), 100 $\mu$l of M13K07 (helper phage) grown in *E. coli* JMl0l was added to induce the culture. The flask was shaken for one hour followed by the addition of 20 ml of 2×YT adjusting the final concentration of kanamycin to 70$\mu$g per ml and ampicillin to 200 $\mu$g per ml. The cultures were shaken for 16–18 hours at 37° C. A total of three mls of the induced overnight culture was found to be sufficient to isolate a suitable amount of template for four sequencing experiments. The three mls were spun in 1.5 ml eppendorf tubes for 1 minute, decanted and filtered through a 0.2 um Gel-man Sciences Acrodisc®. This step was found to be useful for the removal of cellular debris and intact *E. coli*. A polyethylene glycol precipitation (20% PEG, 2.5M NaCl, 500 $\mu$l per 2 ml of lysate) at room temperature for 10 minutes was followed by centrifugation for 10 minutes. The supernatant was discarded followed by a brief spin (15 seconds) and removal of the residual PEG. Any remaining PEG will be carried through the template isolation and adversely affect DNA sequencing reactions. The pellets are resuspended in 100 $\mu$l of TE (10 mM Tris, 1 mM EDTA, pH 8.0), combined and mixed well with 200 $\mu$l of buffered phenol (buffered by equilibration with an equal volume of 1M Tris-HCl, pH 8.0, then 0.1M Tris-HCl, pH 8.0, followed by an equal volume of TE). After incubation at 55° C. for 10 minutes an equal volume (200 $\mu$l) of phenol/chloroform (1::1) was added, vortexed, and centrifuged for 2 minutes. The top layer was removed, extracted with 200 $\mu$l of chloroform, centrifuged and the aqueous phase removed. The single stranded template was precipitated with 25 $\mu$l of 3M sodium acetate (pH 5.2) and 600 $\mu$l of 95% ethanol, incubated on dry ice for 5 minutes and centrifuged for 10 minutes. The precipitate was resuspended in 25 $\mu$l of $H_2O$ and 2 $\mu$l was checked on an agarose gel for correct size, relative concentration and contaminating DNA.

Sequencing Reagents and Conditions

The protocols for DNA sequencing are described in detail in the Handbook available from Amersham Corporation. Reagents (nucleotides, primer, buffer, chase solution and Klenow polymerase) were obtained from the Amersham M13 sequencing kit (catalog #N4502). The sequencing mixes provided in the Amersham kit were adjusted for efficient sequencing of the A-T rich *B.t.t.* gene. Instead of the recommended 1::1 mix of dNTP to ddNTP, the following ratios were found to be more appropriate; 40 $\mu$l dATP: 10 $\mu$l ddATP, 35 $\mu$l dTTP: 15 $\mu$l ddTTP, 15 $\mu$l dGTP: 35 $\mu$l ddGTP, and 10 $\mu$l dCTP: 40 $\mu$l ddCTP. Radioactive sulfur ([$\alpha$-$^{35}$S] dATP) was used in the sequencing reactions (Amersham catalog #SJ.1304). The sequencing gels (prepared as described in the Amersham handbook) were run on the Hoeffer "Poker Face" apparatus at 70 watts (1200–1400 volts) which was found to give very good resolution. Higher voltages resulted in fuzzy bands.

Sequencing of the *B.t.t.* Toxin Gene

The isolated plasmids, pMON5420 and pMON5421, contained a 3.0 HindIII fragment in opposite orientation (see FIG. 3). The major protein of the *B.t.t.* crystal, which was used as the basis for design of the oligonucleotide probes, has a molecular weight estimated to be 73–76 kdal corresponding to approximately 2.0 kb of DNA. Initial sequencing from the A1 and A2 primers (synthetic oligonucleotides based on the amino acid sequence of Peak A; see Table III, below) confirmed that the DNA sequence corresponded to the anticipated amino acid sequence.

TABLE III

Synthetic oligonucleotides Used for Sequencing the B.t.t. Insecticidal Toxin Gene

| Primer (SEQ ID NO:35) | Template | Sequence | Location[1] |
|---|---|---|---|
| Bttstart Ms C[5] | pMON5420 | tgaacatggttagttgg | 291–275 |
| Bttext Ms C6 | pMON5421 | taggtgatctctaggcg | 422–439 |
| Bttseq Ms C7 | pMON5421 | ggaacaaccttctctaatat | 1156–1175 |
| BttA1 Ms C7* | pMON5421 | atgaayccnaayaaycg | 205–222 |
| BttA2 Ms C8* | pMON5421 | garcaygayacyathaa | 227–242 |

*y =t or c. r = a or g. h = t, c or a. n = a, g, c or t.
[1]The location of the primers is based on the total of 2615 bases sequenced. Sequencing from pMON5420 proceeded toward the amino acid end and from pMON5421 toward the carboxyl end (see FIG. 3).

A PstI site was located in the initial sequence which was used to identify the location and probable orientation of the *B.t.t.* gene within pMON5420 and pMON5421 (see FIGS. 3 and 4). Mapping of restriction sites with a number of enzymes (HpaI, XbaI, NdeI, EcoRV, and BglII) and the numerous unique sites remaining in the pUC119 portion of both pMON5420 and pMON5421 provided the opportunity to obtain sequence using the universal sequencing primer. Deletions were generated in both pMON5420 and pMON5421 bringing the universal primer homologous region in close proximity to internal regions of the gene. In areas not easily sequenced by generating deletions, synthetic oligonucleotides corresponding to sequenced regions in the coding sequence (Table III) were used as primers to obtain extensions of the sequenced regions. The regions sequenced (sequence coordinates; Table IV) and the direction of sequencing is depicted in FIG. 4.

TABLE IV

Source of Sequence Data

| Plasmid | Length (bp) | Location | Plasmid | Length (bp) | Location |
|---|---|---|---|---|---|
| pMON5307 | 414 | 797–1211 | pMON5316 | 153 | 1861–2041 |
| pMON5308 | 276 | 1895–2171 | pMON5426 | 300 | 2220–2520 |
| pMON5309 | 170 | 114–284 | pMON5427 | 110 | 1701–1812 |
| pMON5310 | 283 | 1595–1880 | pMON5428 | 129 | 1548–1677 |
| pMON5311 | 110 | 1812–1922 | pMON5429 | 303 | 1292–1595 |
| pMON5312 | 248 | 782–1030 | Bttstart | 264 | 1–264 |
| pMON5314 | 291 | 2041–2305 | Bttext | 380 | 440–820 |
| pMON5315 | 330 | 1157–1187 | BttA2 | 267 | 250–517 |

COMPUTER ANALYSIS OF THE *B.t.t.* INSECTICIDAL TOXIN GENE

A total of 2615 base pairs of sequence were obtained from pMON5420 and pMON5421. Computer analysis of the sequence revealed a single open reading frame from base pair 205 to 2136. Referring to FIG. 5, the *B.t.t.* insecticidal toxin gene is 1932 base pairs, coding for protein of 644 amino acids with a molecular weight of 73,091 daltons. The protein has a net charge of -17 and a G-C content of 34%.

Comparison Between Coleopteran-type and Lepidopteran-type Toxin Genes and Proteins Although the Coleopteran-type toxins and the Lepidopteran-type toxins are derived from *Bacillus thuringiensis*, there are significant differences between the toxin genes and the toxin proteins of the two types. As isolated from *Bacillus thuringiensis* both types of toxins are found in parasporal crystals; however, as described above, the solubility properties of the crystals are distinctly different. In addition, the sizes of the toxin proteins found in solubilized crystals are completely different. Lepidopteran-type toxin proteins are typically on the order of 130 kDa while the Coleopteran-type toxin proteins are approximately 70 kDa.

Isolation and DNA sequence analysis of the Coleopteran-type toxin gene from *B.t. tenebrionis* predicts the amino acid sequence of the toxin protein (see FIG. 5). Both the nucleotide sequence and the derived amino acid sequence of the Coleopteran-type toxin gene have been compared to nucleotide and amino acid sequence of a typical Lepidopteran-type toxin. This comparison was performed using the computer program BESTFIT of Devereux et al (1984) which employs the algorithm of Smith and Waterman (1981). BESTFIT obtains maximum alignment of two nucleotide or amino acid sequences. BESTFIT calculates two parameters, quality and ratio, which can be used as alignment metrics when comparing different alignments. Ratio varies between 0 and 1.0. A larger ratio indicates a better alignment (greater similarity) between two sequences.

The BESTFIT alignment shows that the two types of toxin genes are related at both the nucleotide sequence and amino acid sequence level. However, the alignment also shows that the two sequences are clearly distinct and possess many regions of mismatch at both the nucleotide and amino acid sequence levels. For example, the ratio for comparison of the two amino acid sequences is only 0.22. At the nucleotide sequence level, maximum alignment is obtained only by the introduction of many gaps in both sequences, and the ratio is only 0.072.

There are many sequenced examples of Leptidopteran-type toxin genes; similar comparison among these genes has shown that the gene from *B.t. kurstaki* HD-1 described by Schnepf et al. (1985) and that from *B.t. kurstaki* HD-73 described by Adang et al. (1985) represent the two most divergent Lepidopteran-type toxin genes. By comparison with the ratios calculated above for alignment of the Colepteran-type and the Lepidopteran-type gene, the ratio for amino acid sequence comparison of the two most divergent Lepidopteran-type proteins is 0.811, and the ratio for these two Lepidopteran-type genes at the nucleotide sequence level is 0.755. This indicates that although the Coleopteran-type and Lepidopteran-type toxin genes may be evolutionarily related, they are quite distinct in both nucleotide and amino acid sequence.

HIGH LEVEL PRODUCTION OF RECOMBINANT *B.t.t.* TOXIN IN *E. COLI*

To facilitate purification of large quantities of recombinant *B.t.t.* toxin, it was necessary to clone the *B.t.t.* gene into an *E. coli* high expression vectors. Site directed mutagenesis was used to introduce an NcoI restriction site into pMON5420 at the ATG codon at the start of the open reading frame.

Site Directed Mutagenesis

Site-directed mutagenesis to introduce new restriction sites was performed by the method of Kunkel (1985). Plasmid pMON5420 was introduced by transformation into *E. coli* strain BW313, which contains the $dut^-$ and $ung^-$ mutations in order to incorporate deoxyuridine into the DNA. A single transformed colony was grown overnight in 2×YT medium containing 100 μg/ml ampicillin and 0.25 μg/ml uridine. A 0.5 ml aliquot of this culture was added to 10 ml of the same medium and incubated for one hour at 37° C. with vigorous shaking to a density of 0.23 (A600). To induce formation of single strand containing phage particles, helper phage M13K07 was added at a multiplicity of approximately 10 and incubation was continued for one hour to a density of 0.4 (A600). The culture was diluted by addition of 30 ml of the above medium, and kanamycin was added to a final concentration of 70 μg/ml. Incubation was continued for 15 hours at which point cells were removed by centrifugation. Phage particles were precipitated from 25 ml of supernatant by addition of 5 ml of 20% PEG/2.5 M NaCl/50 μg/ml RNAase A followed by incubation on ice for 15 minutes. Phage were recovered by centrifugation and dissolved in 0.8 ml TE buffer. DNA was isolated from the particles by three extractions with 0.8 ml phenol/chloroform/isoamyl alcohol (25:24:1) followed by ethanol precipitation. The DNA pellet was dissolved in 100 μl of water to a final concentration of approximately 1 mg/ml (estimated by agarose gel electrophoresis).

Synthetic oligonucleotide primers for mutagenesis were suspended in water at a concentration of approximately 10 pmole/μl. The oligonucleotides were phosphorylated utilizing T4 polynucleotide kinase in a reaction containing 50 pmoles oligonucleotide, 1 mM ATP, 25 mM Tris-Cl pH 8, 10 mM $MgCl_2$, 0.2 mM spermidine-HCl, 1 mM DTT and 2 units of enzyme. The reaction was incubated at 37° C. for 30 minutes and then heated at 70° C. for 5 minutes. The phosphorylated primer was annealed to the deoxyuridine containing phage DNA by mixing approximately 1 pmole of the phage DNA (2 μg) with 10 pmole primer in a reaction containing 6.6 mM Tris-HCl, 6.6 mM $MgCl_2$, 6.6 mM NaCl and 5 mM DTT. The mixture was heated to 70° C. for seven minutes and then slowly cooled to room temperature. The annealed primer/template was used as the substrate for synthesis of double-stranded, closed circular DNA by addition of each dNTP to 0.5 mM, ATP to 0.5 mM, 5 units of Klenow fragment DNA polymerase and 400 units T4 DNA ligase (New England Biolabs). The reaction was carried out in the same buffer salts as for annealing at 15° C. for approximately 15 hours. At this time an additional 400 units of ligase was added and incubation was continued for two hours.

One half of the reaction was used to transform 0.15 ml of $CaCl_2$-treated JM101 cells, and the cells were spread on LB plates containing 100 μg/ml ampicillin. Between 30 and several hundred colonies were recovered for each mutagenesis reaction. Single colonies were grown overnight in LB containing ampicillin and plasmid minipreps were prepared by the alkaline SDS method. Plasmids were analyzed for the presence of the new restriction site and the presence of the site was confirmed by sequence analysis as described above.

A plasmid containing a NcoI site (pMON9759) at the start of the *B.t.t.* insecticidal toxin gene was generated by site-specific mutagenesis. The primer used is shown below:

| Desired Site | Primer (SEQ ID NO:40) |
| --- | --- |
| NcoI | GATTGTTCGGATCCATGGTTCTTCCTCCCT |

Figure 16:
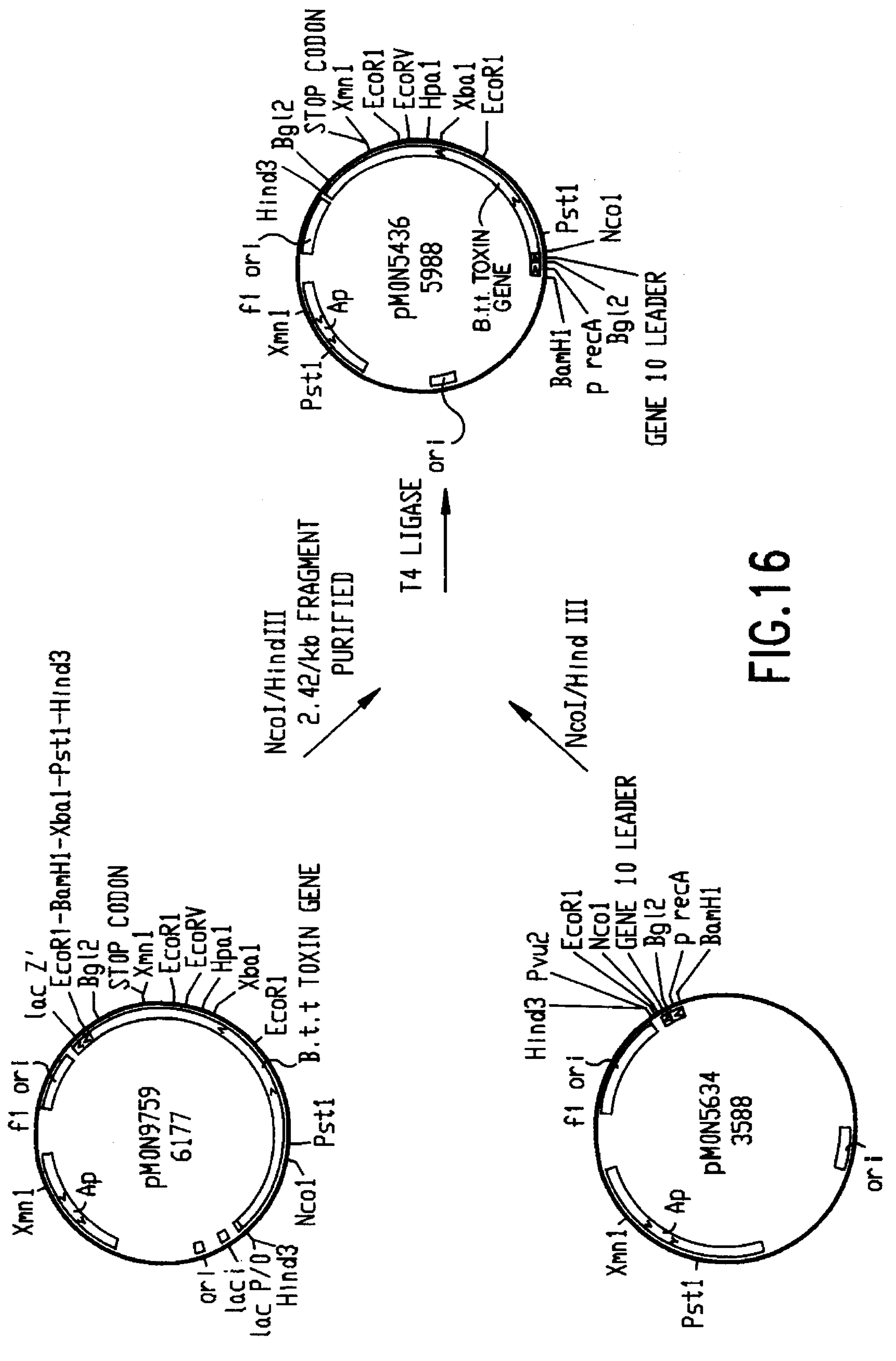
FIG. 16 shows the steps employed in the preparation of plasmid pMON5436.

The generation of the NcoI site at the N-terminus has changed the second amino acid from asparagine to aspartic acid. This change does not affect insect toxicity. BamHI and StyI sites have also been generated as a consequence of the introduction of this NcoI site. The plasmid containing the NcoI site has been designated pMON9759. The 2.5 kb NcoI-HindIII fragment containing the toxin encoding segment from pMON9759 was then cloned into NcoI-HindIII digested pMON5634 to produce pMON5436. Referring to FIG. 16, pMON5634 is a pBR327 based plasmid which also contains the fl phage origin of replication. The vector contains a synthetic recA promoter which is induced by nalidixic acid. The gene 10 leader from phage T7 (described in commonly assigned U.S. patent application Ser. No. 005821, filed Feb. 4, 1987, the disclosure of which is hereby incorporated by reference) is also present to increase expression in *E. coli*. A synthetic linker with multiple cloning sites was added for insertion of genes downstream of the promoter and gene 10 leader sequence.

For induction of the recA promoter, overnight cultures were diluted 1:50 into M9 minimal media (Miller, 1972) with 0.2% casamino acids and 0.25% glucose added. At 150 Klett units, naladixic acid was added to 50μg/ml and cells were harvested 3 hours post induction. The level of *B.t.t.* toxin produced by nalidixic acid induced pMON5436 was compared to IPTG induced pMON5420 by analysis on SDS-PAGE. The Coomassie blue stained gel revealed no detectable *B.t.t.* produced by pMON5420 while the level of *B.t.t.* produced by pMON5436 was approximately 5% of total protein. This construct was used to isolate large quantities of the recombinant *B.t.t.* toxin proteins to investigate toxicity levels, insect specificity, and mode of action.

*B.t.t.* TOXIN CHARACTERIZATION

Identification of the Number and Origin of the *B.t.t.* Proteins

*B.t.* var. *tenebrionis* produces a number of Coleopteran-type toxin proteins, present in protein crystals, which are produced co-incidentally with sporulation (see FIG. 6). These protein crystals are released into the media as cells autolyse during or following sporulation. To determine the number of toxin proteins produced by *B. t.* var. *tenebrionis,* 500 ml cultures of this organism were grown in 2 liter flasks in 15% TSB medium in 100 mM 2-(N-morpholino) ethanesulfonic acid (MES) buffer, pH 7.0 at 30° C. for 7 days. At this point the cultures have sporulated and the cells lysed. Protein crystals and spores were harvested by centrifugation at 20,000×gravity (g) for 20 min. at 4° C. Pellets were washed three times with excess water, followed by three washes with 2 M NaCl. The resultant pellet was stored at 4° C. in water plus 0.02% sodium azide. *B.t.t.* toxin protein was solubilized from the crystals by suspending the pellet in 100 mM sodium carbonate buffer, pH 10 and stirring this suspension for two hours at room temperature. After centrifugation 20,000×g for 20 min to remove unsolubilized materials, the supernatant was filtered through a 0.2 μm filter to remove any remaining spores. *B.t.t.* toxin protein prepared in this manner, as do crystals solubilized in 125 mM Tris-HCl, 4% SDS, 20% glycerol and 10% 2-mercaptoethanol, pH 6.8, (SDS sample buffer used to prepare samples for SDS-PAGE analysis) is comprised of four major and different proteins as judged by SDS-PAGE analysis. Five unique products were identified by N-terminal amino acid analysis. To determine whether all five of these proteins were derived from the same gene or whether two or more genes are required for their synthesis, the N-terminal amino acid sequence of each of these proteins were determined using automatic Edman degradation chemistry.

An Applied Biosystems, Inc. Model 470A gas phase sequencer (Foster City, Calif.) was employed (Hunkapiller, et al., 1983). The respective PTH-amino acid derivatives were identified by RP-HPLC analysis in an on-line fashion employing an Applied Biosystems, Inc. Model 120A PTH analysis fitted with a Brownlee 2.1 mm I.D. PTH-C18 column. Determination of the N-terminal amino acid sequence of each protein will establish whether all these proteins were derived from the *B.t.t.* toxin gene described above.

The strategy to sequence these proteins was to sequence the *B.t.t.* toxin proteins corresponding to bands 1 and 3 (see FIG. 6) from the *E. coli* clone JM101 (pMON5436), bands 2, 3 and 4 by electro-elution of the proteins produced by *B.t.* var. *tenebrionis* from SDS-PAGE gels. The sequence of *B.t.t.* 1 and 3 was determined with proteins purified from JM101 (pMON5436). JM101 (pMON5436), as well as the other *E. coli* constructs (pMON5450, 5456 and 5460, infra) produces the *B.t.t.* in the form of insoluble refractile bodies after cultures are induced for high level expression. The *E. coli* constructs were grown in modified M9 media at 37° C. A culture grown overnight was used to inoculate 400 ml of the modified M9 media in 2.4 1 fernbach flasks to an initial starting density of 10 Klett units. Nalidixic acid, in 0.1 N NaOH, was added to the cultures at 100 Klett units to a final concentration of 50 μg/ml, to induce *B.t.t.* toxin protein expression. After an additional 4 hours of incubation, cultures were harvested by centrifugation at 20,000×g for 20 min. at 4° C. Cell pellets were suspended in water to a density equivalent to 5000 Klett units per ml and sonicated in an ice bath with a Heat Systems Ultrasonics sonicator at a power of 9, 50% duty cycle for a total of 5 min. The sonicated preparation was centrifuged for 20 min. at 20,000×g at 4° C. Pellets, containing refractile bodies and cell debris, were washed twice with cold water and suspended at 10,000 Klett unit equivalents per ml in water plus 25% sulfolane. After stirring at room temperature for 2 hours, the solubilized refractile body preparations were centrifuged again at 20,000×g at 4° C. to remove unsolubilized materials. Tris-HCl was added to the supernatant to a final concentration of 50 mM, pH 7.6. The *B.t.t.* bands 1 and 3 were co-purified on an HR5/5 MonoQ ion exchange column using a 75 to 200 mM Nacl gradient in 50 mM Tris-HCl, 25% sulfolane, pH 7.6. Fractions containing *B.t.t.* bands 1 and 3 were identified by 9% SDS-PAGE analysis, pooled, dialyzed into 100 mM sodium carbonate, pH 10 buffer and concentrated in Amicon centricon concentrators. *B.t.t.* toxin protein corresponding to band 3 was purified from JM101 (pMON5456) in an analogous manner.

Bands corresponding to 2 alone and bands 3,3' and 4 (see FIG. 6) combined were electroeluted from 7% SDS-PAGE slab gels which were run with 48 μg of *B.t.t.* crystals solubilized in 100 mM sodium carbonate, 20 mM dithiotheitol (DTT), pH 10 buffer. Gels were stained for 10 min in Coomassie blue R250 and destained in 50% methanol, 10% acidic acid for 20 min. Appropriate bands were excised with a razor blade and the *B.t.t.* protein electro-eluted. Knowing the amino acid sequence, deduced from the DNA sequence of the *B.t.t.* toxin gene cloned in *E. coli*, all five N-termini of these unique proteins were identified (FIG. 7).

Proteins corresponding to band 1 and 3 originated from two independent translational initiation events which start at the methionine at positions 1 and 48 (FIGS. 6 and 7), respectively. Proteins corresponding to *B.t.t.* bands 2, 3 and 4, observed only in *B.t.* var. *tenebrionis* and not in the *E. coli* constructs, apparently arise from proteolytic cleavage of either bands 1 or 3. These results establish that all five proteins originate from the same gene.

Purification of *B.t.t.* Bands 1 and 3 for Insect Toxicity Testing

The *B.t.t.* proteins produced in *E. coli* corresponding to bands 3 and 1 plus 3 which were solubilized in 25% sulfolane and purified by MonoQ chromatography for N-terminal amino acid sequence analysis showed no insect toxicity against Colorado potato beetle insects. In subsequent experiments, it was demonstrated that sulfolane itself inactivates *B.t.t.* Therefore, an alternative purification method was developed and used to compare the relative insecticidal toxicities of *B.t.t.* bands 1 and 3 produced in *E. coli* compared to the *B.t.t.* solubilized from native crystals of *B.t.* var. *tenebrionis.* Cultures were grown, induced, harvested and refractile bodies isolated as described above. The various *B.t.t.* proteins were solubilized from the refractile bodies using 100 mM sodium carbonate, pH 10. The solubilized *B.t.t.* toxin, concentrated using Amicon stirred cells with YM-10 membranes, was purified on a Pharmacia Superose-12, gel filtration FPLC column, which separates *B.t.t.* bands 1 and 3 and from other contaminating proteins. Appropriate fractions, based upon SDS-PAGE analysis, were pooled, concentrated and used for insect toxicity experiments with the Colorado potato beetle insects. Proteins corresponding to band 1 (pMON5436, band 1 (pMON5460) and band 3 (pMON5456) were greater than 90% pure based upon SDS-PAGE analysis. Band 1 produced by pMON5460 has isoleucine at amino acid 48 in place of methionine (see below).

To obtain native protein toxin from *B. t.* var. *tenebrionis* for toxicity comparisons, native crystals were isolated and purified using sucrose gradient centrifugation as described above. Crystals were solubilized in 100 mM sodium carbonate, 20 mM DTT, pH 10 and used for insect toxicity tests.

All *B.t.t.* toxin protein preparations and controls for insect assay contained 0.3% Tween 20, a surfactant which enhances the ability of these solutions to bind to tomato leaves. Insect toxicity experiments were performed by thoroughly painting the upper and lower surfaces of 3 to 4 week old detached tomato leaves with buffer solutions containing the designated *B.t.t.* proteins at the indicated protein concentrations. After the solutions were air dried on the surface of the tomato leaves, a single leaf and 10 Colorado potato beetle insects were placed in a petri dish and incubated at 22° C. for 4 days. The number of dead insects was determined and the toxicity results expressed as % corrected mortality (%CM); according to Abbott's formula described above. All experiments were performed in duplicate and all but the *B.t.t.* band 1 from pMON5460 were repeated on different days. The results of these tests are shown in the table below.

TABLE V

Toxicity of B.t.t. Proteins Against Colorado Potato Beetle

| Sample | Concentration (ug/ml) | Corrected Mortality (%) |
|---|---|---|
| B.t.t. Solubilized | 100 | 100 |
| | 20 | 70 |
| | 4 | 10 |
| Purified Band 1 | 100 | 87 |
| (pMON5436) | 20 | 68 |
| | 10 | 34 |
| Purified Band 1 | 100 | 67 |
| (pMON5460) | 20 | 72 |
| | 10 | 44 |
| Purified Band 3 | 100 | 91 |
| (pMON5456) | 20 | 64 |
| | 10 | 32 |

Relative toxicity of purified proteins from different *E. coli* constructs were compared to solubilized native B.t.t. crystals. Band 1 (pMON5436) and Band 3 (pMON5456) were purified as described. Band 1 (pMON5460) was purified using gel filtration chromato-graphy. Native B.t.t. crystals were solubilized in 100 mM $Na_2CO_3$, pH 10.

The amounts of *B.t.t.* toxin required to kill 50% of the Colorado potato beetle insects were essentially identical for *B.t.t.* band 1 isolated from pMON5436 and pMON5460 and *B.t.t.* band 3 isolated from pMON5456 (Table V). Likewise, all of these purified *B.t.t.* preparations from *E. coli* demonstrated toxicities essentially identical to that observed with the sodium carbonate solubilized native toxin from *B.t.* var. *tenebrionis.*

DETERMINATION OF TOXIC FRAGMENTS OF *B.t.t.* TOXIN PROTEINS

Several groups (Schnepf et al. 1985, Hofte et al. 1986, and Wabiko et al. 1986) have reported that C-terminal truncations of the Lepidopteran-type toxins do not reduce toxicity (of the 1155 amino acids a truncation to amino acid 607 did not result in a loss of toxicity). Therefore, the C-terminal half of the protein is not required for toxicity. Others have also reported that the Lepidopteran-type toxin genes which contain C-terminal deletions are more highly expressed in transformed plants. There are also reports that to retain toxicity, only small truncations can be made at the N-terminus (Schnepf et al. 1985, and Hofte et al. 1986). Contrary to those teachings it has now been found that the Coleopteran-type toxin of *B.t.t.* has substantially different properties. That is, the C-terminal portion appears to be critical for toxicity therefore permitting essentially no truncations. However, N-terminal deletions can be made and maintain toxicity. These differences were uncovered using the constructs described below:

Construction of pMON5426 (BglII/BamHI Deletion)

pMON5420 was digested with BglII and BamHI, ligated and transformed into JM101 to create pMON5426. This deletion was constructed to confirm that the BglII site was not within the coding region of the *B.t.t.* toxin gene.

Construction of pMON5438 (HpaI, C-terminal Deletion of 463 bp)

pMON5420 was digested with HpaI and ligated with the following synthetic terminator linker. The linker contains nonsense codons in each reading frame and a BglII 5' overhang.

| | |
|---|---|
| 5'-TAGTAGGTAGCTAGCCA-3' | (SEQ ID NO:41) |
| 3'-ATCATCCATCGATCGGTCTAG-5' | (SEQ ID NO:42) |

The ligation was digested with BglII, to remove multiple linker inserts and then re-ligated. The ligation was transformed into JM101 and pMON5430 was isolated. To generate a NcoI site at the start of the truncated gene, the 2.32 kb PstI fragment of pMON9759 was replaced with the 1.47 kb PstI fragment of pMON5430 and the new construct was designated pMON5434. The 1.57 kb NcoI/HindIII fragment from pMON5434 was cloned into the *E. coli* high expression vector pMON5634, to create pMON5438.

Construction of pMON5441 (EcoRV, C-terminal Deletion of 327 bp)

pMON5420 was digested with EcoRV and ligated with the synthetic terminator linker. The ligation was digested with BglII, to remove multiple linker inserts and then re-ligated. The ligation was transformed in JM101 and pMON5431 was isolated. To generate a NcoI site at the start of the truncated gene, the 2.32 kb PstI fragment of pMON9759 was replaced with the 1.61 kb Pst fragment of pMON5431, and the new construct was designated pMON5435. The 1.71 kb NcoI/HindIII fragment from pMON5435 was cloned into the *E. coli* high expression vector pMON5433 to create pMON5441.

Construction of pMON5449 (Bal3l, C-terminal Deletion of 190 bp)

BglII digested pMON9759 was treated with Bal3l nuclease for 5 min. following the manufacturer's instructions. The DNA was electrophoresed in a 0.8% agarose gel and purified from the agarose by the freeze thaw method. The synthetic terminator linker was then ligated to the purified DNA and pMON5442 was isolated. The NcoI/BglII fragment of pMON9759 was replaced with the truncated gene fragment from pMON5442 to create pMON5445. The NcoI/HindIII fragment from pMON5445 was cloned into the *E. coli* high expression vector pMON5634 to create pMON5449. The endpoint at the Bal3l created deletion was determined by DNA sequence analysis.

Construction of pMON5448 (XmnI, C-terminal Deletion of 16 bp)

pMON5436 was digested with XmnI and ligated with the synthetic terminator linker. The ligation was then digested with NcoI and BglII and the 1.92 kb NcoI/BglII fragment containing the truncated gene was cloned into NcoI and BlgII digested pMON9759 to replace the full-length gene and create pMON5446. The NcoI/HindIII fragment from pMON5446 was cloned into *E. coli* high expression vector pMON5634 to create pMON5448.

Construction of pMON5450 (NcoI fill-ends, Removal of First ATG from Toxin ORF pMON5436 was digested with NcoI, the ends filled using Klenow fragment DNA polymerase, ligated and transformed into JM101 to create pMON5450. This plasmid expresses only band 3 protein.

Construction of pMON5452 (N-terminal, Deletion of 224 bp) The *B.t.t.* gene contains two StyI sites (227 and 1587) and a third site was added by the mutagenesis to create a NcoI site in pMON9759. The following experiments were performed to delete 5' *B.t.t.* DNA to base pair 227. pMON5434 (HpaI deletion derivative described above) was digested with StyI, the ends filled with Klenow DNA polymerase, ligated, and transformed into JM101 to isolate pMON5444. This manipulation destroys both the NcoI and StyI cleavage sites. This manipulation creates an in frame fusion with the first methionine (amino acid 1) and leucine (amino acid 77). The C-terminus of the gene was added by cloning the 1.9 kb NdeI/KpnI fragment from pMON9759 into pMON5444 to create pMON5452.

Construction of pMON5456 (Band 3 Mutant, N-terminal Deletion of 140 bp)

A NcoI site was introduced into pMON5420 at the ATG for band 3 by site directed mutagenesis as described above using the primer:

Mutagenesis Primer—BTTLOOP (SEQ ID NO:43)

CGTATTATTATCTGCATCCATGGTTCTTCCTCCCT to create pMON5455. The mutagenesis also deleted the upstream sequence which encodes the N-terminal 48 amino acids of band 1. The NcoI/HindIII fragment from pMON5455 was cloned into the *E. coli* high expression vector pMON5634 to create pMON5456. This plasmid expresses only band 3. The generation of the NcoI site changes the second amino acid from thionine to aspartic acid.

Construction of pMON5460 (Mutant Band 1 Gene with MET48 Changed to ILE)

The codon for methionine at position 48 in pMON9759 was changed to a codon for isoleucine by site directed mutagenesis as described above using the primer:

Mutagenesis Primer—BTTMET (SEQ ID NO:44)

ATTATTATCTGCAGTTATTCTTAAAAACTCTTTAT to create pMON5458. The NcoI/HindIII fragment of pMON5458 was cloned into the *E. coli* high expression vector pMON5634 to create pMON5460. By removing the ATG codon which initiates translation of band 3 protein, pMON5460 produces only band 1 protein with an isoleucine residue at position 48.

Construction of pMON5467 (Band 5 Mutant, N-terminal Deletion of 293 bp)

A NcoI site was introduced into pMON5420 to create a N-terminal deletion of ninety-eight amino acids by site directed mutagenesis using the primer:

Mutagenesis—Primer (SEQ ID NO:45)

TCACTTGGCCAAATTGCCATGGTATTTAAAAAGTTTGT to create pMON5466. A methionine and alanine were also inserted by the mutagenesis. The NcoI/HindIII fragment from pMON5466 was cloned into the *E. coli* high expression vector pMON5634 to create pMON5467.

INSECT TOXICITY RESULTS

C-Terminal Truncations

Coleopteran-toxin activity was determined using newly hatched Colorado potato beetles in a tomato leaf feeding assay as previously described. The mutant *B.t.t.* genes used for analysis of the C-terminus are shown in FIGS. 8 and 10. pMON5438 contains 490 amino acids of *B.t.t.* toxin protein plus 3 amino acids encoded by the linker used in the vector construction. The truncated protein was produced at high levels in *E. coli*, but had no activity against Colorado potato beetle. pMON5441 produces a protein which contains 536 amino acids of the *B.t.t.* toxin. The truncated protein was produced at high levels in *E. coli* but had no activity against Colorado potato beetle. pMON5449 contains 582 amino acids of the *B.t.t.* protein plus two amino acids encoded by the linker used in the vector construction. The truncated protein was produced at high levels in *E. coli*, but had no activity against Colorado potato beetle. pMON5448 contains 640 amino acids of the *B.t.t.* protein plus 2 amino acids encoded by the linker used in the vector construction. The truncated protein was produced at high levels by *E. coli*, but the protein had no activity against Colorado potato beetle. These results suggest that the C-terminus of the *B.t.t.* toxin protein is required for toxicity to Colorado potato beetle. A deletion of only 4 amino (pMON5448) acids resulted in a complete loss of activity. These results are directly contrary to the reported literature with respect to Lepidopteran-type *B.t.* toxins.

Results for N-Terminal Mutations and Deletions

Figure 9B:
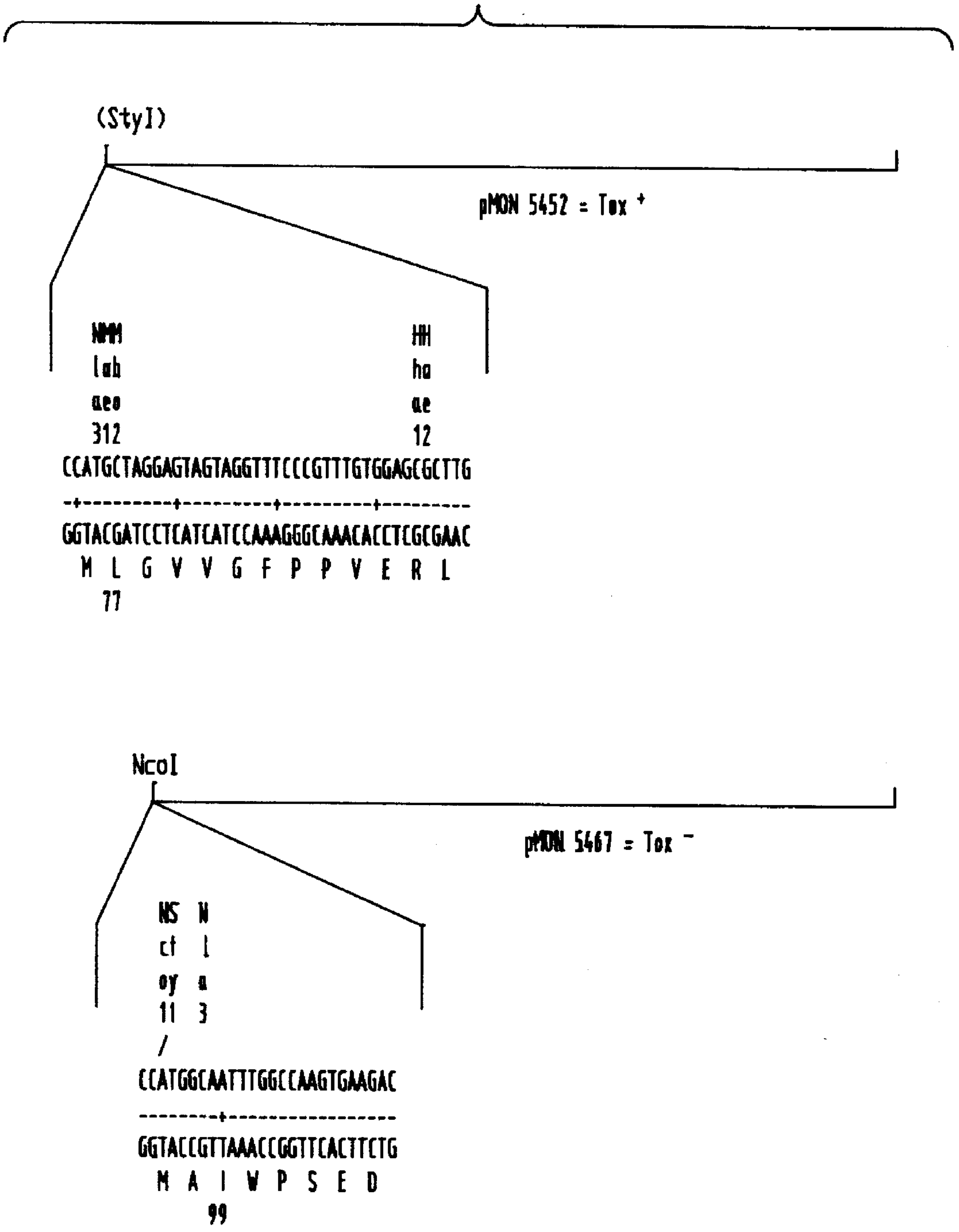

The other mutant *B.t.t.* genes used for analysis of the N-terminus are shown in FIGS. 9 and 10. Analysis of protein produced by pMON5450 revealed that band 3 production in *E. coli* was due to translation initiation at MET48 rather than a product of protease cleavage. Toxicity studies also showed that band 3 was toxic. pMON5456 produces a protein which begins at amino acid 48 with amino acid 49 changed from threonine to aspartic acid. This protein was produced at high levels in *E. coli* and was toxic to Colorado potato beetle. pMON5452 produces a protein which begins at amino acid 77. This protein was expressed in *E. coli*, and it had activity against Colorado potato beetle. pMON5467 produces a protein which begins at amino acid 99 and has two amino acids added to the N-terminus (methionine and alanine). This protein was produced in *E. coli* and exhibited no detectable activity against Colorado potato beetle, however, the level of expression for this deletion variant was significantly lower than other variants. These results suggest that the N-terminus of the *B.t.t.* toxin protein can tolerate deletions. A deletion of 76 amino acids exhibitied toxicity. A deletion of 99 amino acids did, however, result in a loss of toxicity. pMON5460 contains a mutation which changed methionine at position 48 to isoleucine to prevent production of band 3. The toxicity of band 1 produced by pMON5460 was equal to the toxicity of band 3 produced by pMON5456.

CONSTRUCTION OF PLANT TRANSFORMATION VECTORS

The *B.t.* var. *tenebrionis* toxin gene contained in pMON5420 was modified for incorporation into plant expression vectors. A BglII site was introduced just upstream of the ATG codon which specifies the initiation of translation of the full-length *B.t.t.* toxin protein (referred to as band 1) using the site specific mutagenesis protocol of Kunkel (1985) as previously described. The sequence of the *B.t.t.* toxin gene in the region of the initiator ATG is:

ATGATAAGAAAGGGAGGAAGAAAAATGAATCCGAACAA TCGAAGTGAACAT GATACAATA (SEQ ID NO:46)

MetAsnProAsnAsnArgSerGluHisAspThrIle (SEQ ID NO:47)

The primer for this mutagenesis (bttbgl) was 27 nucleotides in length and has the sequence:

CGGATTCATT TTAGATCTTC CTCCCTT (SEQ ID NO:48)

Figure 11:
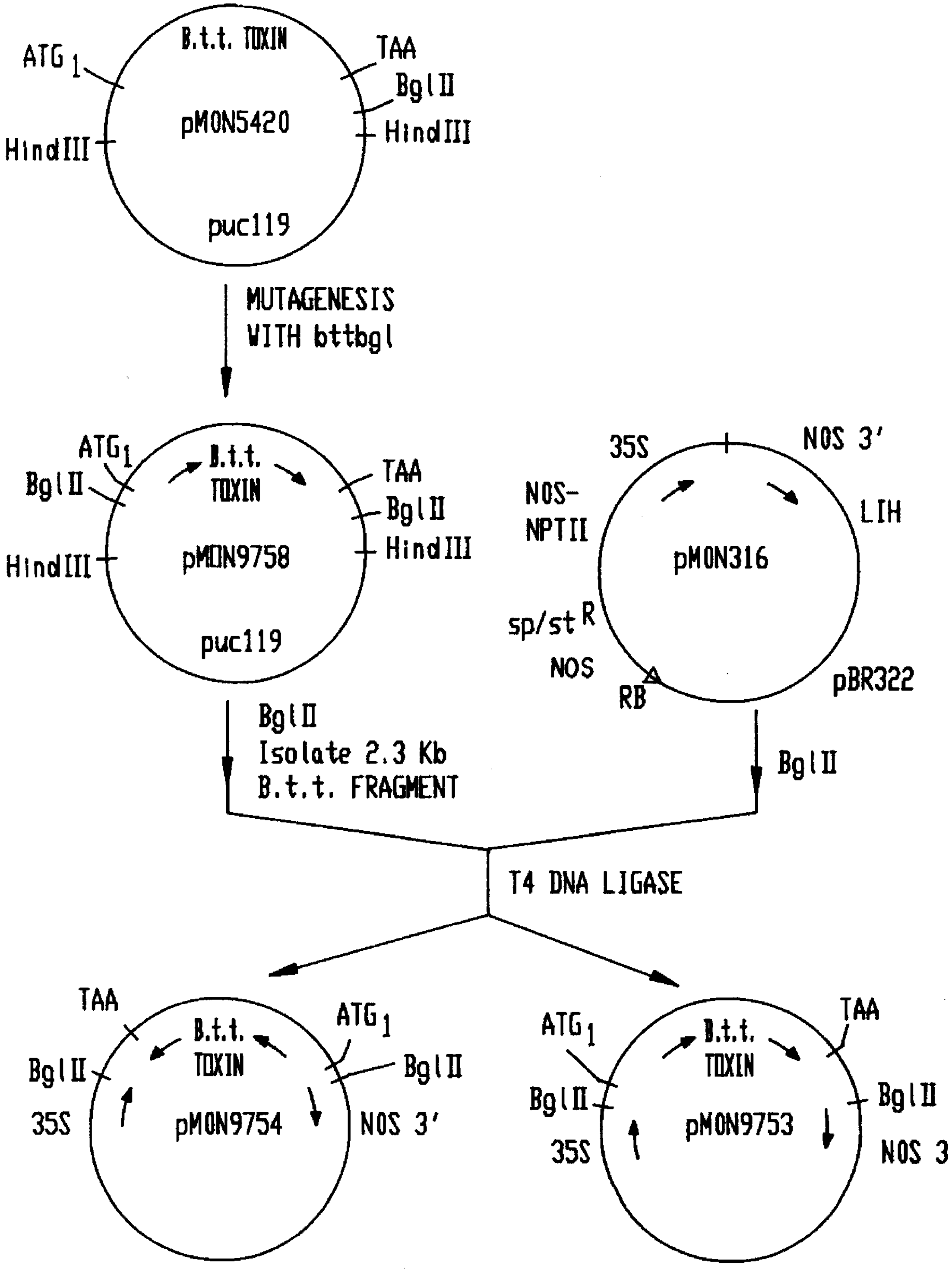
FIG. 11 shows the steps employed in preparation of plasmids pMON9758, pMON9754 and pMON9753.

Following mutagenesis a plasmid containing the new BglII site was identified by digestion with BglII and the change was verified by DNA sequence analysis. The resulting plasmid containing the *B.t.t.* toxin gene with the new BglII site was designated pMON9758 (FIG. 11).

The *B.t.t.* toxin gene in pMON9758 was inserted into the expression cassette vector pMON316 (Sanders et al., 1987). pMON316 contains the CaMV35S promoter and the 3' end from the nopaline synthase (NOS) gene with a BglII site for gene insertion between these two elements. Plasmid pMON9758 was digested with BglII and a fragment of approximately 2.3 kb was isolated. This fragment extends from the BglII site just upstream of the ATG codon to a BglII site found approximately 350 bp downstream of the termination codon for the *B.t.t.* toxin gene. Thus, this fragment contains the complete coding sequence of the *B.t.t.* gene and also about 350 bp of noncoding sequence 3' to the termination codon. This BglII fragment was ligated with BglII digested pMON316. Following transformation into *E. coli*, a colony was identified in which the *B.t.t.* toxin gene was inserted into pMON316 such that the 5' end of the toxin gene was adjacent to the CaMV35S promoter. This plasmid was designated pMON9753. A plasmid containing the *B.t.t.* toxin gene in the opposite orientation in pMON316 was isolated and designated pMON9754 (FIG. 11).

Both pMON9753 and pMON9754 were introduced by a triparental mating procedure into the *Agrobacterium tumefaciens* strain ASE which contains a disarmed Ti plasmid. Cointegrates between pMON9753 or pMON9754 and the disarmed Ti plasmid were identified as described by Fraley et al. (1985), and their structures confirmed by Southern analysis of total Agrobacterium DNA.

Figure 12:
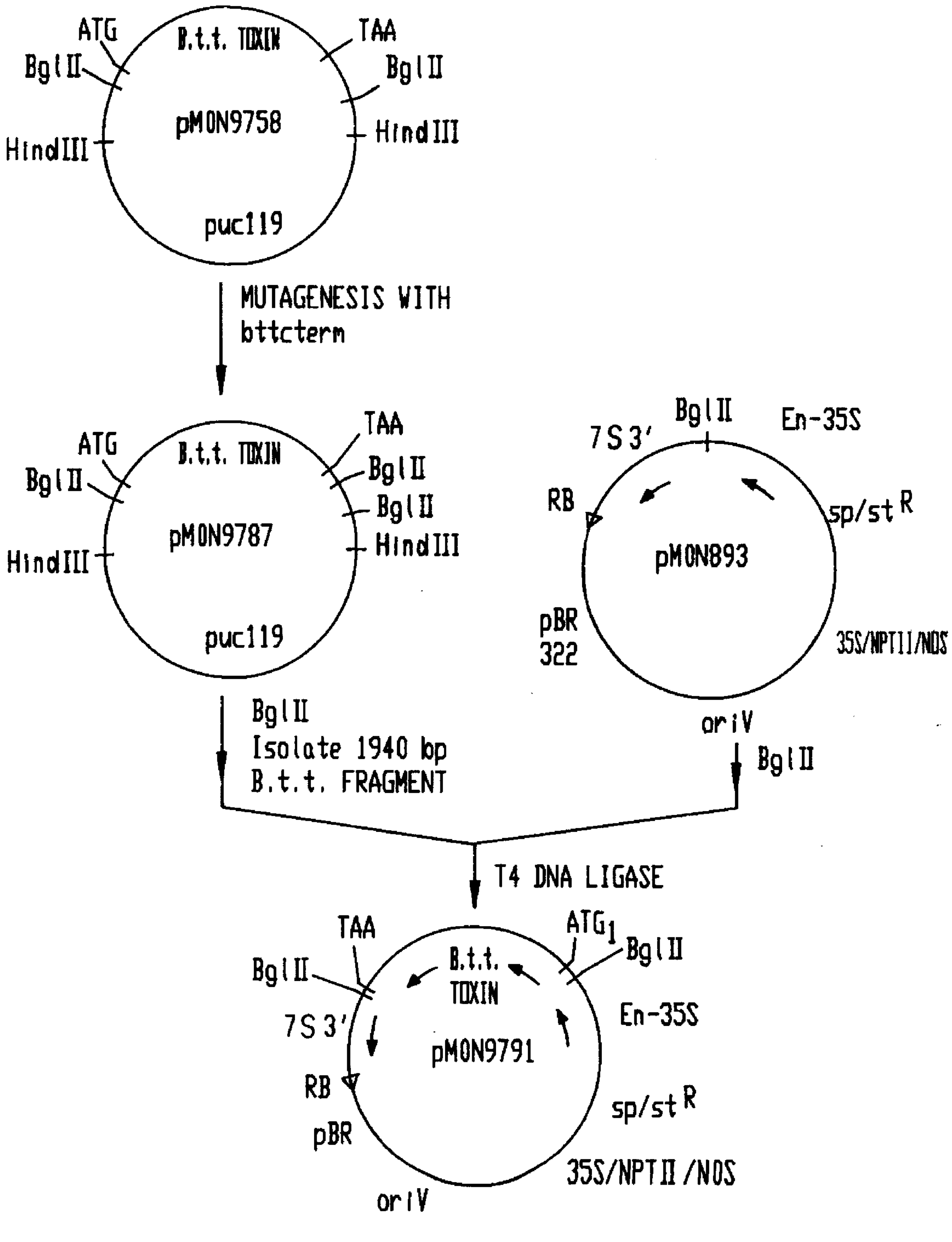
FIG. 12 shows the steps employed in preparation of plasmid pMON9791.
Figure 13:
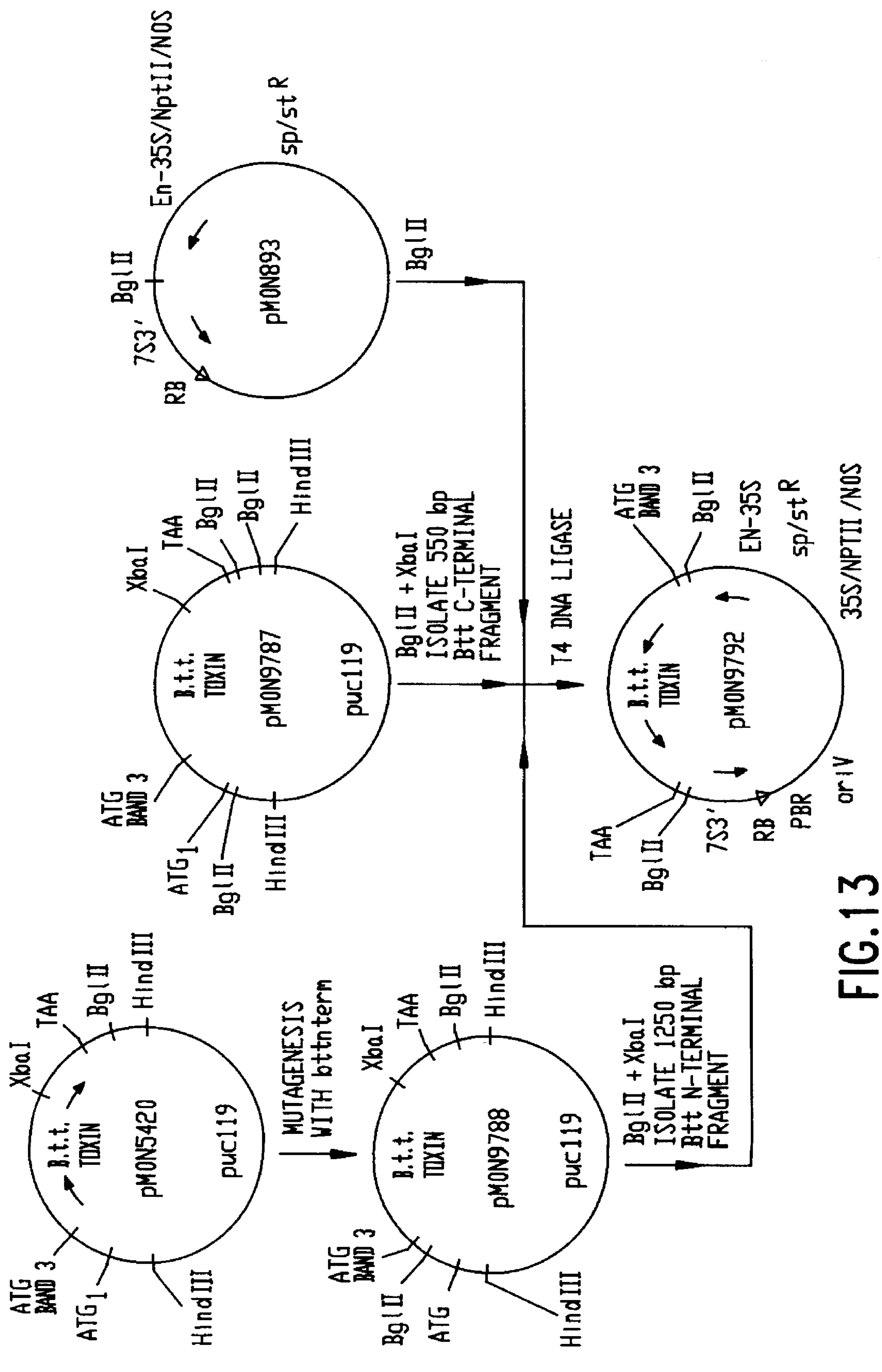
FIG. 13 shows the steps employed in preparation of plasmid pMON9792.
Figure 14:
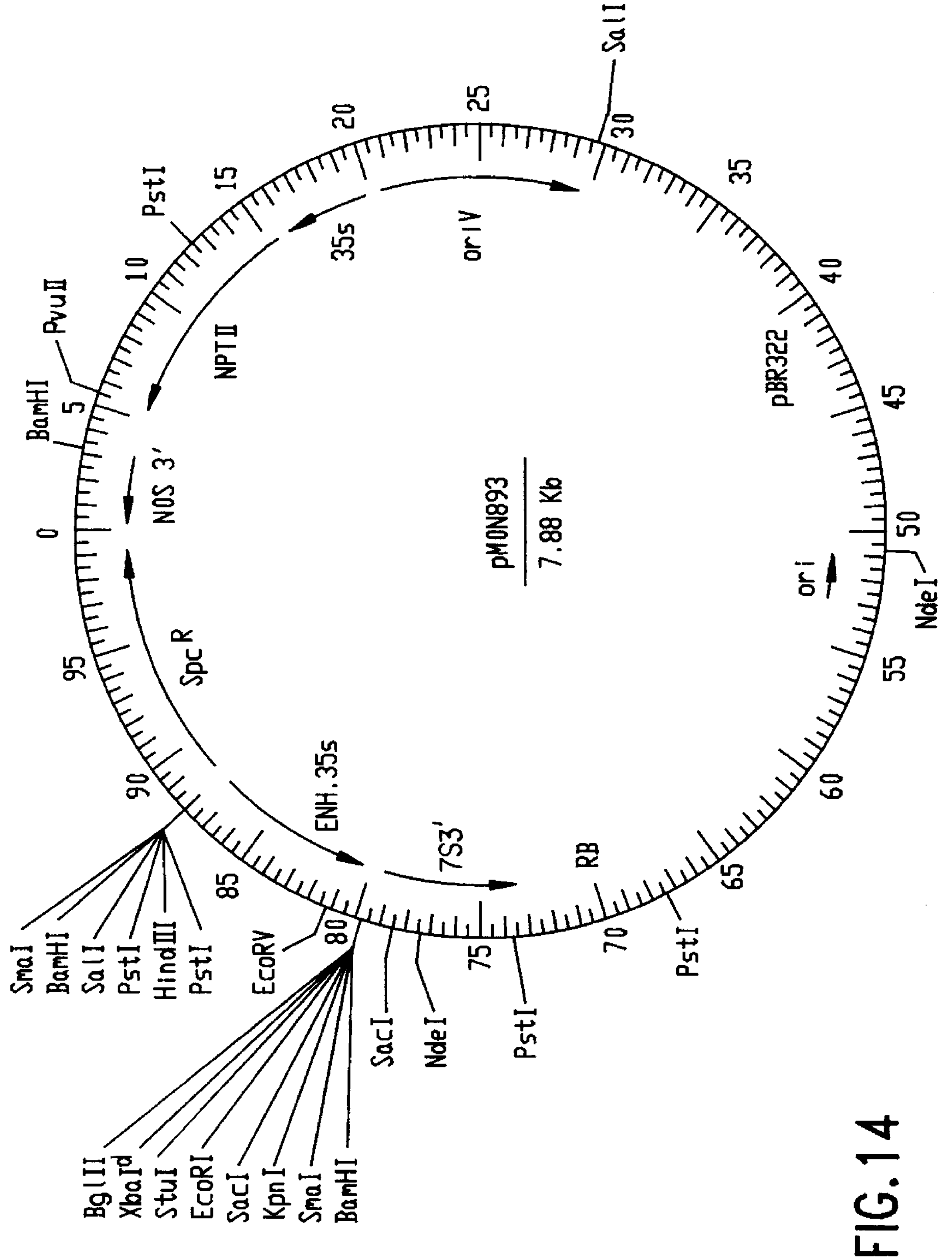
FIG. 14 shows a plasmid map for plant transformation cassette vector pMON893.

Additional plant expression vectors containing the *B.t.t.* toxin gene have also been constructed (see FIGS. 12 and 13). In these vectors the *B.t.t.* toxin gene has been inserted into the plant expression vector pMON893 (FIG. 14). Referring to FIG. 14, the expression cassette pMON893 consists of the enhanced CaMV35S promoter and the 3' end including polyadenylation signals from a soybean gene encoding the alpha-prime subunit of beta-conglycinin (referred to below as the "7S gene"). Between these two elements is a multi-linker containing multiple restriction sites for the insertion of genes.

The enhanced CaMV35S promoter was constructed as follows. A fragment of the CaMV35S promoter extending between position -343 and -90 was previously constructed in pUC13 by Odell et al. (1985). This segment contains a region identified by Odell et al. (1985) as being necessary for maximal expression of the CaMV35S promoter. It was excised as a ClaI-HindIII fragment, made blunt ended with DNA polymerase I (Klenow fragment) and inserted into the HincII site of pUC18. The upstream region of the 35S promoter was excised from this plasmid as a HindIII-EcoRV fragment (extending from -343 to -90) and inserted into the same plasmid between the HindIII and PstI sites. The enhanced CaMV35S promoter thus contains a duplication of sequences between -343 and -90 (see FIG. 18).

The 3' end of the 7S gene is derived from the 7S gene contained on the clone designated 17.1 (Schuler et al., 1982). This 3' end fragment, which includes the polyadenylation signals, extends from an AvaII site located about 30 bp upstream of the termination codon for the beta-conglycinin gene in clone 17.1 to an EcoRI site located about 450 bp downstream of this termination codon.

The remainder of pMON893 contains a segment of pBR322 which provides an origin of replication in *E. coli* and a region for homologous recombination with the disarmed T-DNA in Agrobacterium strain ACO (described below); the oriv region from the broad host range plasmid RK2; the streptomycin resistance/sprectinomycin resistance gene from Tn7; and a chimeric NPTII gene, containing the CaMV35S promoter and the nopaline synthase (NOS) 3' end, which provides kanamycin resistance in transformed plant cells.

pMON9753 contained approximately 400 bp of 3' non-coding sequence beyond the termination codon. Since this region is not necessary for toxin production it was removed from the *B.t.t.* toxin gene segments inserted in pMON893. In order to create a *B.t.t.* toxin gene containing no 3' flanking sequence, a BglII site was introduced just after the termination codon by the method of Kunkel (1985). The sequence of the *B.t.t.* toxin gene around the termination codon is:

GTTTATATAGACAAAATTGAATTTATTCCAGTGAATTAAA
TTAACTAGAAAGTAAAGAMG (SEQ ID NO:49)

ValTyrIleAspLysIleGluPheIleProValAsnEnd (SEQ ID NO:50)

Mutagenesis was performed with a primer (bttcterm) of sequence:

CTTTCTAGTT AAAGATCTTT AATTCACTG (SEQ ID NO:51)

Mutagenesis of the *B.t.t.* toxin gene was performed in pMON9758. A plasmid which contains the new BglII site was designated pMON9787 (FIG. 12). Because pMON9787 contains a BglII site just upstream of the ATG initiation codon, the full coding sequence for the *B.t.t.* toxin gene with essentially no 5' or 3' flanking sequence is contained on a BglII fragment of about 1940 bp.

This 1940 bp fragment was isolated from pMON9787 and ligated with BglII digested pMON893. A plasmid in which the 5' end of the *B.t.t.* toxin gene was adjacent to the enhanced CaMV35S promoter was identified and designated pMON9791 (FIG. 12).

A variant of the full length *B.t.t.* toxin is produced in *E. coli* from a second methionine initiator codon. This protein, designated "band 3", has been found to be as toxic to Colorado potato beetle as the full length toxin ("band 1"). It is possible that, as was the case for the *B.t.k.* gene, truncated forms of the *B.t.t.* gene might be more easily expressed in plant cells. Therefore, a modified *B.t.t.* toxin gene was constructed in which the region upstream of the band 3 ATG codon has been removed. In order to remove this sequence, a BglII site was inserted just upstream of the band 3 ATG by the method of Kunkel (1985). The sequence surrounding the band 3 ATG is:

CCAAATCCAACACTAGAAGATTTAAATTATAAAGAGTTT
TTAAGAATGACTGCAGATAAT (SEQ ID NO:52)

ProAsnProThrLeuGluAspLeuAsn-
TyrLysGluPheLeuArgMetThrAlaAspAsn (SEQ ID NO53)

Mutagenesis was performed with primer (bttnterm) of sequence:

ATCTGCAGTC ATTGTAGATC TCTCTTTATA
ATTT (SEQ ID NO:54)

Mutagenesis with this primer was performed on the *B.t.t.* toxin gene contained in pMON5420. A plasmid containing the new BglII site was designated pMON9788. A truncated *B.t.t.* toxin gene beginning at this band 3 BglII site and extending to the BglII site just distal to the termination codon found in pMON9787 was constructed in pMON893 as follows. pMON9788 (FIG. 13) was digested with BglII and XbaI and a fragment of about 1250 bp was isolated. This fragment extends from the band 3 ATG to a unique XbaI site in the middle of the *B.t.t.* toxin gene. pMON9787 was also digested with BglII and XbaI, and a fragment of about 550 bp was isolated. This fragment extends from the unique XbaI site in the middle of the toxin gene to the BglII site just distal to the termination codon. These two fragments were mixed and ligated with BglII digested pMON893. A plasmid was identified in which the 5' end to the toxin gene was adjacent to the enhanced CaMV35S promoter and designated pMON9792. pMON9792 contains a N-terminal truncated derivative of the *B.t.t.* toxin gene (FIG. 13) which encodes only band 3.

Both pMON9791 and pMON9792 were introduced into *A. tumefaciens* strain ACO which contains a disarmed Ti plasmid. Cointegrates have been selected and have been used in the transformation of tomato and potato.

Figure 17:
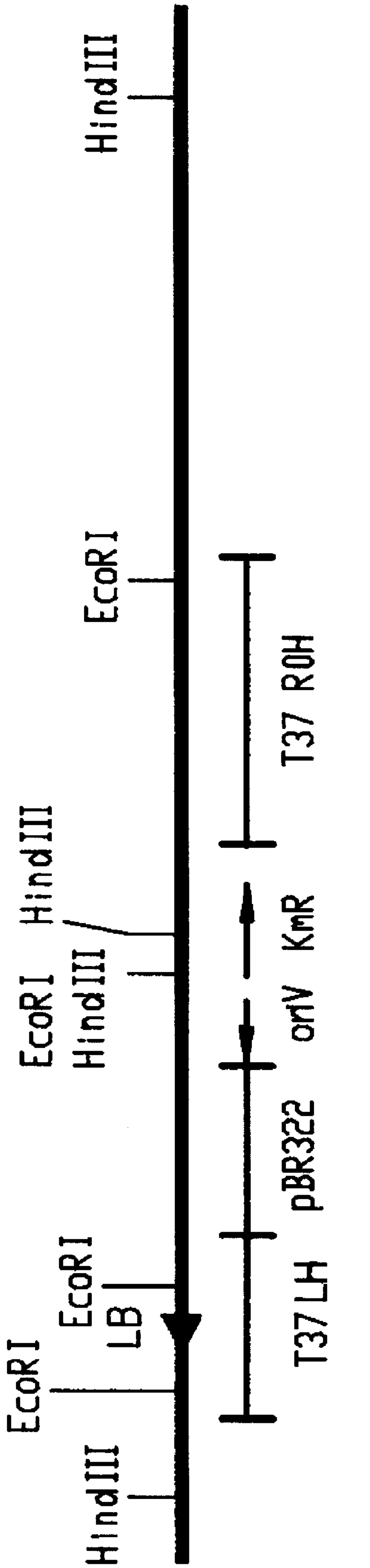
FIG. 17 illustrates the elements comprising the T-DNA region of disarmed Agrobacterium ACO.

ACO is a disarmed strain similar to pTiB6SE described by Fraley et al. (1985). For construction of ACO the starting Agrobacterium strain was the strain A208 which contains a nopaline-type Ti plasmid. The Ti plasmid was disarmed in a manner similar to that described by Fraley et al. (1985) so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to the segments in pMON893 and provide a region of homology for cointegrate formation. The structure of the ACO Ti plasmid is shown in FIG. 17.

CHIMERIC *B.t.t.* TOXIN GENE USING A MAS PROMOTER

Figure 15A:
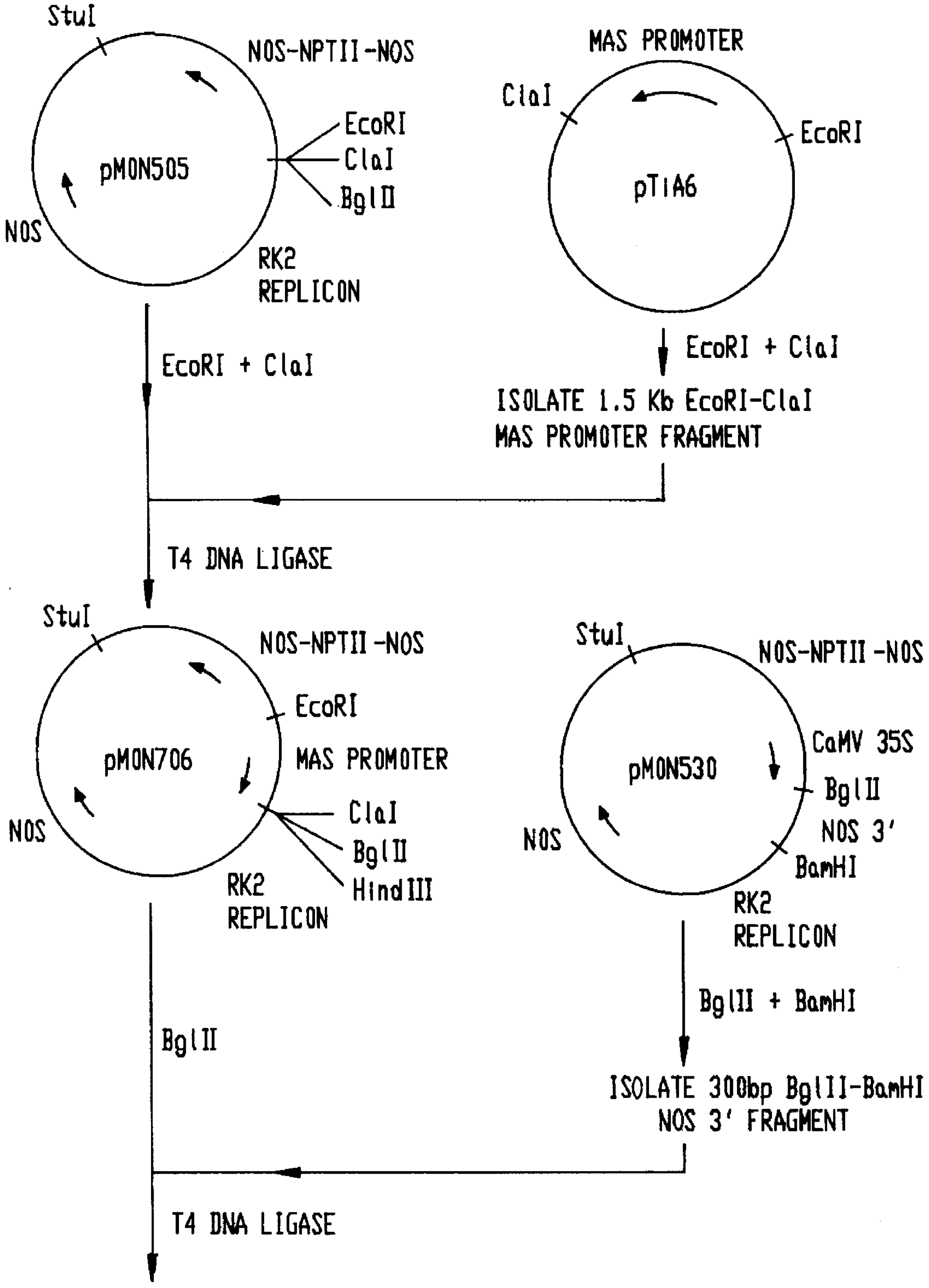
FIGS. 15A–15B show the steps employed in preparation of plasmid pMON9741.
Figure 15B:
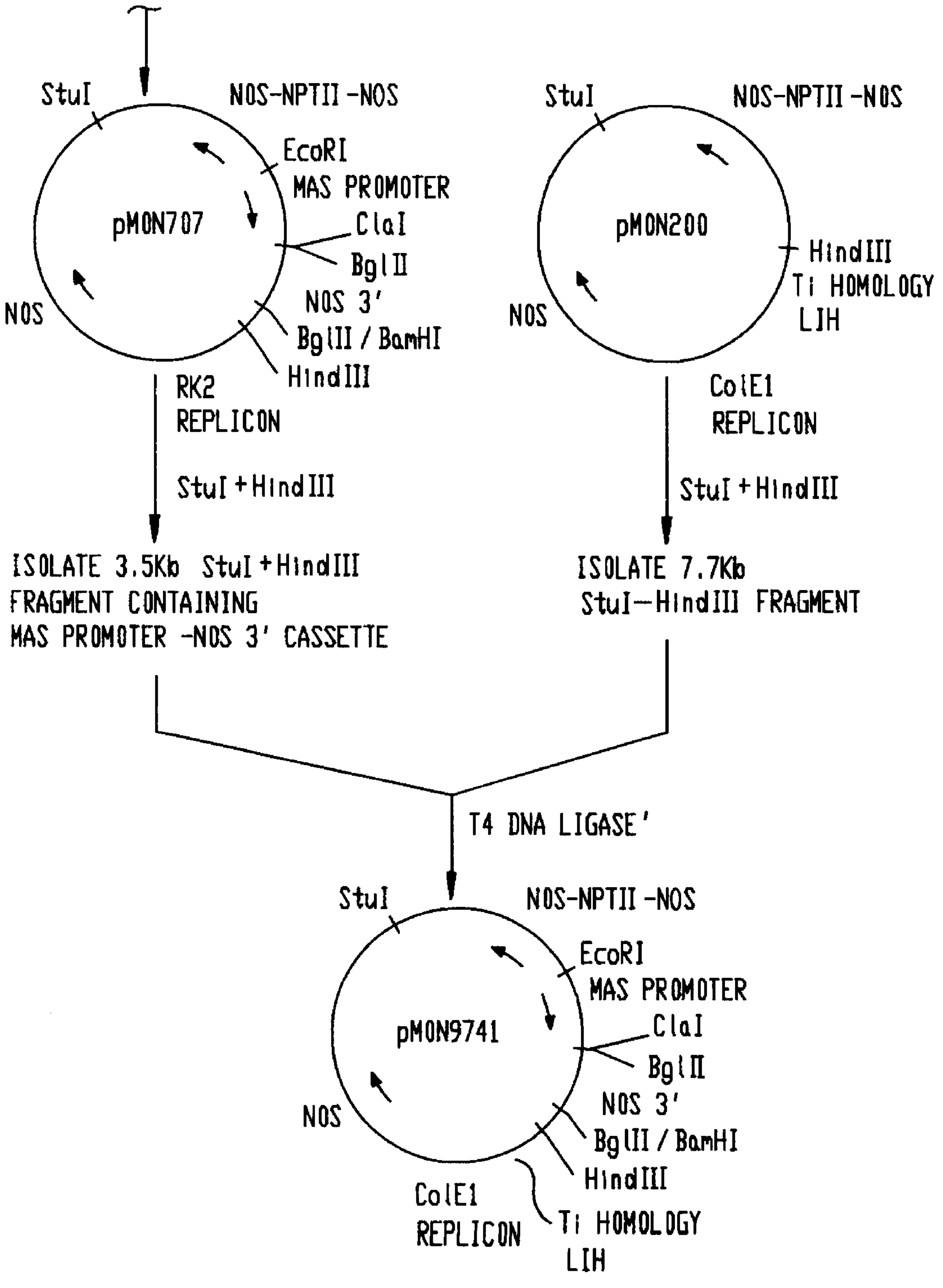

The MAS promoter was isolated from pTiA6 as a 1.5 kb EcoRI-ClaI fragment. This DNA fragment extends from the ClaI site at nucleotide 20,138 to the EcoRI site at 21,631 in the sequence of Barker et al. (1983). Referring to FIG. 15, the EcoRI-ClaI fragment was ligated with the binary vector pMON505 (Horsch et al. 1986) which had been previously digested with EcoRI and ClaI. The resulting plasmid was designated pMON706. A fragment containing the NOS 3' end was inserted downstream of the MAS promoter to obtain a MAS-NOS 3' expression cassette vector. The NOS 3' fragment was excised from pMON530 as a 300 bp BglII-BamHI fragment and inserted into BglII-digested pMON706. The resulting plasmid was designated pMON707.

Plasmid pMON530 was constructed by cleavage of pMON200 with NdeI to remove a 900 bp NdeI fragment to create pMON503. Plasmid pMON503 was cleaved with HindIII and SmaI and mixed with plasmid pTJS75 (Schmidhauser and Helinski, 1985) that had also been cleaved with HindIII and SmaI. A plasmid that contained the 3.8 kb HindIII-SmaI fragment of pTJS75 joined to the 8 kb HindIII-SmaI fragment of pMON503 was isolated and designated pMON505. Next the CaMV35S-NOS3' cassette was transferred to pMON505 by cleavage of pMON316 with StuI and HindII and isolation of the 2.5 kb StuI-HindIII fragment containing the NOS-NPTII'-NOS marker and the CaMV35S-NOS3' cassette. This was added to pMON505 DNA cleaved with StuI and HindIII. Following ligation and transformation a plasmid carrying the CaMV35S-NOS3' cassette in PMON505 was isolated and designated pMON530.

Since some binary vectors have greatly reduced frequencies of transformation in tomato as compared to co-integrating vectors, (McCormick et al., 1986), the MAS-NOS 3' cassette was moved from pMON707 into the co-integrating vector pMON200 (Fraley et al., 1985). Plasmid pMON200 was digested with StuI and HindIII and a 7.7 kb fragment isolated by agarose gel electrophoresis. Plasmid pMON707 was similarly digested with StuI and HindIII and a 3.5 kb StuI-HindIII fragment containing the MAS-NOS 3' cassette was isolated by agarose gel electrophoresis and recovery on a DEAE membranes with subsequent elution with 1M NaCl. These two DNA fragments were ligated and the resulting plasmid was designated pMON9741 (FIG. 15). This plasmid contains the MAS-NOS 3' cassette in the pMON200 co-integrating background.

Chimeric *B.t.t.* toxin genes driven by the MAS promoter are prepared by digesting either pMON9791 or pMON9792 with BglII, recovering the toxin encoding fragment and moving this fragment into pMON9741 following the teachings provided herein.

These intermediate vectors may be used to transform plants to exhibit toxicity to Coleopteran insects susceptible to the *B.t.t.* toxin protein.

COLEOPTERAN-TYPE TOXIN GENE EXPRESSION IN PLANTS

Tomato Plant Transformation The *A. tumefaciens* strains pMON9753-ASE and pMON9754-ASE were used to transform tomato leaf discs by the method of McCormick et al. (1986). Transformed tomato plants were recovered as described and assayed for kanamycin resistance.

Insect Toxicity of Transgenic Tomato Plants

Tomato plants transformed with the *B.t.t.* toxin gene contained in pMON9753 were assayed for expression of the toxin gene by bioassay with Colorado potato beetle (*Leptinotarsa decemlineata*) insects. Leaf cuttings from plants to be assayed were placed in petri dishes containing water saturated filter paper. Ten or twenty newly hatched potato beetle insects were added to the leaf cuttings and allowed to feed on the leaves. After four days the insects were scored for mortality. In addition, insects were examined for evidence of slowed growth rate (stunting), and the leaf tissue remaining was examined to determine relative feeding damage.

In each experiment many non-transformed plants were included as controls. Between 50 and 100 non-transformed plants have now been assayed as controls. Of these control plants, more than 80% show no mortality to potato beetle; about 15% give 10% mortality; and, 5% or fewer show 20% mortality. Mortality of greater than 20% has not been seen with a control plant.

Table VI below summarizes toxicity results obtained with several pMON9753 transgenic tomato plants.

TABLE VI

Toxicity of Transgenic Tomato Plants Containing pMON9753 to Colorado Potato Beetle

| Plant | Kanamycin[1] Resistance | Mortality of CPB (%) Assay #1 | Assay #2 | Assay #3 |
|---|---|---|---|---|
| 794 | R | 30 | 20 | |
| 810 | n.d. | 50 | 20 | 40 |
| 871 | R | 30 | 10 (stunted) | |
| 886 | R | 50 | 40 | |
| 887 | n.d. | 20 | 30 | 30 |
| 1009 | n.d. | 50 | | |
| 1044 | R | 20 (stunted) | | |
| 1046 | R | 40 (stunted) | 20 | |

[1]n.d. represents No Data

As shown in Table VI several plants have been recovered which consistently show higher levels of mortality of Colorado potato beetle than non-transformed control plants. These results indicate that the *B.t.t.* toxin gene is being expressed at levels sufficient to kill a significant number of the insects feeding on these plants.

COLEOPTERAN TOXIN EXPRESSION IN POTATO

Shoot tips of potato cultivar Kennebec are subcultured on media containing MS major and minor salts, 0.17 g/l sodium dihydrogen phosphate, 0.4 mg/l thiamine-HCl, 0.1 g/l inositol, 3% sucrose, 2.0 g/l Gelrite (Kelco Co.) at pH 5.6. Cultures are grown for 4 weeks at 24° C in a 16 hour photoperiod. Stem internodes are cut into approximately 8 mm lengths and the cut surfaces are smeared with Agrobacterium strain pMON9753-ASE which has been streaked on an LB agar plate and grown for 2 to 3 days. pMON9753-ASE which is described above contains the chimeric *B.t.t.* toxin gene driven by the CaMV35S promoter. Alternatively, Agrobacterium strains pMON9791-ACO or pMON9792-ACO containing chimeric *B.t.t.* toxin genes are used. Stem sections are placed on 0.8% agar-solidified medium containing salts and organic addenda as in Jarret et al. (1980), 3% sucrose, 3 mg/l BA and 0.1 mg/l NAA at pH 5.6. After 4 days the explants are transferred to medium of the same composition but with carbenicillin at 500 mg/l and kanamycin as the selective agent for transformed plant cells at 100 mg/l. Four weeks later the explants are transferred again to medium of the same composition but with $GA_3$ at 0.3 mg/l as the sole hormone. Callus which developed in the presence of 100 mg/l kanamycin are shown to contain the NPTII enzyme when tested by a dot blot assay indicating that the potato cells are transformed. Uninoculated control tissue is inhibited at this concentration of kanamycin. Transformed potato tissue expresses the *B.t.t.* toxin gene. *B.t.t.* toxin mRNA may be detected by Northern analysis and *B.t.t.* toxin protein may be detected by immunoassay such as Western blot analysis. However, in many cases the most sensitive assay for the presence of *B.t.t.* toxin is the insect bioassay. Colorado potato beetle larvae feeding on the transformed tissue suffer from the effects of the toxin.

This procedure for producing kanamycin resistant transformed potato cells has also been successfully used to regenerate shoots. Shoots which are 1 to 2 cm in length are removed from the explants and placed on the shoot tip maintenance medium described above where the shoots readily root.

Plants generated in this fashion are tested for transformation by assaying for expression of the NPTII enzyme and by the ability of stem segments to form callus on kanamycin containing medium. Transformed plants express the *B.t.t.* toxin gene. *B.t.t.* toxin MRNA may be detected by Northern analysis and *B.t.t.* toxin protein may be detected by immunoassay such as Western blot analysis. Colorado potato beetle larvae feeding on the transformed tissue suffer from the effects of the toxin.

COLEOPTERAN TOXIN EXPRESSION IN COTTON

Cotton seeds are surface sterilized by first soaking them for 10 minutes in a detergent solution of water to which Sparkleen soap has been added, then by agitating them for 20 min. in a 30% Chlorox solution containing 2 drops of Tween 20 per 400 mls before rinsing them twice with sterile distilled water. The seeds are then soaked in 0.4% benolate for 10 min. The benolate is poured off prior to placing the seeds aspetically onto agar solidified half strength MS salts. Seeds are germinated for 3–10 days in the dark at 32° C. The cotyledons and hypocotyls are then removed aspetically and segmented. The segments are placed onto 1) agar solidified MS medium containing 3% glucose, 2 mg/l napthalene acetic acid (NAA), and 1 mg/l kinetin (Medium MSS) or 2) Gelrite solidified MS medium containing 3% glucose, B5 vitamins, 100 mg/l inositol, 0.75 mg/l $MgCl_2$, 0.1 mg/l dichlorophenoxy acetic acid (2,4-D) and 0.1 or 0.5 mg/l kinetin (Medium MST). Callus is maintained in a 16/8 photo-period at 28° C. on either of these media until embryogenesis is initiated. Subculture of the embryogenic callus is made onto the same medium as for initiation but containing 3% sucrose instead of glucose. Somatic embryos are germinated by moving them onto Gelrite solidified Stewart's medium without plant growth regulators but containing 0.75 g/l $MgCl_2$. Germinated embryos are moved to soil in a growth chamber where they continue to grow. Plants are then moved to the greenhouse in order to set seed and flower.

Transformation of cotton tissues and production of transformed callus and plants is accomplished as follows. Aseptic seedlings are prepared as for plant regeneration. Hypocotyl and cotyledon segments are inoculated with liquid overnight Agrobacterium cultures or with Agrobacterium grown on nutrient plates. The explants are co-cultured for 2–3 days on MSS or MST medium containing 1/10 the concentration of MS salts. Explants are blotted on filter paper to remove excess bacteria and plated on MSS or MSN medium containing 500 mg/l carbenicillin amd 30–100 mg/l kanamycin. Callus which is transformed will grow on this medium and produce embryos. The embryos are grown into plants as stated for regeneration. The plants are tested for transformation by assay for expression of NPTII.

When the Agrobacterium strain used for transformation contains a chimeric *B.t.t.* toxin gene such as pMON9753, pMON9791 or pMON9792, the *B.t.t.* toxin gene is expressed in the transformed callus, embryos derived from this callus, and in the transformed plants derived from the embryos. For all of these cases, expression of the *B.t.t.* toxin mRNA may be detected by Northern analysis, and expression of the *B.t.t.* toxin protein may be detected by immunoassay such as Western blot analysis. Insect bioassay may be the most sensitive measure for the presence of toxin protein.

Insect toxicity of the callus, embryos or plants is assayed by bioassay with boll weevil larvae (*Anthonomous grandis*). Boll weevil larvae feeding on transformed cotton cells or plants expressing the *B.t.t.* toxin gene suffer from the effects of the toxin.

COLEOPTERAN TOXIN GENE EXPRESSION IN MAIZE

The following description outlines the preparation of protoplasts from maize, the introduction of chimeric *B.t.t.* toxin genes into the protoplast by electroporation, and the recovery of stably transformed, kanamycin resistant maize cells expressing chimeric *B.t.t.* toxin genes.

Preparation of Maize Protoplasts

Protoplasts are prepared from a Black Mexican Sweet (BMS) maize suspension line, BMSI (ATCC 54022) as described by Fromm et al. (1985 and 1986). BMSI suspension cells are grown in BMS medium which contains MS salts, 20 g/l sucrose, 2 mg/l (2,4-dichlorophenoxy) acetic acid, 200 mg/l inositol, 130 mg/l asparageine, 1.3 mg/l niacin, 0.25 mg/l thiamine, 0.25 mg/l pyridoxine, 0.25 mg/l calcium pantothenate, pH 5.8. Forty ml cultures in 125 ml erlenmeyer flasks are shaken at 150 rpm at 26° C. The culture is diluted with an equal volume of fresh medium every 3 days. Protoplasts are isolated from actively growing cells 1 to 2 days after adding fresh medium. For protoplast isolation cells are pelleted at 200×g in a swinging bucket table top centrifuge. The supernatant is saved as conditioned medium for culturing the protoplasts. Six ml of packed cells are resuspended in 40 ml of 0.2 M mannitol/50 mM $CaCl_2$/10 mM sodium acetate which contains 1% cellulase, 0.5% hemicellulase and 0.02% pectinase. After incubation for 2 hours at 26° C., protoplasts are separated by filtration through a 60 $\mu$m nylon mesh screen, centrigured at 200×g, and washed once in the same solution without enzymes.

Transformation of Maize Protoplasts with *B.t.t.* Toxin Gene DNA Vectors Using an Electroporation Technique Protoplasts are prepared for electroporation by washing in a solution containing 2 mM potassium phosphate pH 7.1, 4 mM calcium chloride, 140 mM sodium chloride and 0.2 M mannitol. After washing, the protoplasts are resuspended in the same solution at a concentration of $4\times10^6$ protoplasts per ml. One-half ml of the protoplast containing solution is mixed with 0.5 ml of the same solution containing 50 micrograms of supercoiled plasmid vector DNA and placed in a 1 ml electroporation cuvette. Electroporation is carried out as described by Fromm et al. (1986). As described, an electrical pulse is delivered from a 122 or 245 microFarad capacitor charged to 200 V. After 10 min. at 4° C. and 10 min. at room temperature protoplasts are diluted with 8 ml of medium containing MS salts 0.3 M mannitol, 2% sucrose, 2 mg/l 2,4-D, 20% conditioned BMS medium (see above) and 0.1% low melting agarose. After 2 weeks in the dark at 26° C., medium without mannitol and containing kanamycin is added to give a final kanamycin concentration of 100 mg/l liquid. After an additional 2 weeks, microcalli are removed from the liquid and placed on a membrane filter disk above agarose solidified medium containing 100 mg/l kanamycin. Kanamycin resistant calli composed of transformed maize cells appear after about 1–2 weeks.

Expression of *B.t.t* Toxin Genes in Maize Cells As described by Fromm et al. (1986), transformed maize cells can be selected by growth in kanamycin containing medium following electroporation with DNA vectors containing chimeric kanamycin resistance genes composed of the CaMV35S promoter, the NPTII coding region and the NOS 3' end. pMON9791 and pMON9792 contain such chimeric NPTII genes and also contain chimeric *B.t.t.* toxin genes. As decribed above, maize protoplasts are transformed by electroporation with DNA vectors where the DNA vectors are pMON9791 or pMON9792. Following selection for kanamycin resistance, the transformed maize cells are assayed for expression of the *B.t.t.* toxin gene. Assays are performed for *B.t.t.* mRNA by Northern blot analysis and for *B.t.t.* toxin protein by immunoassay such as Western blot analysis.

Assays for insect toxicity are performed by feeding transformed maize calli to Southern corn rootworm larvae (*Diabrotica undecimpunctata howardi*). Alternatively, a protein extract containing the *B.t.t.* toxin protein is prepared from transformed maize cells and this extract is incorporated into an appropriate insect diet which is fed to the Southern corn rootworm larvae. Rootworm larvae feeding on transformed calli or protein extracts of such calli suffer from the effects of the toxin.

The above examples are provided to better elucidate the practice of the present invention and are not intended, in any way, to limit the scope of the present invention. Those skilled in the art will recognize that modifications may be made without deviating from the spirit and scope of the invention as described.

REFERENCES

Abbott, W. S. (1925), *J. Econ. Entomol.* 18:265–267.

Adang, M. J., Staver, M. J., Rocheleau, T. A., Leighton, J., Barker, R. F. and Thompson, D. V. (1985) *Gene* 36:289–300.

Ammirato, P. V., et al. (eds), 3 HANDBOOK OF PLANT CELL CULTURE—CROP SPECIES (MacMillian Publ. Co. 1984).

Aronson, A. I., Beckman, W. and Dunn, P., (1986). *Microbiological Reviews* 50:1–24.

Barker, R. F., Idler, K. B., Thompson, D. V. and Kemp, J. D. (1983) *Plant Mol. Biol.* 2:335–350.

Bernhard, K. (1986). *FEMS Microbiol. Lett.* 33, 261–265.

Bevan, M., et al. (1983) *Nature* 304:184.

Birnboim, H. C. and Doly, J. (1979) *Nucleic Acid Res.* 7:1513–1524.

Conner, B. J., Reyers, A. A., Morin, C., Itakura, K. Teplitz, R. L. and Wallace, R. B. (1983). *Proc. Natl. Acad. Sci. USA* 80:278–282.

Devereux, J., Haeberli, and Smithies (1984) *Nucl. Acids Research* 12:387–395.

Ditta, G., Stanfield, S., Corbin, D. and Helinski, D. R., (1980). *Proc. Nat. Acad. Sci. USA* 77:7347–7751.

Fraley, R. T., Rogers, S. G., Horsch, R. B., Eichholtz, D. A., Flick, J. S., Fink, C. L., Hoffmann, N. L. and Sanders, P. R. (1985). *Bio/Technology* 3, 629–635.

Fromm, M., Taylor, L. P. and Walbot, V. (1985) *Proc. Nat. Acad. Sci. U.S.A.* 82:5824–5828.

Fromm, M., Taylor, L. P. and Walbot, V. (1986). *Nature* 319:791–793.

Herrera-Estrella, L., et al. (1983) *Nature* 303:209.

Herrnstadt, C., Soares, G. G., Wilcox, E. R. and Edwards, D. L. (1986). *Bio/Technology* 4, 305–308.

Horsch, R. and Klee, H., *Proc. Natl. Acad. Sci. USA* Vol. 83, 4428–4432.

Hofte, H. et al. (1986) *Eur. J. Biochem* 161:273–280.

Hunkapiller, M. W. Hewid, R. M., Dreyer, W. J. and Hood, L. E. (1983) *Methods in Enzymology* 91, 399–413.

Jarret, R. L. et al., *Physiologia Plantarum* 49:177–184 (1980).

Klee, H. J., et al., *Bio/Technology* 3:637–642 (1985).

Klier, A., Fargette, F., Ribier, J. and Rappaport, G. (1982). *EMBO J.* 1:791–799.

Krieg, A., Huger, A. M., Langerbrunch, G. A. and Schnetter, W. (1983) *Pathotyp. Z. Ang. Ent.* 96:500–508.

Krieg, A., Huger, A. M., Langerbrunch, G. A. and Schnetter, W. (1984) *Ang. Schadlingshde., Pflanzenschutz, Umweltschutz.* 57:145–150.

Kronstad, J. W., Schnepf, H. E. and Whiteley, H. R. (1983) *J. Bacteriol.* 154:419–428.

Kunkel, T.A. (1985). *Proc. Nat. Acad. Sci. USA* 82, 488–492.

Laemmli, U. K. (1970) *Nature* 227:681–685.

Maniatis, T., Fritsch, E. F. and Sambrook, J. (1982). Molecular Cloning, A Laboratory Manual. Cold Spring Harbor Laboratories, Cold Spring Harbor, N.Y.

McCormick, S., Niedermeyer, J., Fry, J., Barnason, A., Horsch, R. and Fraley, R. (1986). *Plant Cell Reports* 5, 81–84.

Odell, J. T., Nagy, F. and Chua, N. H. (1985). *Nature* 313:810–812.

Sanders, et al. (1987) *Nucleic Acids Research* 15:1543–1558.

Sanger, F., Micklen, S. and Coulson, A. R. (1977) *Proc. Nat. Acad. Sci. USA* 74:5463–5467.

Schnepf, H. E. and Whiteley, H. R. (1981). *Proc. Nat. Acad. Sci. USA* 78:2893–2897.

Schmidhauser, T. and Helinski, D., *J. Bacteriology,* 164, 446 (1985).

Schnepf, H. E., Wong, H. C. and Whiteley, H. R. (1985) *J. Biol. Chem.* 260:6264–6257.

Schuler, M. A., Schmitt, E. S. and Beachy, R. N. (1982). *Nucleic Acids Research.* 10:8225–8244.

Smith and Waterman (1981), *Adv. in App. Mathematics,* 2:482–489.

Southern, E. M. (1975) *J. Mol. Biol.* 98:503–517.

Spizizen, J. (1958) *Proc. Nat. Acad. Sci. USA* 44:1072–1078.

Towbin, H. and Gordon, J. (1984) *J. Immunol. Method.* 72:313–340.

Wabiko, H., Raymond, K. C. and Bulla, L. A. (1986) *DNA* 5:305–314.

Wood, W. I., Gitschier, J., Lasky, L. A. and Lawn, R. M. (1985) *Proc. Nat. Acad. Sci. USA* 82:1585–1588.

M13 Cloning and Sequencing Handbook, Amersham Corporation Cat. #N4502.

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
(A) LENGTH: 2615 base pairs
(B) TYPE: nucleic acid
(C) STRANDEDNESS: double
(D) TOPOLOGY: linear (xi) SEQUENCE DESCRIPTION: SEQ ID NO:1:

```
GAGCGACTAT TATAATCATA CATATTTTCT ATTGGAATGA TTAAGATTCC AATAGAATAG     60

TGTATAAATT ATTTATCTTG AAAGGAGGGA TGCCTAAAAA CGAAGAACAT TAAAAACATA    120

TATTTGCACC GTCTAATGGA TTTATGAAAA ATCATTTTAT CAGTTTGAAA ATTATGTATT    180

ATGATAAGAA AGGGAGGAAG AAAAATGAAT CCGAACAATC GAAGTGAACA TGATACAATA    240

AAAACTACTG AAAATAATGA GGTGCCAACT AACCATGTTC AATATCCTTT AGCGGAAACT    300

CCAAATCCAA CACTAGAAGA TTTAAATTAT AAAGAGTTTT TAAGAATGAC TGCAGATAAT    360

AATACGGAAG CACTAGATAG CTCTACAACA AAAGATGTCA TTCAAAAAGG CATTTCCGTA    420

GTAGGTGATC TCCTAGGCGT AGTAGGTTTC CCGTTTGGTG GAGCGCTTGT TTCGTTTTAT    480

ACAAACTTTT TAAATACTAT TTGGCCAAGT GAAGACCCGT GGAAGGCTTT TATGGAACAA    540

GTAGAAGCAT TGATGGATCA GAAAATAGCT GATTATGCAA AAAATAAAGC TCTTGCAGAG    600

TTACAGGGCC TTCAAAATAA TGTCGAAGAT TATGTGAGTG CATTGAGTTC ATGGCAAAAA    660

AATCCTGTGA GTTCACGAAA TCCACATAGC CAGGGGCGGA TAAGAGAGCT GTTTTCTCAA    720

GCAGAAAGTC ATTTTCGTAA TTCAATGCCT TCGTTTGCAA TTTCTGGATA CGAGGTTCTA    780

TTTCTAACAA CATATGCACA AGCTGCCAAC ACACATTTAT TTTTACTAAA AGACGCTCAA    840

ATTTATGGAG AAGAATGGGG ATACGAAAAA GAAGATATTG CTGAATTTTA TAAAAGACAA    900

CTAAAACTTA CGCAAGAATA TACTGACCAT TGTGTCAAAT GGTATAATGT TGGATTAGAT    960

AAATTAAGAG GTTCATCTTA TGAATCTTGG GTAAACTTTA ACCGTTATCG CAGAGAGATG   1020

ACATTAACAG TATTAGATTT AATTGCACTA TTTCCATTGT ATGATGTTCG GCTATACCCA   1080

AAAGAAGTTA AAACCGAATT AACAAGAGAC GTTTTAACAG ATCCAATTGT CGGAGTCAAC   1140

AACCTTAGGG GCTATGGAAC AACCTTCTCT AATATAGAAA ATTATATTCG AAAACCACAT   1200

CTATTTGACT ATCTGCATAG AATTCAATTT CACACGCGGT TCCAACCAGG ATATTATGGA   1260

AATGACTCTT TCAATTATTG GTCCGGTAAT TATGTTTCAA CTAGACCAAG CATAGGATCA   1320

AATGATATAA TCACATCTCC ATTCTATGGA AATAAATCCA GTGAACCTGT ACAAAATTTA   1380
```

-continued

GAATTTAATG GAGAAAAAGT CTATAGAGCC GTAGCAAATA CAAATCTTGC GGTCTGGCCG 1440

TCCGCTGTAT ATTCAGGTGT TACAAAAGTG GAATTTAGCC AATATAATGA TCAAACAGAT 1500

GAAGCAAGTA CACAAACGTA CGACTCAAAA AGAAATGTTG GCGCGGTCAG CTGGGATTCT 1560

ATCGATCAAT TGCCTCCAGA AACAACAGAT GAACCTCTAG AAAAGGGATA TAGCCATCAA 1620

CTCAATTATG TAATGTGCTT TTTAATGCAG GGTAGTAGAG GAACAATCCC AGTGTTAACT 1680

TGGACACATA AAAGTGTAGA CTTTTTTAAC ATGATTGATT CGAAAAAAAT TACACAACTT 1740

CCGTTAGTAA AGGCATATAA GTTACAATCT GGTGCTTCCG TTGTCGCAGG TCCTAGGTTT 1800

ACAGGAGGAG ATATCATTCA ATGCACAGAA AATGGAAGTG CGGCAACTAT TTACGTTACA 1860

CCGGATGTGT CGTACTCTCA AAAATATCGA GCTAGAATTC ATTATGCTTC TACATCTCAG 1920

ATAACATTTA CACTCAGTTT AGACGGGGCA CCATTTAATC AATACTATTT CGATAAAACG 1980

ATAAATAAAG GAGACACATT AACGTATAAT TCATTTAATT TAGCAAGTTT CAGCACACCA 2040

TTCGAATTAT CAGGGAATAA CTTACAAATA GGCGTCACAG GATTAAGTGC TGGAGATAAA 2100

GTTTATATAG ACAAAATTGA ATTTATTCCA GTGAATTAAA TTAACTAGAA AGTAAAGAAG 2160

TAGTGACCAT CTATGATAGT AAGCAAAGGA TAAAAAAATG AGTTCATAAA ATGAATAACA 2220

TAGTGTTCTT CAACTTTCGC TTTTTGAAGG TAGATGAAGA ACACTATTTT TATTTTCAAA 2280

ATGAAGGAAG TTTTAAATAT GTAATCATTT AAAGGGAACA ATGAAAGTAG GAAATAAGTC 2340

ATTATCTATA ACAAAATAAC CATTTTTATA TAGCCAGAAA TGAATTATAA TATTAATCTT 2400

TTCTAAATTG ACGTTTTTCT AAACGTTCTA TAGCTTCAAG ACGCTTAGAA TCATCAATAT 2460

TTGTATACAG AGCTGTTGTT TCCATCGAGT TATGTCCCAT TTGATTCGCT AATAGAACAA 2520

GATCTTTATT TTCGTTATAA TGATTGGTTG CATAAGTATG GCGTAATTTA TGAGGGCTTT 2580

TCTTTTCATC CAAAAGCCAA GTGTATTTCT CTGTA 2615

(2) INFORMATION FOR SEQ ID NO:2:

(i) SEQUENCE CHARACTERISTICS:
(A) LENGTH: 644 amino acids
(B) TYPE: amino acid
(C) STRANDEDNESS: Not Relevant
(D) TOPOLOGY: linear (xi) SEQUENCE DESCRIPTION: SEQ ID NO:2:

Met Asn Pro Asn Asn Arg Ser Glu His Asp Thr Ile Lys Thr Thr Glu
1 5 10 15

Asn Asn Glu Val Pro Thr Asn His Val Gln Tyr Pro Leu Ala Glu Thr
20 25 30

Pro Asn Pro Thr Leu Glu Asp Leu Asn Tyr Lys Glu Phe Leu Arg Met
35 40 45

Thr Ala Asp Asn Asn Thr Glu Ala Leu Asp Ser Ser Thr Thr Lys Asp
50 55 60

Val Ile Gln Lys Gly Ile Ser Val Val Gly Asp Leu Leu Gly Val Val
65 70 75 80

Gly Phe Pro Phe Gly Gly Ala Leu Val Ser Phe Tyr Thr Asn Phe Leu
85 90 95

Asn Thr Ile Trp Pro Ser Glu Asp Pro Trp Lys Ala Phe Met Glu Gln
100 105 110

Val Glu Ala Leu Met Asp Gln Lys Ile Ala Asp Tyr Ala Lys Asn Lys
115 120 125

Ala Leu Ala Glu Leu Gln Gly Leu Gln Asn Asn Val Glu Asp Tyr Val
130 135 140

-continued

```
Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560
```

-continued

```
Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn
```

(2) INFORMATION FOR SEQ ID NO:3:

(i) SEQUENCE CHARACTERISTICS:
(A) LENGTH: 15 amino acids
(B) TYPE: amino acid
(C) STRANDEDNESS: Not Relevant
(D) TOPOLOGY: linear (xi) SEQUENCE DESCRIPTION: SEQ ID NO:3:

```
Met Asn Pro Asn Asn Arg Ser Glu His Asp Thr Ile Lys Thr Thr
1               5                   10                  15
```

(2) INFORMATION FOR SEQ ID NO:4:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:4:

```
ATGAATCCNA ATAATCGNTC NGAACATGAT ACNATTAAAA CNACN                      45
```

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:5:

```
ATGAACCCNA ACAACAGAAG TGAGCACGAC ACNATCAAGA CNACN                      45
```

(2) INFORMATION FOR SEQ ID NO:6:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:6:

```
ATGAATCCNA ATAATCGGTC CGAACATGAT ACNATAAAAA CNACN                      45
```

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear -continued (xi) SEQUENCE DESCRIPTION: SEQ ID NO:7:

ATGAAYCCNA AYAAYCG 17

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:8:

GARCAYGAYA CRATHAA 17

(2) INFORMATION FOR SEQ ID NO:9:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:9:

GGAACAATCC CAGTGTTTAG TAGGTAGCTA GCCAGATCTT TATTT 45

(2) INFORMATION FOR SEQ ID NO:10:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:10:

AAATAAAGAT CTGGCTAGCT ACCTACTAAA CACTGGGATT GTTCC 45

(2) INFORMATION FOR SEQ ID NO:11:

(i) SEQUENCE CHARACTERISTICS:
(A) LENGTH: 14 amino acids
(B) TYPE: amino acid
(C) STRANDEDNESS: Not Relevant
(D) TOPOLOGY: linear (xi) SEQUENCE DESCRIPTION: SEQ ID NO:11:

Gly Thr Ile Pro Val Phe Ser Arg Leu Ala Arg Ser Leu Phe
1 5 10

(2) INFORMATION FOR SEQ ID NO:12:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:12:

TTACAGGCGG AGATTAGTAG GTAGCTAGCC AGATCTTTAT TTTC 44

(2) INFORMATION FOR SEQ ID NO:13:

(i) SEQUENCE CHARACTERISTICS:
(A) LENGTH: 44 base pairs
(B) TYPE: nucleic acid
(C) STRANDEDNESS: single
(D) TOPOLOGY: linear -continued (xi) SEQUENCE DESCRIPTION: SEQ ID NO:13:

GAAAATAAAG ATCTGGCTAG CTACCTACTA ATCTCCGCCT GTAA 44

(2) INFORMATION FOR SEQ ID NO:14:

(i) SEQUENCE CHARACTERISTICS:
(A) LENGTH: 12 amino acids
(B) TYPE: amino acid
(C) STRANDEDNESS: Not Relevant
(D) TOPOLOGY: linear (xi) SEQUENCE DESCRIPTION: SEQ ID NO:14:

Thr Gly Gly Asp Val Ala Ser Gln Ile Phe Ile Phe
1 5 10

(2) INFORMATION FOR SEQ ID NO:15:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:15:

CTCAGTTTAG ACGGGGCTAG TAGGTAGCTA GCCAGATCTT TATTT 45

(2) INFORMATION FOR SEQ ID NO:16:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:16:

AAATAAAGAT CTGGCTAGCT ACCTACTAGC CCCGTCTAAA CTGAG 45

(2) INFORMATION FOR SEQ ID NO:17:

(i) SEQUENCE CHARACTERISTICS:
(A) LENGTH: 14 amino acids
(B) TYPE: amino acid
(C) STRANDEDNESS: Not Relevant
(D) TOPOLOGY: linear (xi) SEQUENCE DESCRIPTION: SEQ ID NO:17:

Leu Ser Leu Asp Gly Ala Ser Arg Leu Ala Arg Ser Leu Phe
1 5 10

(2) INFORMATION FOR SEQ ID NO:18:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:18:

GTTTATATAG ACAAAATTGA ATTTAGTAGG TAGCTAGCCA GATCTTTATT TT 52

(2) INFORMATION FOR SEQ ID NO:19:

(i) SEQUENCE CHARACTERISTICS:
(A) LENGTH: 52 base pairs
(B) TYPE: nucleic acid
(C) STRANDEDNESS: single
(D) TOPOLOGY: linear -continued (xi) SEQUENCE DESCRIPTION: SEQ ID NO:19:

AAAATAAAGA TCTGGCTAGC TACCTACTAA ATTCAATTTT GTCTATATAA AC 52

(2) INFORMATION FOR SEQ ID NO:20:

(i) SEQUENCE CHARACTERISTICS:
(A) LENGTH: 16 amino acids
(B) TYPE: amino acid
(C) STRANDEDNESS: Not Relevant
(D) TOPOLOGY: linear (xi) SEQUENCE DESCRIPTION: SEQ ID NO:20:

Val Tyr Ile Asp Lys Ile Glu Phe Ser Arg Leu Ala Arg Ser Leu Phe
1 5 10 15

(2) INFORMATION FOR SEQ ID NO:21:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:21:

TATAAAGAGT TTTTAAGAAT AACTGCAGAT AATAATA 37

(2) INFORMATION FOR SEQ ID NO:22:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:22:

TATTATTATC TGCAGTTATT CTTAAAAACT CTTTATA 37

(2) INFORMATION FOR SEQ ID NO:23:

(i) SEQUENCE CHARACTERISTICS:
(A) LENGTH: 13 amino acids
(B) TYPE: amino acid
(C) STRANDEDNESS: Not Relevant
(D) TOPOLOGY: linear (xi) SEQUENCE DESCRIPTION: SEQ ID NO:23:

Tyr Lys Glu Phe Leu Arg Ile Thr Ala Asp Asn Asn Thr
1 5 10

(2) INFORMATION FOR SEQ ID NO:24:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:24:

CCATGGATGC AGATAATAAT ACGGAAGCAC TAGATAGCTC T 41

(2) INFORMATION FOR SEQ ID NO:25:

(i) SEQUENCE CHARACTERISTICS:
(A) LENGTH: 41 base pairs
(B) TYPE: nucleic acid
(C) STRANDEDNESS: single -continued (D) TOPOLOGY: linear (xi) SEQUENCE DESCRIPTION: SEQ ID NO:25:

AGAGCTATCT AGTGCTTCCG TATTATTATC TGCATCCATG G 41

(2) INFORMATION FOR SEQ ID NO:26:

(i) SEQUENCE CHARACTERISTICS:
(A) LENGTH: 13 amino acids
(B) TYPE: amino acid
(C) STRANDEDNESS: Not Relevant
(D) TOPOLOGY: linear (xi) SEQUENCE DESCRIPTION: SEQ ID NO:26:

Met Asp Ala Asp Asn Asn Thr Glu Ala Leu Asp Ser Ser
1 5 10

(2) INFORMATION FOR SEQ ID NO:27:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:27:

CCATGCTAGG AGTAGTAGGT TTCCCGTTTG TGGAGCGCTT G 41

(2) INFORMATION FOR SEQ ID NO:28:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:28:

CAAGCGCTCC ACAAACGGGA AACCTACTAC TCCTAGCATG G 41

(2) INFORMATION FOR SEQ ID NO:29:

(i) SEQUENCE CHARACTERISTICS:
(A) LENGTH: 13 amino acids
(B) TYPE: amino acid
(C) STRANDEDNESS: Not Relevant
(D) TOPOLOGY: linear (xi) SEQUENCE DESCRIPTION: SEQ ID NO:29:

Met Leu Gly Val Val Gly Phe Pro Phe Val Glu Arg Leu
1 5 10

(2) INFORMATION FOR SEQ ID NO:30:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:30:

CCATGGCAAT TTGGCCAAGT GAAGAC 26

(2) INFORMATION FOR SEQ ID NO:31:

(i) SEQUENCE CHARACTERISTICS:
(A) LENGTH: 26 base pairs
(B) TYPE: nucleic acid

-continued (C) STRANDEDNESS: single
(D) TOPOLOGY: linear (xi) SEQUENCE DESCRIPTION: SEQ ID NO:31:

GTCTTCACTT GGCCAAATTG CCATGG 26

(2) INFORMATION FOR SEQ ID NO:32:

(i) SEQUENCE CHARACTERISTICS:
(A) LENGTH: 8 amino acids
(B) TYPE: amino acid
(C) STRANDEDNESS: Not Relevant
(D) TOPOLOGY: linear (xi) SEQUENCE DESCRIPTION: SEQ ID NO:32:

Met Ala Ile Trp Pro Ser Glu Asp
1 5

(2) INFORMATION FOR SEQ ID NO:33:

(i) SEQUENCE CHARACTERISTICS:
(A) LENGTH: 661 base pairs
(B) TYPE: nucleic acid
(C) STRANDEDNESS: double
(D) TOPOLOGY: linear (xi) SEQUENCE DESCRIPTION: SEQ ID NO:33:

AAGCTTGCAT GCCTGCAGGT CCGATGTGAG ACTTTTCAAC AAAGGGTAAT ATCCGGAAAC 60

CTCCTCGGAT TCCATTGCCC AGCTATCTGT CACTTTATTG TGAAGATAGT GGAAAAGGAA 120

GGTGGCTCCT ACAAATGCCA TCATTGCGAT AAAGGAAAGG CCATCGTTGA AGATGCCTCT 180

GCCGACAGTG GTCCCAAAGA TGGACCCCCA CCCACGAGGA GCATCGTGGA AAAAGAAGAC 240

GTTCCAACCA CGTCTTCAAA GCAAGTGGAT TGATGTGATG GTCCGATGTG AGACTTTTCA 300

ACAAAGGGTA ATATCCGGAA ACCTCCTCGG ATTCCATTGC CCAGCTATCT GTCACTTTAT 360

TGTGAAGATA GTGGAAAAGG AAGGTGGCTC CTACAAATGC CATCATTGCG ATAAAGGAAA 420

GGCCATCGTT GAAGATGCCT CTGCCGACAG TGGTCCCAAA GATGGACCCC CACCCACGAG 480

GAGCATCGTG GAAAAAGAAG ACGTTCCAAC CACGTCTTCA AAGCAAGTGG ATTGATGTGA 540

TATCTCCACT GACGTAAGGG ATGACGCACA ATCCCACTAT CCTTCGCAAG ACCCTTCCTC 600

TATATAAGGA AGTTCATTTC ATTTGGAGAG GACACGCTGA CAAGCTGACT CTAGCAGATC 660

T 661

(2) INFORMATION FOR SEQ ID NO:34:

(i) SEQUENCE CHARACTERISTICS:
(A) LENGTH: 19 amino acids
(B) TYPE: amino acid
(C) STRANDEDNESS: Not Relevant
(D) TOPOLOGY: linear (xi) SEQUENCE DESCRIPTION: SEQ ID NO:34:

Met Xaa Pro Xaa Thr Arg Ala Leu Asp Asp Thr Ile Lys Lys Asp Val
1 5 10 15

Ile Gln Lys (2) INFORMATION FOR SEQ ID NO:35:

(i) SEQUENCE CHARACTERISTICS:
(A) LENGTH: 17 base pairs
(B) TYPE: nucleic acid
(C) STRANDEDNESS: single -continued (D) TOPOLOGY: linear (xi) SEQUENCE DESCRIPTION: SEQ ID NO:35:

TGAACATGGT TAGTTGG 17

(2) INFORMATION FOR SEQ ID NO:36:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:36:

TAGGTGATCT CTAGGCG 17

(2) INFORMATION FOR SEQ ID NO:37:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:37:

GGAACAACCT TCTCTAATAT 20

(2) INFORMATION FOR SEQ ID NO:38:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:38:

ATGAAYCCNA AYAAYCG 17

(2) INFORMATION FOR SEQ ID NO:39:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:39:

GARCAYGAYA CYATHAA 17

(2) INFORMATION FOR SEQ ID NO:40:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:40:

GATTGTTCGG ATCCATGGTT CTTCCTCCCT 30

(2) INFORMATION FOR SEQ ID NO:41:

(i) SEQUENCE CHARACTERISTICS:
(A) LENGTH: 17 base pairs
(B) TYPE: nucleic acid
(C) STRANDEDNESS: single
(D) TOPOLOGY: linear -continued (xi) SEQUENCE DESCRIPTION: SEQ ID NO:41:

TAGTAGGTAG CTAGCCA 17

(2) INFORMATION FOR SEQ ID NO:42:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:42:

GATCTGGCTA GCTACCTACT A 21

(2) INFORMATION FOR SEQ ID NO:43:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:43:

CGTATTATTA TCTGCATCCA TGGTTCTTCC TCCCT 35

(2) INFORMATION FOR SEQ ID NO:44:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:44:

ATTATTATCT GCAGTTATTC TTAAAAACTC TTTAT 35

(2) INFORMATION FOR SEQ ID NO:45:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:45:

TCACTTGGCC AAATTGCCAT GGTATTTAAA AAGTTTGT 38

(2) INFORMATION FOR SEQ ID NO:46:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:46:

ATGATAAGAA AGGGAGGAAG AAAAATGAAT CCGAACAATC GAAGTGAACA TGATACAATA 60

(2) INFORMATION FOR SEQ ID NO:47:

(i) SEQUENCE CHARACTERISTICS:
(A) LENGTH: 12 amino acids
(B) TYPE: amino acid
(C) STRANDEDNESS: Not Relevant
(D) TOPOLOGY: linear -continued (xi) SEQUENCE DESCRIPTION: SEQ ID NO:47:

Met Asn Pro Asn Asn Arg Ser Glu His Asp Thr Ile
1 5 10

(2) INFORMATION FOR SEQ ID NO:48:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:48:

CGGATTCATT TTAGATCTTC CTCCCTT 27

(2) INFORMATION FOR SEQ ID NO:49:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:49:

GTTTATATAG ACAAAATTGA ATTTATTCCA GTGAATTAAA TTAACTAGAA AGTAAAGAAG 60

(2) INFORMATION FOR SEQ ID NO:50:

(i) SEQUENCE CHARACTERISTICS:
(A) LENGTH: 12 amino acids
(B) TYPE: amino acid
(C) STRANDEDNESS: Not Relevant
(D) TOPOLOGY: linear (xi) SEQUENCE DESCRIPTION: SEQ ID NO:50:

Val Tyr Ile Asp Lys Ile Glu Phe Ile Pro Val Asn
1 5 10

(2) INFORMATION FOR SEQ ID NO:51:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:51:

CTTTCTAGTT AAAGATCTTT AATTCACTG 29

(2) INFORMATION FOR SEQ ID NO:52:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:52:

CCAAATCCAA CACTAGAAGA TTTAAATTAT AAAGAGTTTT TAAGAATGAC TGCAGATAAT 60

(2) INFORMATION FOR SEQ ID NO:53:

(i) SEQUENCE CHARACTERISTICS:
(A) LENGTH: 20 amino acids
(B) TYPE: amino acid
(C) STRANDEDNESS: Not Relevant
(D) TOPOLOGY: linear -continued (xi) SEQUENCE DESCRIPTION: SEQ ID NO:53:

```
Pro Asn Pro Thr Leu Glu Asp Leu Asn Tyr Lys Glu Phe Leu Arg Met
1               5                   10                  15

Thr Ala Asp Asn
            20
```

(2) INFORMATION FOR SEQ ID NO:54:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:54:

```
ATCTGCAGTC ATTGTAGATC TCTCTTTATA ATTT                                34
```

What is claimed is:

1. A chimeric plant gene comprising in sequence:

(a) a promoter which functions in plants to cause the production of RNA;

(b) a DNA sequence encoding SEQ ID NO:2 or an insecticidally active fragment thereof; and (c) a 3' non-translated DNA sequence which functions in plant cells to cause the addition of polyadenylate nucleotides to the 3' end of an RNA sequence.

2. The gene of claim 1, wherein the promoter is the CaMV35S promoter, the MAS promoter, or the ssRUBISCO promoter.

3. The gene of claim 1, wherein the DNA sequence encoding a Coleopteran-type toxin protein is from *Bacillus thuringiensis* var. *tenebrionis.*

4. The gene of claim 1, wherein the DNA sequence encoding a Coleopteran-type toxin protein is from *Bacillus thuringiensis* var. *san diego.*

5. The gene of claim 1, wherein:

the promoter is the CaMV35S promoter; and the CaMV35S promoter comprises SEQ ID NO:33.

6. A plant transformation vector comprising in sequence:

(a) a promoter which functions in plants to cause the production of an RNA sequence;

(b) a DNA sequence encoding SEQ ID NO:2 or an insecticidally active fragment thereof; and (c) a 3' non-translated DNA sequence which functions in plant cells to cause the addition of polyadenylate nucleotides to the 3' end of an RNA sequence.

7. The vector of claim 6, wherein the promoter is the CaMV35S promoter, the MAS promoter, or the ssRUBISCO promoter.

8. A transformed plant cell comprising a chimeric gene comprising in sequence:

(a) a promoter which functions in plants to cause the production of RNA;

(b) a DNA sequence that causes the production of an RNA sequence encoding SEQ ID NO:2 or an insecticidally active fragment thereof; and (c) a 3' non-translated DNA sequence which functions in plant cells to cause the addition of polyadenylate nucleotides to the 3' end of an RNA sequence;

wherein the plant cell exhibits toxicity toward susceptible Coleopteran insects.

9. The cell of claim 8, wherein the promoter is the CaMV35S promoter, the MAS promoter, or the ssRUBISCO promoter.

10. The cell of claim 8, wherein the DNA sequence encoding a Coleopteran-type toxin protein is from *Bacillus thuringiensis* var. *tenebrionis.*

11. The cell of claim 8, wherein the DNA sequence encoding a Coleopteran-type toxin protein is from *Bacillus thuringiensis* var. *san diego.*

12. A differentiated plant exhibiting toxicity toward susceptible Coleopteran insects, the plant comprising transformed plant cells, the transformed plant cells comprising in sequence:

(a) a promoter which functions in plants to cause the production of an RNA sequence;

(b) a DNA sequence encoding SEQ ID NO:2 or an insecticidally active fragment thereof; and (c) a 3' non-translated DNA sequence which functions in plant cells to cause the addition of polyadenylate nucleotides to the 3' end of an RNA sequence.

13. A transformed seed produced from the plant of claim 12.

* * * * *